United States Patent
Stergiou et al.

(10) Patent No.: US 8,838,523 B2
(45) Date of Patent: Sep. 16, 2014

(54) COMPRESSION THRESHOLD ANALYSIS OF BINARY DECISION DIAGRAMS

(75) Inventors: Stergios Stergiou, East Palo Alto, CA (US); Jawahar Jain, Los Altos, CA (US)

(73) Assignee: Fujitsu Limited, Kawasaki-shi (JP)

( * ) Notice: Subject to any disclaimer, the term of this patent is extended or adjusted under 35 U.S.C. 154(b) by 292 days.

(21) Appl. No.: 13/242,095

(22) Filed: Sep. 23, 2011

(65) Prior Publication Data

US 2013/0080382 A1    Mar. 28, 2013

(51) Int. Cl.
    *G06N 5/00*     (2006.01)
    *G06F 1/00*     (2006.01)
    *G06F 19/00*     (2011.01)

(52) U.S. Cl.
    CPC .......... *G06F 19/3418* (2013.01); *G06F 19/345* (2013.01); *G06F 19/3437* (2013.01); *G06F 19/3431* (2013.01); *G06F 19/3443* (2013.01)
    USPC .............................. 706/59; 704/200; 382/240

(58) Field of Classification Search
    USPC .......................................................... 706/59
    See application file for complete search history.

(56) References Cited

U.S. PATENT DOCUMENTS

| | | |
|---|---|---|
| 5,392,402 A | 2/1995 | Robrock, II |
| 5,491,817 A | 2/1996 | Gopal |
| 5,530,807 A | 6/1996 | Baker |
| 5,576,958 A | 11/1996 | Kawakatsu |
| 5,675,707 A | 10/1997 | Gorin |
| 5,802,523 A | 9/1998 | Jasuja |
| 5,815,664 A | 9/1998 | Asano |
| 5,875,311 A | 2/1999 | Bertram |
| 5,878,218 A | 3/1999 | Maddalozza, Jr. |
| 5,913,214 A | 6/1999 | Madnick |
| 5,958,052 A | 9/1999 | Bellovin |
| 5,976,083 A | 11/1999 | Richardson |
| 6,282,537 B1 | 8/2001 | Madnick |
| 6,298,451 B1 | 10/2001 | Lin |
| 6,306,087 B1 | 10/2001 | Barnhill |
| 6,381,597 B1 | 4/2002 | Lin |
| 6,389,374 B1 | 5/2002 | Jain |

(Continued)

FOREIGN PATENT DOCUMENTS

| | | |
|---|---|---|
| EP | 0550809 | 7/1993 |
| GB | 2466341 A | 6/2010 |

(Continued)

OTHER PUBLICATIONS

Cayirci, Erdal, "Distributed Spatial Data Aggregation and Dilutions Based on Hashing and Relational Algebra in Wireless Sensor Networks," *Proceedings of ISSNIP*, 2004.

(Continued)

*Primary Examiner* — Alan Chen
*Assistant Examiner* — Kalpana Bharadwaj
(74) *Attorney, Agent, or Firm* — Baker Botts L.L.P.

(57) ABSTRACT

In particular embodiments, a method includes receiving data sets, constructing a first binary decision diagram (BDD) representing the data sets, iteratively adding data from the data sets to the first BDD until a compression rate of the first BDD reaches a threshold compression rate, constructing a second BDD representing data from the data sets received after the compression rate of the first BDD equals a threshold compression rate, and iteratively adding data from the data sets to the second BDD.

22 Claims, 11 Drawing Sheets

(56) References Cited

U.S. PATENT DOCUMENTS

| | | | |
|---|---|---|---|
| 6,430,558 | B1 | 8/2002 | Delano |
| 6,480,837 | B1 | 11/2002 | Dutta |
| 6,480,860 | B1 | 11/2002 | Monday |
| 6,493,460 | B1 | 12/2002 | Macaulay |
| 6,546,385 | B1 | 4/2003 | Mao |
| 6,583,404 | B1 | 6/2003 | Sakurai |
| 6,643,648 | B1 | 11/2003 | Ross |
| 6,701,296 | B1 | 3/2004 | Kramer |
| 6,704,723 | B1 | 3/2004 | Alavi |
| 6,728,727 | B2 | 4/2004 | Komine |
| 6,778,991 | B2 | 8/2004 | Tenorio |
| 6,779,077 | B1 | 8/2004 | Bakke |
| 6,807,265 | B2 | 10/2004 | Boehmke |
| 6,813,731 | B2 | 11/2004 | Zahavi |
| 6,907,386 | B1 | 6/2005 | Liggesmeyer |
| 7,159,059 | B2 | 1/2007 | McNeil |
| 7,290,229 | B2 | 10/2007 | Baumgartner |
| 7,844,924 | B2 | 11/2010 | Sasao |
| 8,099,690 | B2 | 1/2012 | Goswami |
| 2001/0005804 | A1 | 6/2001 | Rayner |
| 2002/0078431 | A1* | 6/2002 | Reps ............................ 717/100 |
| 2002/0091686 | A1 | 7/2002 | Keith |
| 2002/0150285 | A1 | 10/2002 | Nelson |
| 2002/0169587 | A1 | 11/2002 | Emek |
| 2003/0154476 | A1 | 8/2003 | Abbott, III |
| 2003/0220926 | A1 | 11/2003 | Huelsman |
| 2004/0093093 | A1 | 5/2004 | Andrews |
| 2004/0139136 | A1 | 7/2004 | Goubin |
| 2004/0147840 | A1 | 7/2004 | Duggirala |
| 2004/0181500 | A1 | 9/2004 | Huelsman |
| 2004/0193036 | A1 | 9/2004 | Zhou |
| 2004/0199332 | A1 | 10/2004 | Iliff |
| 2004/0220975 | A1 | 11/2004 | Carpentier |
| 2004/0260667 | A1 | 12/2004 | Huelsman |
| 2005/0126306 | A1 | 6/2005 | Wang |
| 2005/0240885 | A1 | 10/2005 | Ganai |
| 2006/0112119 | A1 | 5/2006 | Vian |
| 2006/0274928 | A1 | 12/2006 | Collins |
| 2007/0021689 | A1 | 1/2007 | Stergiou |
| 2007/0150429 | A1 | 6/2007 | Huelsman |
| 2007/0167844 | A1 | 7/2007 | Asada |
| 2007/0204020 | A1 | 8/2007 | Anderson |
| 2007/0276970 | A1 | 11/2007 | Werner |
| 2008/0100704 | A1 | 5/2008 | Venetianer |
| 2008/0112627 | A1 | 5/2008 | Oda |
| 2008/0243746 | A1 | 10/2008 | Stergiou |
| 2008/0249379 | A1 | 10/2008 | Furman |
| 2008/0270337 | A1 | 10/2008 | Huelsman |
| 2008/0282207 | A1 | 11/2008 | Baumgartner |
| 2009/0055458 | A1 | 2/2009 | O'Neil |
| 2009/0069637 | A1 | 3/2009 | Healey |
| 2009/0077104 | A1 | 3/2009 | Sheets |
| 2009/0210470 | A1* | 8/2009 | Sarlos et al. ................... 708/400 |
| 2009/0226065 | A1 | 9/2009 | Chen |
| 2009/0313201 | A1 | 12/2009 | Huelsman |
| 2009/0327733 | A1 | 12/2009 | McDougal |
| 2010/0036835 | A1 | 2/2010 | Stergiou |
| 2010/0050145 | A1 | 2/2010 | Baumgartner |
| 2011/0055545 | A1* | 3/2011 | Sovio et al. ................... 713/150 |
| 2011/0099175 | A1 | 4/2011 | Darcy |
| 2011/0264804 | A1 | 10/2011 | Vuksan |

FOREIGN PATENT DOCUMENTS

| | | |
|---|---|---|
| WO | WO 00/26824 | 5/2000 |
| WO | WO 2005/088473 | 9/2005 |
| WO | WO 2008/099290 | 8/2008 |

OTHER PUBLICATIONS

Deshpande, Amol et al., "Model-Based Querying in Sensor Networks," *University of Maryland*, 2010.

Gray, Alasdair J. G. et al, "A Semantically Enabled Service Architecture for Mash Ups over Streaming and Stored Data," 8th Extended Semantic Web Conference, Heraklion, Greece, 2011.

Jain, Jawahar et al., "Probabilistic Design Verification," *IEEE International Conference on ICCAD-91 Digest of Technical Papers*, Section 2.2, Properties of Hash Codes, 1991.

Kowshik, Hemant et al., "Zero-error Function Computation in Sensor Networks," *Joint 48th IEEE Conference on Decision and Control and 28th Chinese Control Conference*, Shanghai, 2009.

Krenz, Rene et al.; "Improved Boolean Function Hashing based on Multiple- Vertex Dominators," *IEEE Design Automation Conference*, vol. 1, 573-578, 2005.

Liu, Mengmeng et al., "Maintaining Recursive Views of Regions and Connectivity in Networks," *IEEE Transactions on Knowledge and Data Engineering*, 22 (8), 2010.

Teslenko, Maxim et al., "Computing a Perfect Input Assignment for Probabilistic Verification," *VLSI Circuits and Systems II, Proceedings of SPIE*, v. 5837, 2005.

Tran, Duc A. et al., "Enabling Publish/Subscribe Services in Sensor Networks," University of Massachusetts, Boston and IBM Zurich Research Laboratory, Switzerland, 2010.

Search Report for GB1114025.8, Nov. 21, 2011.
Search Report for GB1113969.8, Nov. 14, 2011.
Search Report for GB1114026.6, Dec. 6, 2011.
Search Report for GB1114161.1, Dec. 16, 2011.
Search Report for GB1114155.3, Dec. 16, 2011.
Search Report for GB1114028.2 Dec. 8, 2011.
Search Report for GB1113967.2 Nov. 23, 2011.
Office Action for U.S. Appl. No. 12/857,655, Dec. 23, 2011.
Office Action for U.S. Appl. No. 12/857,613, Jan. 31, 2012.
U.S. Appl. No. 12/857,594, filed Aug. 17, 2011, Stergiou.
U.S. Appl. No. 12/857,603, filed Aug. 17, 2011, Stergiou.
U.S. Appl. No. 12/857,613, filed Aug. 17, 2011, Stergiou.
U.S. Appl. No. 12/857,628, filed Aug. 17, 2011, Stergiou.
U.S. Appl. No. 12/857,655, filed Aug. 17, 2011, Stergiou.
U.S. Appl. No. 12/857,690, filed Aug. 17, 2011, Stergiou.
U.S. Appl. No. 12/857,719, filed Aug. 17, 2011, Stergiou.
U.S. Appl. No. 12/857,768, filed Aug. 17, 2011, Stergiou.
U.S. Appl. No. 13/241,698, filed Sep. 23, 2011, Stergiou.
U.S. Appl. No. 13/241,789, filed Sep. 23, 2011, Stergiou.
U.S. Appl. No. 13/241,872, filed Sep. 23, 2011, Stergiou.
U.S. Appl. No. 13/241,991, filed Sep. 23, 2011, Stergiou.
U.S. Appl. No. 13/242,253, filed Sep. 23, 2011, Stergiou.
U.S. Appl. No. 13/243,104, filed Sep. 23, 2011, Stergiou.
U.S. Appl. No. 13/243,158, filed Sep. 23, 2011, Stergiou.
U.S. Appl. No. 13/243,271, filed Sep. 23, 2011, Stergiou.
Search Report for GB 1114027.4, Nov. 17, 2011.

Hlavička, Jan et al., "Algorithm for Minimization of Partial Boolean Functions," Czech Technical University, Prague, Apr. 2, 2000.

Ajo Mama, Amccosta et al., "Binary Decision Diagram", http://en.wikipedia.org/w/index.php?oldid=372197325, Feb. 14, 2011.

10metreh, et al., "Hash Function", http://en.wikipedia.org/w/index.php?oldid=375246104, Feb. 14, 2011.

Jain, Jawahar et al., "Probabilistic Verification of Boolean Functions", Formal Methods in System Design, 1: 61-115, Kluwer Academic Publishers, 1992.

Korn, Philip et al., "Fast and Effective Retrieval of Medical Tumor Shapes," IEEE Transactions on Knowledge and Data Engineering, 10 (6), 1998.

Prasad. P. W. C. et al., "Selective min-terms based tabular method for BOD Manipulations," World Academy of Science, Engineering and Technology Available at: http://citeseerx.ist.psu.edu/viewdoc/download?doi=10.1.1.193.698&rep=repl &type=pdf, Last visited: Oct. 7, 2012.

Li et al.; Nonthreshold-Based Event Detection for 3D Environment Monitoring in Sensor Networks; IEEE Transactions on Knowledge and Data Engineering; vol. 20; No. 12; pp. 1699-1711, Dec. 2008.

Xue et al.; Contour Map Matching for Event Detection in Sensor Networks; SIGMOD 2006; pp. 145-156, 2006.

Gupchup et al.; Model-Based Event Detection in Wireless Sensor Networks; Proceeding of the Workshop for Data Sharing and Interoperability on the World Wide Web, 2009.

Office Action for U.S. Appl. No. 12/857,655, Jun. 13, 2012.
Office Action for U.S. Appl. No. 12/857,594, Aug. 13, 2012.
Office Action for U.S. Appl. No. 12/857,603, Jul. 27, 2012.
Office Action for U.S. Appl. No. 12/857,768, Jul. 25, 2012.

(56) References Cited

OTHER PUBLICATIONS

Office Action for U.S. Appl. No. 12/857,628, Jan. 23, 2013.
Office Action for U.S. Appl. No. 12/857,628, Apr. 15, 2013.
Office Action for U.S. Appl. No. 12/857,690, Jan. 23, 2013.
Office Action for U.S. Appl. No. 12/857,690, Apr. 15, 2013.
Office Action for U.S. Appl. No. 12/857,719, Oct. 15, 2012.
Office Action for U.S. Appl. No. 12/857,768, Dec. 17, 2012.
Office Action for U.S. Appl. No. 13/243,158, Dec. 26, 2012.
Office Action for U.S. Appl. No. 13/243,158, Apr. 12, 2013.
Notice of Allowance for U.S. Appl. No. 12/857,655, Mar. 20, 2013.
Mathie et al., "Classification of Basic Daily Movements Using a Triaxial Accelerometer", Medical & Biological Engineering & Computing 2004, vol. 42, pp. 679-687, IFMBE, 2004.
Karantonis et al., "Implementation of a Real-Time Human Movement Classifier Using a Triaxial Accelerometer for Ambulatory Monitoring", IEEE Transactions on Information Technology in Biomedicine, vol. 10, No. 1, pp. 15-167, IEEE, 2006.
Office Action for U.S. Appl. No. 12/857,768, Jun. 3, 2013.
Chen, L., et al., "Efficient Algorithms for Pattern Matching on Directed Acyclic Graphs," *IEEE 21st International conference on Data Engineering*, (ICDE 2005), 2005.
Deshpande, Amol et al., "Model-Based Approximate Querying in Sensor Networks," *VLDB 2005*, pp. 1-49, 2005.
Deshpande, Amol et al., "Model-Driven Data Acquisition in Sensor Networks," *Proceedings of the 30th VLDB Conference*, Toronto, Canada, pp. 588-599, 2004.
Sun Z. et al., "Medical Image Compression Based on Ordered Binary Decision Diagrams," *IEEE First International Workshop on Education Technology and Computer Science*, 2009.
Turton, B., "Extending Quine-McCluskey for Exclusive-Or Logic Synthesis," *IEEE Transactions on Education*, vol. 39, No. 1, 1996.
Office Action for U.S. Appl. No. 12/857,719, Mar. 1, 2012.
Office Action for U.S. Appl. No. 12/857,603, Feb. 17, 2012.
Office Action for U.S. Appl. No. 12/857,594, Mar. 14, 2012.
Louis Kruger, et al., "*Secure Function Evaluation with Ordered Binary Decision Diagrams,*" CCS'06, Oct. 30-Nov. 3, 2006; 11 pgs., 2006.
Rolf Drechsler, et al., "*Binary decision diagrams in theory and practice,*" Int. J STT (2001) 3:112-136, 25 pgs., May 15, 2001.
Srcejit Chakravarty, "*A Characterization of Binary Decision Diagrams,*" IEEE Transactions on Computers, vol. 42, No. 2, 9 pgs., Feb. 1993.
Bhaskar Saha, "*A Model-Based Reasoning Architecture for System-Level Fault Diagnosis,*" School of Electrical and Computer Engineering, Georgia Institute of Technology, 106 pgs., Apr. 2008.
Non-Final Office Action for U.S. Appl. No. 13/241,872, Apr. 4, 2014.
Yaofend Wen, et al., "*Heart rate monitoring in dynamic movements from a wearable system,*" Medical Devices and Biosensors, 2008. ISSS-MDBS 2008. 5th International Summer School and Symposium on, Jun. 1-3, 2008, pp. 272-275, 2008.
D. Michael Miller, et al., "*Implementing a multiple-valued decision diagram package,*" Multiple-Valued Logic, 1998. Proceedings. 1998 28th IEEE International Symposium on, May 27-29, 1998, pp. 52-57, 1998.
Mohamed Raseen, et al., "*Mathematical model to predict the number of nodes in an ROBDD,*" Circuits and Systems, 2004. MWSCAS '04. The 2004 47th Midwest Symposium on, vol. 3, Jul. 25-28, 2004, pp. 111-431-434, 2004.
Stergios Stergiou, et al., "*Dynamically resizable binary decision diagrams,*" GLSVLSI 2010, Proceedings of the 20th symposium on Great lakes symposium on VLSI, pp. 185-190, 2010.

\* cited by examiner

COMPRESSION THRESHOLD ANALYSIS OF BINARY DECISION DIAGRAMS

TECHNICAL FIELD

This disclosure generally relates to sensors and binary decision diagrams, and in particular for monitoring and analyzing a person's health.

BACKGROUND

A sensor network may include distributed autonomous sensors. Uses of sensor networks include but are not limited to military applications, industrial process monitoring and control, machine health monitoring, environment and habitat monitoring, utility usage, healthcare and medical applications, home automation, and traffic control. A sensor in a sensor network is typically equipped with a communications interface, a controller, and an energy source (such as a battery).

A sensor typically measures a physical quantity and converts it into a signal that an observer or an instrument can read. For example, a mercury-in-glass thermometer converts a measured temperature into expansion and contraction of a liquid that can be read on a calibrated glass tube. A thermocouple converts temperature to an output voltage that a voltmeter can read. For accuracy, sensors are generally calibrated against known standards.

A binary decision diagram (BDD) is a data structure that may be used to represent a Boolean function. A reduced ordered binary decision diagram (ROBDD) is an optimized BDD that has no redundant nodes and isomorphic sub-graphs and that the variables appear in the same order along each path from root to a terminal node.

DESCRIPTION OF EXAMPLE EMBODIMENTS

Sensor Networks

Figure 1:
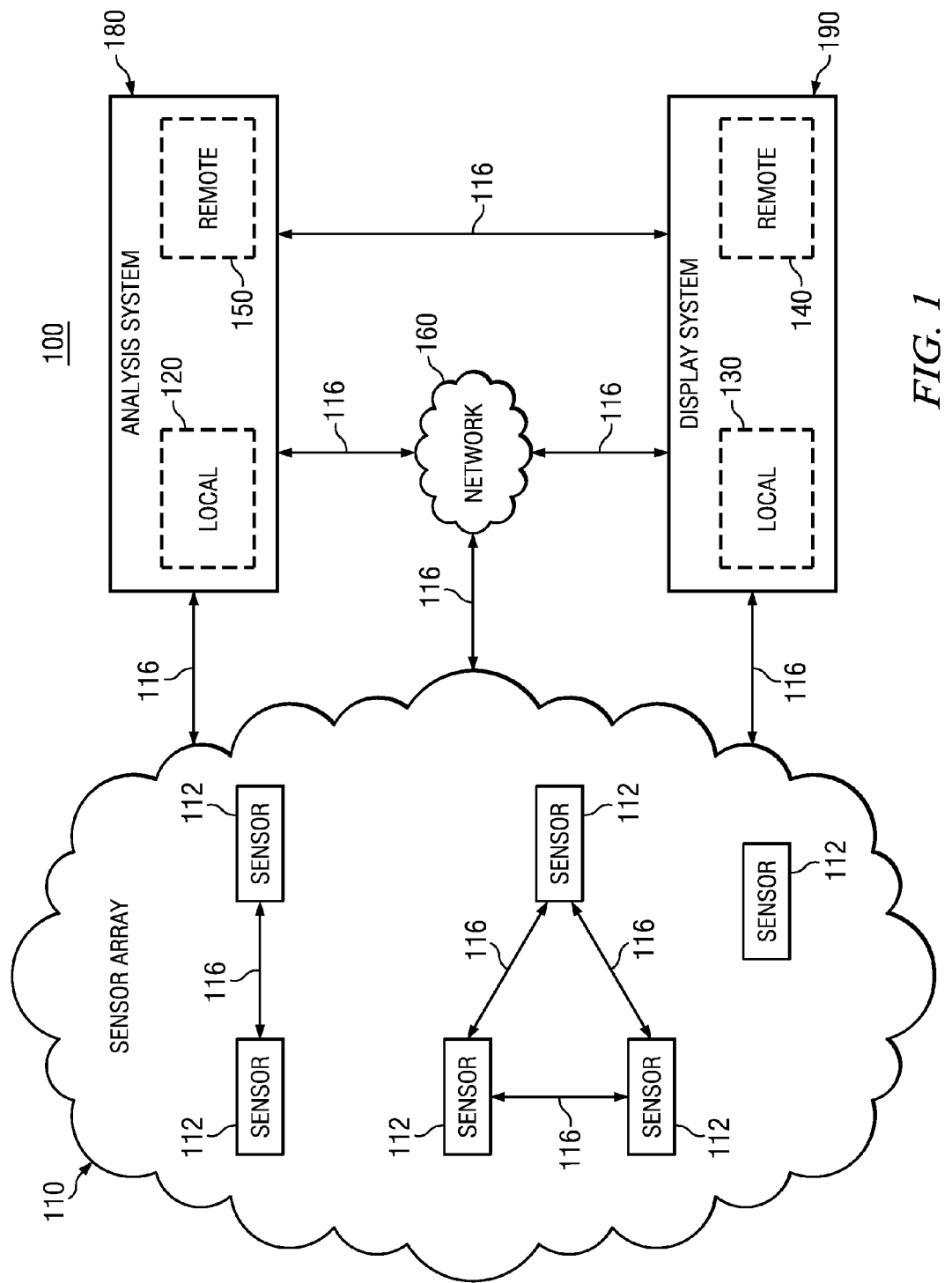
FIG. 1 illustrates an example sensor network.

FIG. 1 illustrates an example sensor network 100. Sensor network 100 comprises a sensor array 110, an analysis system 180, and display system 190. Sensor network 100 enables the collecting, processing, analyzing, sharing, visualizing, displaying, archiving, and searching of sensor data. The data collected by sensors 112 in sensor array 110 may be processed, analyzed, and stored using the computational and data storage resources of sensor network 100. This may be done with both centralized and distributed computational and storage resources. Sensor network 100 may integrate heterogeneous sensor, data, and computational resources deployed over a wide area. Sensor network 100 may be used to undertake a variety of tasks, such as physiological, psychological, behavioral, and environmental monitoring and analysis.

A sensor array 110 comprises one or more sensors 112. A sensor 112 receives a stimulus and converts it into a data stream. The sensors 112 in sensor array 110 may be of the same type (e.g., multiple thermometers) or various types (e.g., a thermometer, a barometer, and an altimeter). A sensor array 110 may transmit one or more data streams based on the one or more stimuli to one or more analysis systems 180 over any suitable network. In particular embodiments, a sensor 112's embedded processors may perform certain computational activities (e.g., image and signal processing) that could also be performed by other components of sensor network 100, such as, for example, analysis system 180 or display system 190.

As used herein, a sensor 112 in a sensor array 110 is described with respect to a subject. Therefore, a sensor 112 may be personal or remote with respect to the subject. Personal sensors receive stimuli that are from or related to the subject. Personal sensors may include, for example, sensors that are affixed to or carried by the subject (e.g., a heart-rate monitor, an input by the subject into a smart phone), sensors that are proximate to the subject (e.g., a thermometer in the room where the subject is located), or sensors that are otherwise related to the subject (e.g., GPS position of the subject, a medical report by the subject's doctor, a subject's email inbox). Remote sensors receive stimulus that is external to or not directly related to the subject. Remote sensors may include, for example, environmental sensors (e.g., weather balloons, stock market ticker), network data feeds (e.g., news feeds), or sensors that are otherwise related to external information. A sensor 112 may be both personal and remote depending on the circumstances. As an example and not by way of limitation, if the subject is a particular person, a thermometer in a subject's home may be considered personal while the subject is at home, but remote when the subject is away from home. As another example and not by way of limitation, if the subject is a particular home, a thermometer in the home may be considered personal to the home regardless of whether a person is in the home or away.

Analysis system 180 may monitor, store, and analyze one or more data streams from sensor array 110. Analysis system 180 may have subcomponents that are local 120, remote 150, or both. Display system 190 may render, visualize, display, message, and publish to one or more users based on the output of analysis system 180. Display system 190 may have subcomponents that are local 130, remote 140, or both.

As used herein, the analysis and display components of sensor network 100 are described with respect to a sensor 112. Therefore, a component may be local or remote with respect to the sensor 112. Local components (i.e., local analysis system 120, local display system 130) may include components that are built into or proximate to the sensor 112. As an example and not by way of limitation, a sensor 112 could include an integrated computing system and LCD monitor that function as local analysis system 120 and local display system 130. Remote components (i.e., remote analysis system 150, remote display system 190) may include components that are external to or independent of the sensor 112. As another example and not by way of limitation, a sensor 112 could transmit a data stream over a network to a remote server at a medical facility, wherein dedicated computing systems and monitors function as remote analysis system 150 and remote display system 190. In particular embodiments, each sensor 112 in sensor array 110 may utilize either local or remote display and analysis components, or both. In particular embodiments, a user may selectively access, analyze, and display the data streams from one or more sensors 112 in sensor array 110. This may be done, for example, as part of running a specific application or data analysis algorithm. The user could access data from specific types of sensors 112 (e.g., all thermocouple data), from sensors 112 that measure specific types of data (e.g., all environmental sensors), or based on other criteria.

Although FIG. 1 illustrates a particular arrangement of sensor array 110, sensors 112, analysis system 180, local analysis system 120, remote analysis system 150, display system 190, local display system 130, remote display system 140, and network 160, this disclosure contemplates any suitable arrangement of sensor array 110, sensors 112, analysis system 180, local analysis system 120, remote analysis system 150, display system 190, local display system 130, remote display system 140, and network 160. As an example and not by way of limitation, two or more of sensor array 110, sensors 112, analysis system 180, local analysis system 120, remote analysis system 150, display system 190, local display system 130, and remote display system 140 may be connected to each other directly, bypassing network 160. As another example, one or more sensors 112 may be connected directly to communication network 160, without being part of a sensor array 110. As another example, two or more of sensor array 110, sensors 112, analysis system 180, local analysis system 120, remote analysis system 150, display system 190, local display system 130, and remote display system 140 may be physically or logically co-located with each other in whole or in part. Moreover, although FIG. 1 illustrates a particular number of sensor arrays 110, sensors 112, analysis systems 180, local analysis systems 120, remote analysis systems 150, display systems 190, local display systems 130, remote display systems 140, and networks 160, this disclosure contemplates any suitable number of sensor arrays 110, sensors 112, analysis systems 180, local analysis systems 120, remote analysis systems 150, display systems 190, local display systems 130, remote display systems 140, and networks 160. As an example and not by way of limitation, sensor network 100 may include multiple sensor arrays 110, sensors 112, analysis systems 180, local analysis systems 120, remote analysis systems 150, display systems 190, local display systems 130, remote display systems 140, and networks 160.

This disclosure contemplates any suitable network 160. As an example and not by way of limitation, one or more portions of network 160 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 160 may include one or more networks 160. Similarly, this disclosure contemplates any suitable sensor array 110. As an example and not by way of limitation, one or more portions of sensor array 110 may include an ad hoc network, an intranet, an extranet, a VPN, a LAN, a WLAN, a WAN, a WWAN, a MAN, a portion of the Internet, a portion of the PSTN, a cellular telephone network, or a combination of two or more of these. Sensor array 110 may include one or more sensor arrays 110.

Connections 116 may connect sensor array 110, sensors 112, analysis system 180, local analysis system 120, remote analysis system 150, display system 190, local display system 130, and remote display system 140 to network 160 or to each other. Similarly, connections 116 may connect sensors 112 to each other in sensor array 110 (or to other equipment in sensor array 110) or to network 160. This disclosure contemplates any suitable connections 116. In particular embodiments, one or more connections 116 include one or more wireline (such as, for example, Digital Subscriber Line (DSL) or Data Over Cable Service Interface Specification (DOCSIS)), wireless (such as, for example, Wi-Fi or Worldwide Interoperability for Microwave Access (WiMAX)) or optical (such as, for example, Synchronous Optical Network (SONET) or Synchronous Digital Hierarchy (SDH)) connections. In particular embodiments, one or more connections 116 each include an ad hoc network, an intranet, an extranet, a VPN, a LAN, a WLAN, a WAN, a WWAN, a MAN, a portion of the Internet, a portion of the PSTN, a cellular telephone network, another connection 116, or a combination of two or more such connections 116. Connections 116 need not necessarily be the same throughout sensor network 100. One or more first connections 116 may differ in one or more respects from one or more second connections 116.

Figure 2A:
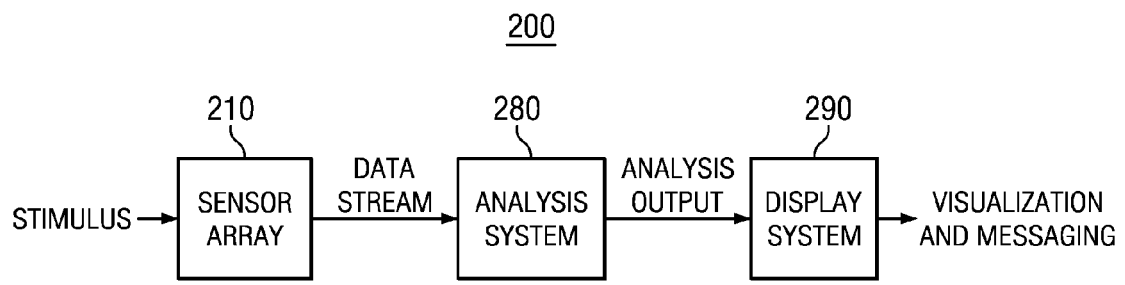
FIG. 2A illustrates an example data flow in a sensor network.

FIG. 2A illustrates an example data flow in a sensor network. In various embodiments, one or more sensors in a sensor array 210 may receive one or more stimuli. The sensor array 210 may transmit one or more data streams based on the one or more stimuli to one or more analysis systems 280 over any suitable network. As an example and not by way of limitation, one sensor could transmit multiple data streams to multiple analysis systems. As another example and not by way of limitation, multiple sensors could transmit multiple data streams to one analysis system.

In particular embodiments, the sensors in sensor array 210 each produce their own data stream, which is transmitted to analysis system 280. In other embodiments, one or more sensors in sensor array 210 have their output combined into a single data stream.

Analysis system 280 may monitor, store, and analyze one or more data streams. Analysis system 280 may be local, remote, or both. Analysis system 280 may transmit one or more analysis outputs based on the one or more data streams to one or more display systems 290. As an example and not by way of limitation, one analysis system could transmit multiple analysis outputs to multiple display systems. As another example and not by way of limitation, multiple analysis systems could transmit multiple analysis outputs to one display system. Analysis system 280 may also store one or more analysis outputs for later processing.

A display system 290 may render, visualize, display, message, and publish to one or more users based on the one or more analysis outputs. A display system 290 may be local, remote, or both. In various embodiments, a sensor array 210 may transmit one or more data streams directly to a display system 290. This may allow, for example, display of stimulus readings by the sensor.

Although FIG. 2A illustrates a particular arrangement of sensor array 210, analysis system 280, and display system 290, this disclosure contemplates any suitable arrangement of sensor array 210, analysis system 280, and display system 290. Moreover, although FIG. 2A illustrates a particular data flow between sensor array 210, analysis system 280, and display system 290, this disclosure contemplates any suitable data flow between sensor array 210, analysis system 280, and display system 290.

Sensors

Figure 2B:
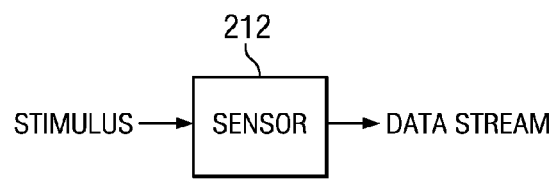
FIG. 2B illustrates an example sensor.

FIG. 2B illustrates an example sensor 212 and data flow to and from the sensor. A sensor 212 is a device which receives and responds to a stimulus. Here, the term "stimulus" means any signal, property, measurement, or quantity that may be detected and measured by a sensor 212.

In particular embodiments, a sensor 212 receives stimuli from a subject. As an example and not by way of limitation, a subject may be a person (or group of persons or entity), place (such as, for example, a geographical location), or thing (such as, for example, a building, road, airplane, or automobile). Although this disclosure describes particular types of subjects, this disclosure contemplates any suitable types of subjects. In particular embodiments, one or more subjects of one or more sensors 112 may be a user of other components of sensor network 100, such as other sensors 112, analysis system 180, or display system 190. As such, the terms "subject" and "user" may refer to the same person, unless context suggests otherwise.

A sensor 212 responds to a stimulus by generating a data stream corresponding to the stimulus. A data stream may be a digital or analog signal that can be transmitted over any suitable transmission medium and further used in electronic devices. As used herein, the term "sensor" is used broadly to describe any device that receives a stimulus and converts it into a data stream. The present disclosure assumes that the data stream output from a sensor 212 is transmitted to an analysis system, unless otherwise specified.

In particular embodiments, one or more sensors 212 each include a stimulus receiving element (i.e., sensing element), a communication element, and any associate circuitry. Sensors 212 generally are small, battery powered, portable, and equipped with a microprocessor, internal memory for data storage, and a transducer or other component for receiving stimulus. However, a sensor 212 may also be an assay, test, or measurement. A sensor 212 may interface with a personal computer and utilize software to activate the sensor 212 and to view and analyze the collected data. A sensor 212 may also have a local interface device (e.g., keypad, LCD) allowing it to be used as a stand-alone device. In particular embodiments, a sensor 212 may include one or more communication elements that may receive or transmit information (such as data streams) over a communication channel, for example to one or more other components in a sensor network.

In particular embodiments, one or more sensors 212 may measure a variety of things, including physiological, psychological, behavioral, and environmental stimulus. Physiological stimulus may include, for example, physical aspects of a person (e.g., stretch, motion of the person, and position of appendages); metabolic aspects of a person (e.g., glucose level, oxygen level, osmolality), biochemical aspects of a person (e.g., enzymes, hormones, neurotransmitters, cytokines), and other aspects of a person related to physical health, disease, and homeostasis. Psychological stimulus may include, for example, emotion, mood, feeling, anxiety, stress, depression, and other psychological or mental states of a person. Behavioral stimulus may include, for example, behavior related a person (e.g., working, socializing, arguing, drinking, resting, driving), behavior related to a group (e.g., marches, protests, mob behavior), and other aspects related to behavior. Environmental stimulus may include, for example, physical aspects of the environment (e.g., light, motion, temperature, magnetic fields, gravity, humidity, vibration, pressure, electrical fields, sound, GPS location), environmental molecules (e.g., toxins, nutrients, pheromones), environmental conditions (e.g., pollen count, weather), other external condition (e.g., traffic conditions, stock market information, news feeds), and other aspects of the environment.

As an example and not by way of limitation, particular embodiments may include one or more of the following types of sensors 212: Accelerometer; Affinity electrophoresis; Air flow meter; Air speed indicator; Alarm sensor; Altimeter; Ammeter; Anemometer; Arterial blood gas sensor; Attitude indicator; Barograph; Barometer; Biosensor; Bolometer; Boost gauge; Bourdon gauge; Breathalyzer; Calorie Intake Monitor; calorimeter; Capacitive displacement sensor; Capillary electrophoresis; Carbon dioxide sensor; Carbon monoxide detector; Catalytic bead sensor; Charge-coupled device; Chemical field-effect transistor; Chromatograph; Colorimeter; Compass; Contact image sensor; Current sensor; Depth gauge; DNA microarray; Electrocardiograph (ECG or EKG); Electrochemical gas sensor; Electrolyte-insulator-semiconductor sensor; Electromyograph (EMG); Electronic nose; Electro-optical sensor; Exhaust gas temperature gauge; Fiber optic sensors; Flame detector; Flow sensor; Fluxgate compass; Foot switches; Force sensor; Free fall sensor; Galvanic skin response sensor; Galvanometer; Gardon gauge; Gas detector; Gas meter; Geiger counter; Geophone; Goniometers; Gravimeter; Gyroscope; Hall effect sensor; Hall probe; Heart-rate sensor; Heat flux sensor; High-performance liquid chromatograph (HPLC); Hot filament ionization gauge; Hydrogen sensor; Hydrogen sulfide sensor; Hydrophone; Immunoassay, Inclinometer; Inertial reference unit; Infrared point sensor; Infra-red sensor; Infrared thermometer; Insulin monitors; Ionization gauge; Ion-selective electrode; Keyboard; Kinesthetic sensors; Laser rangefinder; Leaf electroscope; LED light sensor; Linear encoder; Linear variable differential transformer (LVDT); Liquid capacitive inclinometers; Magnetic anomaly detector; Magnetic compass; Magnetometer; Mass flow sensor; McLeod gauge; Metal detector; MHD sensor; Microbolometer; Microphone; Microwave chemistry sensor; Microwave radiometer; Mood sensor; Motion detector; Mouse; Multimeter; Net radiometer; Neutron detection; Nichols radiometer; Nitrogen oxide sensor; Nondispersive infrared sensor; Occupancy sensor; Odometer; Ohmmeter; Olfactometer; Optode; Oscillating U-tube; Oxygen sensor; Pain sensor; Particle detector; Passive infrared sensor; Pedometer; Pellistor; pH glass electrode; Photoplethysmograph; Photodetector; Photodiode; Photoelectric sensor; Photoionization detector; Photomultiplier; Photoresistor; Photoswitch; Phototransistor; Phototube; Piezoelectric accelerometer; Pirani gauge; Position sensor; Potentiometric sensor; Pressure gauge; Pressure sensor; Proximity sensor; Psychrometer; Pulse oximetry sensor; Pulse wave velocity monitor; Radio direction finder; Rain gauge; Rain sensor; Redox electrode; Reed switch; Resistance temperature detector; Resistance thermometer; Respiration sensor; Ring laser gyroscope; Rotary encoder; Rotary variable differential transformer; Scintillometer; Seismometer; Selsyn; Shack-Hartmann; Silicon bandgap temperature sensor; Smoke detector; Snow gauge; Soil moisture sensor; Speech monitor; Speed sensor; Stream gauge; Stud finder; Sudden Motion Sensor; Tachometer; Tactile sensor; Temperature gauge; Thermistor; Thermocouple; Thermometer; Tide gauge; Tilt sensor; Time pressure gauge; Touch switch; Triangulation sensor; Turn coordinator; Ultrasonic thickness gauge; Variometer; Vibrating structure gyroscope; Voltmeter; Water meter; Watt-hour meter; Wavefront sensor; Wired glove.; Yaw rate sensor; and Zinc oxide nanorod sensor. Although this disclosure describes particular types of sensors, this disclosure contemplates any suitable types of sensors.

A biosensor is a type of sensor 112 that receives a biological stimulus and converts it into a data stream. As used herein, the term "biosensor" is used broadly.

In particular embodiments, a biosensor may be a device for the detection of an analyte. An analyte is a substance or chemical constituent that is determined in an analytical procedure. For instance, in an immunoassay, the analyte may be the ligand or the binder, while in blood glucose testing, the analyte is glucose. In medicine, analyte typically refers to the type of test being run on a patient, as the test is usually determining the existence and/or concentration of a chemical substance in the human body.

A common example of a commercial biosensor is a blood glucose monitor, which uses the enzyme glucose oxidase to break blood glucose down. In doing so, it first oxidizes glucose and uses two electrons to reduce the FAD (flavin adenine dinucleotide, a component of the enzyme) to $FADH_2$ (1,5-dihydro-FAD). This in turn is oxidized by the electrode (accepting two electrons from the electrode) in a number of steps. The resulting current is a measure of the concentration of glucose. In this case, the electrode is the transducer and the enzyme is the biologically active component.

In particular embodiments, a biosensor combines a biological component with a physicochemical detector component. A typical biosensor comprises: a sensitive biological element (e.g., biological material (tissue, microorganisms, organelles, cell receptors, enzymes, antibodies, nucleic acids, etc.), biologically derived material, biomimic); a physicochemical transducer/detector element (e.g. optical, piezoelectric, electrochemical) that transforms the signal (i.e. input stimulus) resulting from the interaction of the analyte with the biological element into another signal (i.e. transducers) that may be measured and quantified; and associated electronics or signal processors generating and transmitting a data stream corresponding to the input stimulus. The encapsulation of the biological component in a biosensor may be done by means of a semi-permeable barrier (e.g., a dialysis membrane or hydrogel), a 3D polymer matrix (e.g., by physically or chemically constraining the sensing macromolecule), or by other means.

In particular embodiments, a sensor 112 may sample input stimulus at discrete times. The sampling rate, sample rate, or sampling frequency defines the number of samples per second (or per other unit) taken from a continuous or semi-continuous stimulus to make a discrete data signal. For time-domain signals, the unit for sampling rate may be 1/s (Hertz). The inverse of the sampling frequency is the sampling period or sampling interval, which is the time between samples. The sampling rate of a sensor 112 may be controlled locally, remotely, or both.

In particular embodiments, one or more sensors 112 in the sensor array 110 may have a dynamic sampling rate. Dynamic sampling is performed when a decision to change the sampling rate is taken if the current outcome of a process is within or different from some specified value or range of values. As an example and not by way of limitation, if the stimulus is different from the outcome predicted by some model or falls outside some threshold range, the sensor 112 may increase or decrease its sampling rate in response. Dynamic sampling may be used to optimize the operation of the sensors 112 or influence the operation of actuators to change the environment.

In particular embodiments, the sampling rate of a sensor 112 may be based on receipt of a particular stimulus. As an example and not by way of limitation, an accelerometer may have a default sample rate of 1/s, but may increase its sampling rate to 60/s whenever it measures a non-zero value, and then may return to a 1/s sampling rate after getting 60 consecutive samples equal to zero. As another example and not by way of limitation, if the stimulus measured over a particular range of time does vary significantly, the sensor 112 may reduce its sampling rate.

In particular embodiments, the sampling rate of a sensor 112 may be based on input from one or more components of sensor network 100. As an example and not by way of limitation, a heart rate monitor may have a default sampling rate of 1/min, but may increase the its sampling rate in response to a signal or instruction from analysis system 180.

In particular embodiments, one or more sensors 112 in the sensor array 110 may increase or decrease the precision at which the sensors 112 sample input. As an example and not by way of limitation, a glucose monitor may use four bits to record a user's blood glucose level by default. However, if the user's blood glucose level begins varying quickly, the glucose monitor may increase its precision to eight-bit measurements.

In particular embodiments, the stimulus received by a sensor 112 may be input from a subject (i.e., the user of the sensor). A subject may provide input in a variety of ways. User-input may include, for example, inputting a quantity or value into the sensor, speaking or providing other audio input to the sensor, and touching or providing other stimulus to the sensor. Any client system with a suitable I/O device may serve as a user-input sensor. Suitable I/O devices include alphanumeric keyboards, numeric keypads, touch pads, touch screens, input keys, buttons, switches, microphones, pointing devices, navigation buttons, stylus, scroll dial, another suitable I/O device, or a combination of two or more of these.

In particular embodiments, a sensor 112 may query the subject to input information into the sensor 112. In one embodiment, the sensor 112 may query the subject at static intervals (e.g., every hour). In another embodiment, the sensor 112 may query the subject at a dynamic rate. The dynamic rate may be based on a variety of factors, including prior input into the sensor 112, data from other sensors 112 in sensor array 110, output from analysis system 180, etc. As an example and not by way of limitation, if a heart-rate monitor in sensor array 110 indicates an increase in the subject's heart-rate, a user-input sensor may immediately query the subject to input his current activity.

In particular embodiments, a sensor 112 may be a data feed. A data feed may be a computing system that receives and aggregates physiological, psychological, behavioral, or environmental data from one or more sources and transmits one or more data streams based on the aggregated data. Alternatively, a data feed may be the one or more data streams based on the aggregated data. As an example and not by way of limitation, data feeds may be stock-market tickers, weather reports, news feeds, traffic-condition updates, public-health notices, electronic calendars, data from one or more other users (such as, for example, physiological, psychological, or behavioral data from another user), or any other suitable data feeds. A data feed may contain both personal and remote data, as discussed previously. A data feed may be any suitable computing device (such as, for example, computer system 1700).

The example data feeds illustrated and described herein are provided for illustration purposes only and are not meant to be limiting. This disclosure contemplates the use of any suitable data feed.

Data Streams

In particular embodiments, a data stream comprises one or more data transmitted from one or more sensors 112 in sensor array 110. A data stream may be a digital or analog signal that may be transmitted over any suitable transmission medium and further used in electronic devices. Sensor array 110 may transmit one or more data streams based on one or more stimuli to one or more analysis systems 180 over any suitable network.

A data stream may include signals from a variety of types of sensors 112, including physiological, psychological, behavioral, and environmental sensors. A sensor 112 generates a data stream corresponding to the stimulus it receives. As an example and not by way of limitation, a physiological sensor (e.g., an accelerometer) generates a physiological data stream (e.g., an accelerometer data stream, which includes, for example, data on the acceleration of a subject over time).

Sensor data may include any suitable information. In particular embodiments, sensor data includes measurements taken by one or more sensors 112. Sensor data may include samples that may have any suitable format. In particular embodiments, the format of the samples may be a tuple (or ordered set) that has one or more data parameters, and a particular sample may be a tuple of one or more values for the one or more data parameters. As an example and not by way of limitation, a tuple format (t, p) may have data parameters time t and pressure p, and a particular sample (t0, p0) may have values pressure p0 measured at time t0. The tuple format may include any suitable data parameters, such as one or more sensor parameters and/or one or more test parameters. A sensor parameter may correspond to one or more sensors 112, and a sensor value may record one or more measurements taken by one or more sensors 112. As an example and not by way of limitation, a sensor value may record a measurement taken by a sensor 112. A test parameter may correspond to a factor that describes a temporal, spatial, and/or environmental feature of a measurement process, and a test value may record the value of the feature when the measurements are taken. As an example and not by way of limitation, the parameter may be time and the parameter value may record a particular time at which measurements are taken.

In particular embodiments, a sensor 112 may transmit one or more data at discrete times. The transmitting rate, transmission rate, or transmitting frequency defines the number of transmissions per second (or per other unit) sent by a sensor to make a discrete data signal. For time-domain signals, the unit for transmitting rate may be 1/s (Hertz). The inverse of the transmitting frequency is the transmitting period or transmitting interval, which is the time between transmissions. The datum may be transmitted continuously, periodically, randomly, or with any other suitable frequency or period. This may or may not correlate with the sampling rate of the sensor.

Reference to sensor data may encompass a sensor data stream, and vice versa, where appropriate. Sensor data may relate to a sensor subject, wherein the sensor 112 receives stimulus from or related to the subject. Sensor data or a data stream may relate to a sensor subject in any suitable way. As an example and not by way of limitation, sensor data may relate to a sensor subject because one or more sensors 112 generated the sensor data from one or more stimuli produced by the sensor subject. As another example and not by way of limitation, sensor data may relate to a sensor subject because the sensor data may provide insight or further understanding of the sensor subject. As yet another example and not by way of limitation, sensor data may relate to a sensor subject because it may help detect or predict the occurrence of one or more problems or events concerning the sensor subject. As yet another example and not by way of limitation, sensor data may relate to a sensor subject because it may facilitate monitoring of the sensor subject.

In particular embodiments, the components of sensor network 100 may utilize some type of data acquisition system to further process the data stream signal for use by analysis system 180. As an example and not by way of limitation, a data acquisition system may convert an analog waveforms signal into a digital value. As another example and not by way of limitation, the data acquisition system may convert decimal values into binary values. The data acquisition system may be local, for example, integrated into a sensor 112 in sensor array 110 or into local analysis system 120. The data acquisition system may also be remote, for example, integrated into remote analysis system 150 or an independent system.

In particular embodiments, the data acquisition system may perform one or more signal conditioning processes (for example, if a signal from a sensor 112 is not suitable for the type of analysis system 180 being used). As an example and not by way of limitation, the data acquisition system may amplify, filter, or demodulate the signal. Various other examples of signal conditioning might be bridge completion, providing current or voltage excitation to the sensor, isolation, time-base correction, and linearization. In particular embodiments, single-ended analog signals may be converted to differential signals. In particular embodiments, digital signals may be encoded to reduce and correct transmission errors or downsampled to reduce transmission power requirements.

In particular embodiments, the components of sensor network 100 may utilize some type of data logging system to record, categorize, store, and file data from one or more data streams over time. The data logging system may be local, for example, integrated into a sensor 112 in sensor array 110 or into local analysis system 120. The data logging system may also be remote, for example, integrated into remote analysis system 150 or an independent system. The data logging system may also use distributed resources to record data. The data logging system may store data on any suitable data store, such as, for example, data store 1840.

The data logging system may record data streams as one or more data sets. A data set comprises one or more data from a data stream. Data sets may be categorized and formed based on a variety of criteria. As an example and not by way of limitation, a data stream could be recorded as one or more data sets based on the specific subject, sensor, time period, event, or other criteria.

In particular embodiments, one or more data sets from a data stream may be used to construct a binary decision diagram (BDD) representing the data sets.

Binary Decision Diagrams

A binary decision diagram is a data structure that may be used to represent a Boolean function. A BDD may be graphically represented as a rooted, directed, and acyclic graph having one or more internal decision nodes and two terminal nodes. Each decision node represents a different variable of the Boolean function, and is typically denoted as a circle in the graph. The two terminal nodes, a 0 terminal node and a 1 terminal node, are typically denoted as a square each in the graph. Each decision node has two edges, a 0 edge, typically denoted as a dash line or a dotted line in the graph, and a 1 edge, typically denoted as a solid line in the graph. Each edge may be connected to another decision node or to one of the terminal nodes.

Each path in the graph may by formed by one or more decision nodes and their associated edges, and eventually leads to either the 0 terminal node or the 1 terminal node. The decision nodes that form a particular path each represent a different variable of the Boolean function. That is, along a single path, no two decision nodes represent the same variable. A path that leads to the 0 terminal node indicates that the Boolean function evaluates to FALSE for the values assigned to the variables represented by the decision nodes on the path, and a path that leads to the 1 terminal node indicates that the Boolean function evaluates to TRUE for the values assigned to the variables represented by the decision nodes on the path.

Figure 3A:
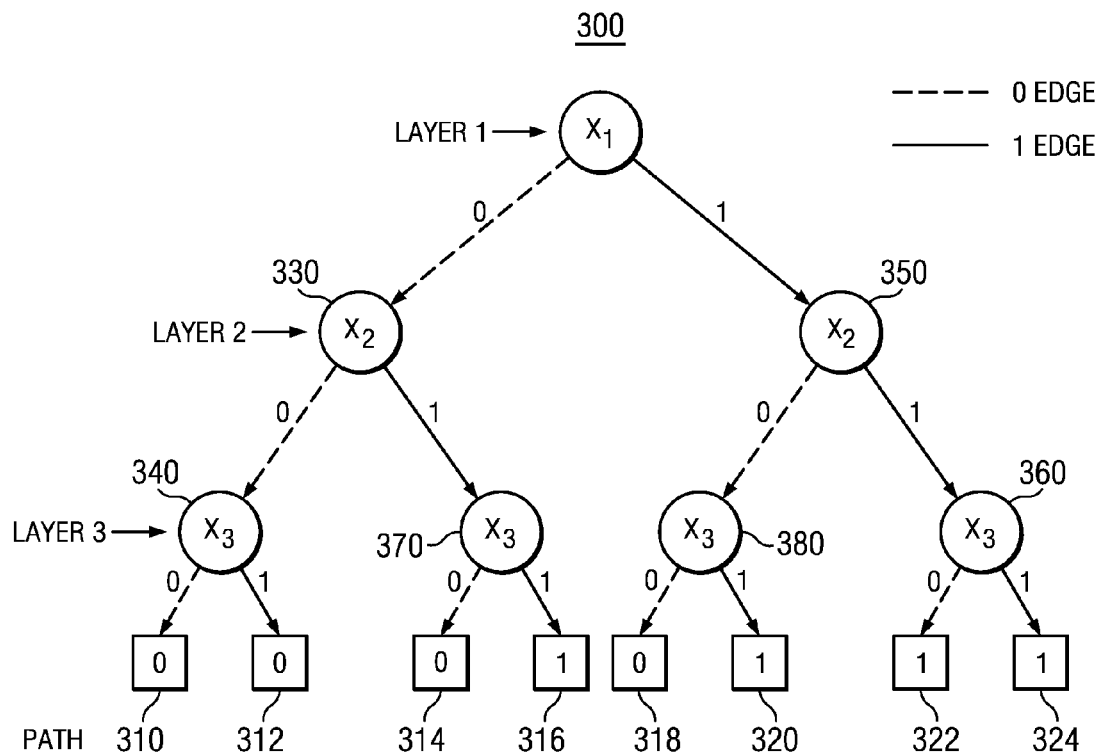
FIG. 3A illustrates a BDD that represents a Boolean function that has three variables.

FIG. 3A illustrates an example BDD 300 that represents a Boolean function having three variables: $x_1$, $x_2$, and $x_3$. Since the Boolean function represented by BDD 300 has three variables, BDD 300 has at most three decision-node layers, layers 1, 2, and 3. That is, there are at most three layers in BDD 300 that each have at least one decision node. The decision node that represents variable $x_1$ is at layer 1 of BDD 300; the decision nodes that represent variable $x_2$ are at layer 2 of BDD 300; and the decision nodes that represent variable $x_3$ are at layer 3 of BDD 300. Each path in BDD 100, formed by the decision nodes and their associated edges, leads to either the 0 terminal node or the 1 terminal node, indicating that the Boolean function evaluates to FALSE or TRUE, respectively. Note that for readability, the 0 terminal node and the 1 terminal node are duplicated multiple times in FIG. 3A.

A minterm is a logical expression of n variables that employs only the complement operator and the conjunction operator. For a Boolean function of n variables, a minterm is a product term in which each of the n variables appears once, either in a complemented or uncomplemented form. In particular embodiments, each datum from a data set may be represented as a minterm to yield a set of minterms. A characteristic function may be generated from the minterms, the characteristic function indicating whether a given minterm is a member of the set of minterms.

In particular embodiments, a characteristic function $f^S(\vec{x})=1$ of a data set S indicates whether a given element (represented by a minterm) is a member of the data set S. As an example and not by way of limitation, a data set from a data stream may be characterized by the Boolean function $f^S(\vec{x})$ of a data set $S \subset N$, such that $f^S(\vec{x})=1$ if and only if $\vec{x}$ is the binary representation of an element of data set S. For example, for S={1,3}, $f(0,0)=f(1,0)=0$ and $f(0,1)=f(1,1)=1$. Similarly, a plurality of data streams from a plurality of sensors may also be characterized by a Boolean function. The data set may comprise a set of tuples of the form $S=\{(t_i, s_i^1, \ldots, s_i^k)\}$, where $s_i^j$ is the input from sensor j at time instance i. The corresponding Boolean function would be $f^S(\vec{t}_i; \vec{s}_i^1; \ldots; \vec{s}_i^k)$. As an example and not by way of limitation, sensor array 110 may comprise sensor A and sensor B. The data streams from sensors A and B may be characterized by the Boolean functions $f_A(t_1,t_2,x_1,x_2,x_3)$ and $f_B(t_1, t_2, x_4, x_5, x_6)$, respectively, where:

($t_1$,$t_2$) is a time associated with a sensor measurement,
($x_1$,$x_2$,$x_3$) is a measurement by sensor A at a given time, and
($x_4$,$x_5$,$x_6$) is a measurement by sensor B at a given time.

The Boolean functions $f_A$ and $f_B$ may be represented by two BDDs, such as $BDD_A$ and $BDD_B$, respectively. Alternatively, the data streams from sensors A and B may be characterized by a single Boolean function $f_A(t_1,t_2,x_1,x_2,x_3,x_4,x_5,x_6)$, which may be represented by a single BDD, such as $BDD_{AB}$.

Figure 3B:
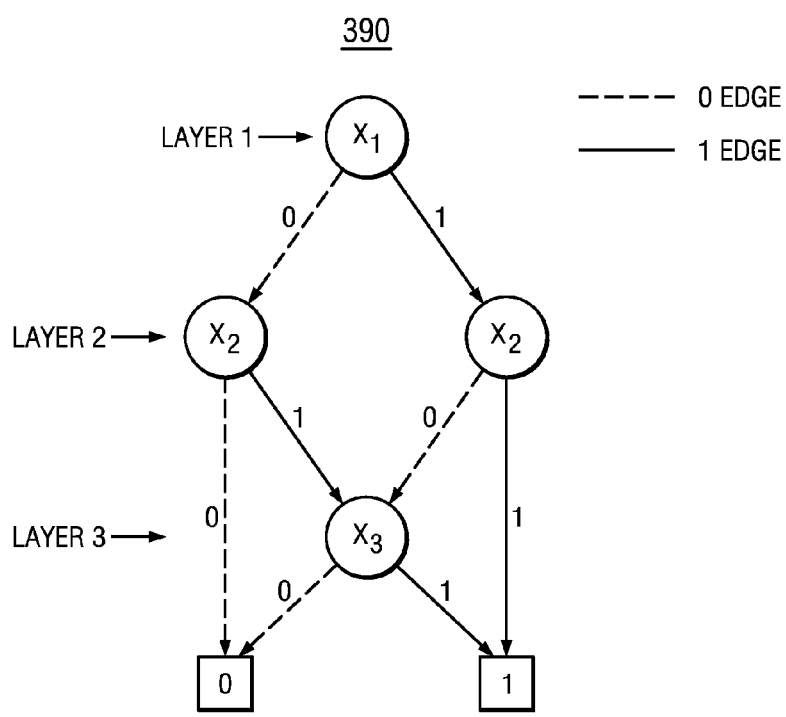
FIG. 3B illustrates an optimized BDD that represents a Boolean function that has three variables.

BDD 300 is not the most optimized representation of the Boolean function as some of the nodes in BDD 300 are redundant and portions of BDD 300 are isomorphic. For example, consider paths 310 and 312, both of which end at the 0 terminal node. By examining the decision nodes on paths 310 and 320, it may be determined that as long as decision node 330, which represents variable $x_2$, branches along its 0 edge, the Boolean function evaluates to FALSE, regardless of along which branch decision node 340, which represents variable $x_3$, proceeds. Thus, decision node 340 may be replaced by the 0 terminal node. Similarly, paths 322 and 324 end at the 1 terminal node. By examining the decision nodes on these two paths, it may be determined that as long as decision node 350, which represents variable $x_2$, branches along its 1 edge, the Boolean function evaluates to TRUE, regardless of along which branches decision node 360, which represents variable $x_3$, proceeds. Thus, decision node 360 may be replaced by the 1 terminal node. As another example, consider decision nodes 370 and 380, which both represent variable $x_3$. Decision nodes 370 and 380 both have their 0 edge leading to the 0 terminal node and their 1 edge leading to the 1 terminal node. Therefore, they are duplicates or isomorphic to each other. Thus, one of them may be removed from BDD 300. FIG. 3B illustrates an example BDD 390 representing the same Boolean function as repressed by BDD 300, but is more optimized than BDD 300 because it uses fewer nodes to represent the same Boolean function as a result of removing the redundant decision nodes and the isomorphic portions of BDD 300.

A BDD whose redundant decision nodes and isomorphic sub-graphs have been removed and whose decision nodes appear in the same order from the root to the terminal nodes along all the paths in the BDD is referred to as a reduced ordered binary decision diagram (ROBDD). The advantage of a ROBDD is that it is canonical for a particular function and variable order, which makes it useful in various types of practical applications, such as in functional equivalence checking and functional technology mapping.

A ROBDD has two important properties. First, the ROBDD is ordered. That is, there is a fixed order $\pi\{1, \ldots, n\} \rightarrow \{x_1, \ldots, x_n\}$ such that for any non-terminal node v, index(low(v))=$\pi$(k) with k>$\pi^{-1}$ (index(v)) and index(high (v))=$\pi$(q) with q>$\pi^{-1}$ (index(v)) hold if low(v) and high(v) are also non-terminal nodes, where index(v) denotes the index of the variable associated with node v, low(v) corresponds to the case where the variable associated with node v is assigned 0, and high(v) corresponds to the case where the variable associated with node v is assigned 1. Second, the ROBDD is reduced. That is, there exists no non-terminal node v∈V with low(v)=high(v) and there are no two non-terminal nodes v and v' such that the sub-BDDs rooted by v and v' are isomorphic. Note that a non-terminal node is a decision node. For example, in FIG. 3B, BDD 390 has three layers as it represents a Boolean function having three variables. Since BDD 390 is ordered, each layer contains the decision nodes that correspond to a particular variable. For example, layer 2 contains the decision nodes corresponding to variable $x_2$ only, and does not contain any decision node corresponding to another variable (e.g., $x_1$ or $x_3$).

In additional to BDDs and ROBDDs, other examples of BDDs include partitioned ordered binary decision diagrams (POBDDs), zero-suppressed decision diagrams (ZDDs), nano binary decision diagrams (nanoDDs), zero-suppressed nano binary decision diagrams (nanoZDDs), or other suitable binary decision diagrams. Although this disclosure discusses using particular BDDs in particular, this disclosure contemplates using any suitable type of BDD in any suitable applications.

BDDs have many practical applications, and the various algorithms disclosed in the present disclosure may be used with BDDs of any applications. As an example and not by way of limitation, in the field integrated circuit (IC) design, an IC may be used to implement a function, which may be represented by a BDD. Sometimes, a property that an IC design needs to satisfy may be represented by a BDD, which may then be used with in connection with formally verifying the design of the circuit. In the field of healthcare, BDDs may be used to represent data collected by medical sensors. A BDD, or more specifically, the data that forms the BDD, may be stored in a computer-readable non-transitory storage medium. When the variables of the BDD are processed using any of the algorithms described in this disclosure, the data is transformed as embodied by the computer-readable non-transitory storage medium.

In particular embodiments, any set of integers may be represented as a Boolean function, and the Boolean function may be represented by a BDD. Given a set of integers, particular embodiments may determine the minimum number of bits required to represent the largest integer in the set. This number of bits is the number of variables of the Boolean function. Then, for each integer in the set the Boolean function evaluates to TRUE, and for any integer not in the set the Boolean function evaluates to FALSE.

In particular embodiments, a BDD may be used to represent one or more data sets from one or more data streams. Each path in the BDD that leads to the 1 terminal node indicates that the value (i.e., the data point) represented by all the decision nodes along that path belongs to the data set. Similarly, each path in the BDD that leads to the 0 terminal node indicates that the value represented by all the decision nodes along that path is not included in the data set.

To represent a data set using a BDD, the minimum number of variables needed for the BDD equals the minimum number of bits needed to represent the largest value (i.e., data point) in the data set. As an example and not by way of limitation, consider a data set comprising a set of integers, {3, 5, 6, 7}. The largest integer in the set is 7, which requires 3 bits. Thus, the Boolean function used to represent this set of integers requires three variables $x_1$, $x_2$, and $x_3$. The following table illustrates the values of the three variables and the Boolean function as they are used to represent {3, 5, 6, 7}:

| Decimal Value | Binary Value $x_1, x_2, x_3$ | $f(x_1, x_2, x_3)$ |
| --- | --- | --- |
| 0 | 0 0 0 | 0 |
| 1 | 0 0 1 | 0 |
| 2 | 0 1 0 | 0 |
| 3 | 0 1 1 | 1 |
| 4 | 1 0 0 | 0 |
| 5 | 1 0 1 | 1 |
| 6 | 1 1 0 | 1 |
| 7 | 1 1 1 | 1 |

The function $f(x_1,x_2,x_3)$ may be represented by BDD 300 illustrated in FIG. 3A or BDD 390 illustrated in FIG. 3B.

In particular embodiments, one or more components of sensor network 100 may store one or more BDDs in a BDD library. The BDD library may include any suitable information about a BDD, such as, for example, node structure, each binary variable, indices to the nodes that correspond to the two possible evaluations of the variables, complementation of the indices, or other suitable information about the BDD. In particular embodiments, the BDD library may store the information compactly. As an example and not by way of limitation, a BDD library may maintain the indices and variable identifiers as a function of the size of the BDD. The BDD may have at most k nodes throughout some or all manipulations performed by BDD library. Each node of the BDD may be labeled with one of at most v variable identifiers. The indices to nodes therefore require at most $\lceil \log(v) \rceil$ bits to index any variable. The node therefore requires only $2 \cdot \lceil \log(k) \rceil + \lceil \log(v) \rceil$ bits. In addition, two bits may be reserved, one bit used to identify complemented edges (allowing the representation of a function as well as its negation by a single node) and another bit used as a general mark bit used during garbage collection. Values for v and k may be determined in any suitable manner. For example, a user may specify v and a default k value may be used initially. When the address space allowed by the default k value is exhausted, the k value may be increased and the node table may be rebuilt. In another example, maximum values for v and k may be assumed.

In particular embodiments, one or more components of sensor network 100 may store sensor data as one or more BDDs. One or more sensors 112 in sensor array 110 may take a plurality of samples (i.e., receive a plurality of stimuli) and produce a data set S based on the samples. In particular embodiments, each sample comprises a tuple of one or more sensor values. Each sensor value records one or more stimuli received by one or more sensors. Data set S may be generated in any suitable manner. In particular embodiments, time may be quantized according to the sampling frequency of the sensor 112 or for desired accuracy. For each time t, set S of sensor values is obtained to yield $S=\{(t_i, q_i^1, \ldots, q_i^k)\}$, where $q_i^j$ is the quantized input from sensor j at time instance i. Each sample is represented as a minterm. In particular embodiments, one or more variables may be allocated to each data value of a sample. As an example and not by way of limitation, Nt variables may be allocated for time, Ns1 variables may be allocated for a first sensor, and Ns2 variables may be allocated for a second sensor. Therefore, a sample would correspond to a minterm of the form $t_1 \ldots t_{Nt} \cdot s_1^1 \ldots s_{Ns1}^1 \cdot s_1^2 \ldots s_{Ns2}^2$. For example, if Nt=16, Ns1=8, and Ns2=8, then a sample would correspond to a minterm of the form $t_1 \ldots t_{16} \cdot s_1^1 \ldots s_8^1 \cdot s_1^2 \ldots s_8^2$. Each sensor sample may be expressed as a binary number using the allocated variables. In the example, a subset of S may be {(1,70,3), (2,70,3), (3,70,4)}. The related minterms are:

0000000000000001·01000110·00000011,
0000000000000010·01000110·00000011,
0000000000000011·01000110·00000100.

In particular embodiments, a characteristic function $f^S$ may be generated from a set of minterms. The characteristic function $f^S$ may be generated in any suitable manner. As an example and not by way of limitation, a logical operation may be applied to the minterms to generate characteristic function $f^S$. This disclosure contemplates any generating characteristic functions using suitable logical operations. As an example and not by way of limitation, a logical operation may include AND, OR, XOR, NOT, or a combination of two or more of these. Applying a logical OR operation to a number of operands yields the logical OR of the operands. The corresponding characteristic function $f^S(\vec{t}; \vec{s}^1; \vec{s}^2)$ is the logical OR of all minterms. A characteristic function $f^S$ may be updated to include additional data sets in any suitable manner. As an example and not by way of limitation, a new data set may be represented as a new set of minterms, and a logical OR operation may be applied to the characteristic function $f^S$ and the new set of minterms to yield an updated characteristic function $f^S$.

A characteristic function $f^S$ may be reported in any suitable manner. As an example and not by way of limitation, display system 190 may facilitate display of characteristic function $f^S$ at a suitable I/O device.

Analysis

Analysis system 180 may monitor, store, and analyze one or more data streams from one or more sensors 112 in sensor array 110. A data stream from a sensor 112 may be transmitted to analysis system 180 over any suitable medium. Analysis system 180 may transmit one or more analysis outputs based on the one or more data streams to one or more other components of sensor network 100, such as, for example, sensors 112, other analysis systems 180, or display systems 190. Analysis system 180 may be any suitable computing device, such as, for example, computer system 1700.

In particular embodiments, analysis system 180 may comprise one or more local analysis systems 120 or one or more remote analysis systems 150. Where analysis system 180 comprises multiple subsystems (e.g., local analysis system 120 and remote analysis system 150), processing and analysis of the data streams may occur in series or in parallel. As an example and not by way of limitation, analysis system 180 may receive identical data streams from a sensor 112 at both local analysis system 120 and remote analysis system 150. As another example and not by way of limitation, analysis system 180 may receive a data stream at local analysis system 120, which may process the data stream and then transmit a modified data stream/analysis output to remote analysis system 150.

In particular embodiments, analysis system 180 may access and analyze one or more data sets from a data stream. Analysis system 180 may analyze a data stream in real-time as it is received from sensor array 110, or it may store the data stream after it is received from sensor array 110 for subsequently processing the data stream. Analysis system 180 may use any suitable process, calculation, or technique to analyze a data stream. As an example and not by way of limitation, analysis system 180 may perform a variety of processes and calculations, including ranging, inspecting, cleaning, filtering, transforming, modeling, normalizing, averaging, annotating, correlating, or contextualizing data. As another example and not by way of limitation, analysis system 180 may use a variety of data analysis techniques, including data mining, data fusion, distributed database processing, or artificial intelligence. These techniques may be applied to analyze various data streams and to generate correlations and conclusions based on the data. Analysis system 180 may analyze a plurality of data streams to determine if the data streams are related. A relationship between data streams may include, for example, correlations, causal relationships, dependent relationships, reciprocal relationships, data equivalence, another suitable relationship, or two or more such relationship. In particular embodiments, analysis system 180 may access or generate one or more BDDs representing one or more data streams and perform a variety of processes and calculations on the BDDs. Although this disclosure describes analysis system 180 performing particular analytical processes using particular techniques, this disclosure contemplates analysis system 180 performing any suitable analytical processes using any suitable techniques.

In particular embodiments, analysis system 180 may generate models based on one or more data streams. A model is a means for describing a system or object. As an example and not by way of limitation, a model may be a data set, function, algorithm, differential equation, chart, table, decision tree, binary decision diagram, simulation, another suitable model, or two or more such models. A model may describe a variety of systems or objects, including one or more aspects of one or more persons' physiology, psychology, behavior, or environment. Although this disclosure describes particular components generating particular models, this disclosure contemplates any suitable components generating any suitable models. Moreover, although this disclosure describes generating particular models using particular techniques, this disclosure contemplates generating any suitable models using any suitable techniques.

Analysis system 180 may generate models that are empirical, theoretical, linear, nonlinear, deterministic, probabilistic, static, dynamic, heterogeneous, or homogenous. Analysis system 180 may generate models that fit one or more data points using a variety of techniques, including, for example, curve fitting, model training, interpolation, extrapolation, statistical modeling, nonparametric statistics, differential equations, etc.

Analysis system 180 may generate models of various types, including baseline models, statistical models, predictive models, etc. A baseline model is a model that serves as a basis for comparison, and is typically generated using controlled data (i.e., baseline data) over a specified period (i.e., a control period). The control period may be any suitable period. As an example and not by way of limitation, a baseline model of a subject's blood pressure may simply be the subject's average blood pressure calculated from a series of blood-pressure measurements taken over the course of a week by a blood-pressure monitor. A predictive model is a mathematical function (or set of functions) that describe the behavior of a system or object in terms of one or more independent variables. As an example and not by way of limitation, a predictive model that may be used to calculate a physiological state based on one or more actual sensor measurements. A type of predictive model is a statistical model, which is a mathematical function (or set of functions) that describe the behavior of an object of study in terms of random variables and their associated probability distributions. One of the most basic statistical models is the simple linear regression model, which assumes a linear relationship between two measured variables. As an example and not by way of limitation, analysis system 180 may compare data from a pulse oximeter and a barometer and identify a linear correlation between a subject's blood-oxygen level and the barometric pressure at the subject's location. In particular embodiments, a predictive model may be used as a baseline model, wherein the predictive model was generated using controlled data over a specified period.

In particular embodiments, analysis system 180 may generate a model by normalizing or averaging one or more data streams. As an example and not by way of limitation, a model of a data stream from a single sensor 112 could simply be the average sensor measurement made by the sensor 112 over some initialization period. As another example and not by way of limitation, a model could be a single sensor measurement made during a control period.

In particular embodiments, analysis system 180 may generate a model by fitting one or more data sets to a mathematical function. As an example and not by way of limitation, a model could be an algorithm based on sensor measurements made by one or more sensors over some control period. The model may include a variety of variables, including data from one or more data streams and one or more fixed variables. The following is an example algorithm that analysis system 180 could generate to model a system or object:

$$f_m = f(D_{sensor}^1, \ldots, D_{sensor}^N, Y^1, \ldots, Y^M)$$

where:

$f_m$ is the model, $(D_{sensor}^1, \ldots, D_{sensor}^N)$ are data streams 1 through N, and $(Y^1, \ldots, Y^M)$ are fixed variables 1 through M.

In particular embodiments, the model may be used to predict hypothetical sensor measurements in theoretical or experimental systems. In particular embodiments, the model may be used to determine or categorize a subject's physiological or psychological state. As an example and not by way of limitation, the model may determine a subject's risk for a certain disease state with an abstract or statistical result. The model could simply identify the subject as being at "high risk" of developing a disease, or identify the subject as being 80% likely to develop the disease. As another example and not by way of limitation, the model may determine a subject's severity or grade of a disease state.

In particular embodiments, one or more sensors 112 in sensor array 110 may continuously transmit data regarding a subject's health to analysis system 180, which may monitor and automatically detect changes in the subject's health state. As used herein, "health state" refers to a person's physiological and psychological state, including the person's state with respect to pathologies and diseases. By using an integrated sensor array 110 to monitor physiological, psychological, behavioral, and environmental data, analysis system 180 may identify pathologies, disease states, sensitivities, and other health-related states with greater accuracy than is possible with any individual sensor 112.

In particular embodiments, one or more sensors 112 in sensor array 110 may measure one or more biomarkers. A biomarker is a characteristic that can be measured and evaluated as an indicator of biological processes, pathogenic processes, or pharmacologic responses. As an example and not by way of limitation, in a pharmacogenomic context, a biomarker would be a specific genetic variation that correlates with drug response. As another example and not by way of limitation, in a neurochemical context, a biomarker would be a person's subjective stress level that correlates with the person's plasma glucocorticoid level. As yet another example and not by way of limitation, in a neuropyschological context, a biomarker would be a person's serotonin uptake rate that correlates with the person's depression level. As yet another example and not by way of limitation, in a biochemical context, a biomarker would be a person's LDL cholesterol level that correlates with the person's risk of heart disease, such as heart attack. A biomarker is effectively a surrogate for measuring another physiological or psychological characteristic. A biomarker may include any type of stimulus, including physiological, psychological, behavioral, or environmental stimulus.

In particular embodiments, analysis system 180 may identify pathologies, disease states, and other health states of a subject. Certain physiological, psychological, behavioral, or environmental data may correlate with certain pathologies, disease states, and other health states. As an example and not by way of limitation, analysis system 180 could determine whether a subject has hypertension by monitoring a blood pressure data stream for a three week period and identifying substantial periods where the subject's blood pressure is at least 140/90 mmHg, wherein these substantial periods of elevated blood pressure constitute hypertension. The accuracy of identification may generally be increased as the number of data streams is increased. Analysis system 180 may contextualize and correlate data from multiple data streams to eliminate confounders from its data analysis and reduce the likelihood of generating false-positive and false-negative disease-state diagnoses. As an example and not by way of limitation, the hypertension diagnosis system described above may generate a false-positive diagnosis of hypertension if the subject engages in lengthy periods of physical activity, which naturally raise the subject's blood pressure. Therefore, if analysis system 180 also monitored a heart-rate data stream of the subject, it could eliminate blood pressure data sets that correlate with time periods of high heart-rate, thereby reducing the likelihood of generating an incorrect hypertension diagnosis.

In particular embodiments, analysis system 180 may analyze physiological, psychological, behavioral and environmental data steams to identify correlations between certain data sets and a subject's health state. As an example and not by way of limitation, analysis system 180 may be able to correlate a behavioral data set indicating the subject had a fight with a physiological data set indicating the subject had an elevated heart-rate to identify the fight as the cause of the elevated heart-rate. As another example and not by way of limitation, analysis system 180 may be able to correlate a physiological data set indicating the subject had an elevated skin temperature with a behavioral data set indicating the subject was engaged in physical activity to identify the physical activity as the cause of the elevated skin temperature. As yet another example and not by way of limitation, analysis system 180 may be able to correlate a psychological data set indicating the subject is depressed with an environmental data set indicating that the subject's stock portfolio substantially declined just prior to the onset of the subject's depression to identify the stock decline as the cause of the subject's depression. Analysis system 180 may use a variety of methods to identify correlations and generate causality hypotheses.

In particular embodiments, analysis system 180 may generate a model of a subject's health state. As an example and not by way of limitation, analysis system 180 may generate a baseline model of the subject's physiological or psychological state by analyzing one or more data streams during a control period. Once the baseline model is established, analysis system 180 could then continuously monitor the subject and identify deviations, variability, or changes in the data streams as compared to the baseline model. As another example and not by way of limitation, analysis system 180 may generate a predictive model of the subject's physiological or psychological state by analyzing one or more data streams and generating one or more algorithms that fit the sensor measurements. Once the predictive model is established, analysis system 180 could then be used to predict future health states, anticipated or hypothetical sensor readings, and other aspects of a subject's physiology or psychology. Analysis system 180 may also update and refine the predictive model based on new data generated by sensor array 110.

In particular embodiments, analysis system 180 may monitor disease-state progression and other health state changes over time. As an example and not by way of limitation, analysis system 180 could continuously monitor a subject's blood pressure over time to determine whether the subject's hypertension is improving. Such monitoring may be used to identify trends and to generate alerts or predictions regarding possible health states. Similarly, analysis system 180 may also monitor data streams containing treatment or therapy information to determine whether the treatment or therapy is efficacious. As an example and not by way of limitation, analysis system 180 could monitor a subject's blood pressure over time to determine whether an ACE inhibitor treatment is affecting the subject's hypertension.

In particular embodiments, analysis system 180 may monitor and analyze various data streams from a group of people to identify novel pre-disease states or risk states. As an example and not by way of limitation, one or more sensor arrays 110 could monitor a plurality of subjects. As multiple subjects develop certain diseases, analysis system 180 could analyze data sets from these subjects prior their development of the disease. The analysis of these data sets could allow analysis system 180 to identify certain health states that correlate with some level of risk for developing the disease.

Combining/Partitioning Medical Binary Decision Diagrams for Analysis Optimization In particular embodiments, sensor network 100 may construct one or more BDDs for analysis optimization from one or more other BDDs. Analysis optimization refers to increasing the speed or efficiency of an analytical process. As an example and not by way of limitation, sensor network 100 may partition a BDD into a plurality of sub-BDDs based on ease-of analysis. As another example and not by way of limitation, sensor network 100 may combine one or more portions of a plurality of BDDs into a new BDD based on ease-of-analysis. Although this disclosure describes particular components performing particular processes to construct one or more BDDs for analysis optimization from one or more other BDDs, this disclosure contemplates using any suitable components to construct one or more BDDs for analysis optimization from one or more other BDDs.

Figure 4:
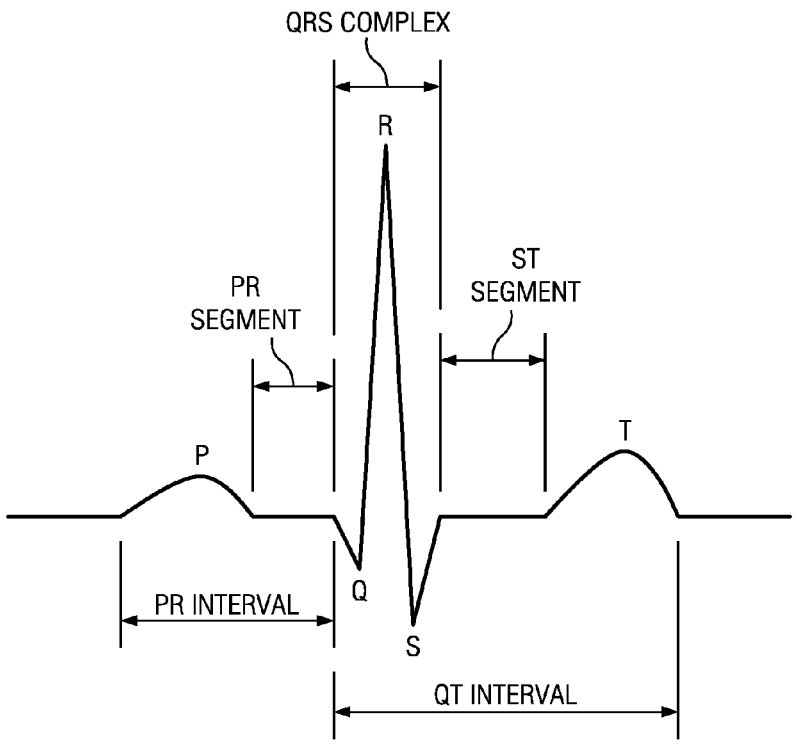
FIG. 4 illustrates an example data stream.

In particular embodiments, analysis system 180 may access one or more BDDs representing one or more data streams from a plurality of sensors 112. Each data stream may comprise a plurality of components. FIG. 4 illustrates an example data stream with a plurality of components. As an example and not by way of limitation, analysis system 180 may access a BDD representing the data stream illustrated in FIG. 4, which is a schematic of a single interval of a typical electrocardiograph (ECG) wave measuring the microvoltages in a heart muscle over time. Although FIG. 4 illustrates a single ECG wave in a data stream, this disclosure contemplates any suitable number of ECG waves in the data stream. The components of an ECG wave may include a PR interval, a QT interval, a PR segment, a QRS complex, and a ST segment. A component of a data stream may overlap in whole or in part with another component of the data stream. As an example and not by way of limitation, the ST segment overlaps in whole with the QT interval. Although this disclosure describes and FIG. 4 illustrates a particular data stream with particular components, this disclosure contemplates any suitable data stream with any suitable components. A BDD representing a data stream may comprise a plurality of portions, wherein each portion represents one component of the data stream. A portion of a BDD may include a path or set of paths in the BDD. As an example and not by way of limitation, the ECG wave illustrated in FIG. 4 may be represented by a BDD, such as $BDD_{E1}$, and each component of the ECG wave may be represented by a portion of $BDD_{E1}$. Each portion of a BDD may be represented by a sub-BDD that represents the component of the data stream represented by the portion. As an example and not by way of limitation, the PR interval, QT interval, PR segment, QRS complex, and ST segment may be represented by BDDs $BDD_{PR1}$, $BDD_{QT1}$, $BDD_{PR1}$, $BDD_{QRS1}$, and $BDD_{ST1}$, respectively, which are sub-BDDs of $BDD_{E1}$. Although this disclosure describes accessing particular BDDs representing particular data streams, this disclosure contemplates accessing any suitable BDDs representing any suitable data streams. Moreover, although this disclosure describes particular components accessing BDDs, this disclosure contemplates any suitable components accessing BDDs.

In particular embodiments, analysis system 180 may identify the components in a data stream. The components of a data stream may be identified in any suitable manner. In particular embodiments, analysis system 180 may identify components in a data stream based on the structural characteristics of the data stream. A structural characteristic of a data stream may be a structural characteristics of a waveform of a signal outputted by a sensor 112, a periodicity of a waveform of a signal outputted by a sensor 112, an identifier embedded in the data stream defining a component, another suitable structural characteristics, or two or more such structural characteristics. As an example and not by way of limitation, a component of an ECG wave may be identified based on structural characteristics of the waveform outputted by an electrocardiograph. Referring to FIG. 4, the PR segment may be identified as the component of the heart wave between the P wave and the QRS complex. The structure of P wave and the QRS complex can be defined by the shape of the components (i.e., the microvoltage versus time curve). As another example and not by way of limitation, a component of an ECG wave may be identified based on the periodicity of the waveform outputted by an electrocardiograph. Referring to FIG. 4, the periodicity of the waveform can be defined by the interval between an R wave and the next R wave (the RR interval), which is the inverse of the heart rate and occurs regularly. As yet another example and not by way of limitation, a component of an ECG wave may be identified based on an identifier embedded in the data stream defining the component. Referring to FIG. 4, an electrocardiograph may embed an identifier in the waveform, such as, for example, a peak after the T wave, to identify the end of the heart wave. In particular embodiments, analysis system 180 may identify components in a data stream based on the functional characteristics of the data stream. A functional characteristic of a data stream may be a rate of change of a waveform of a signal outputted by a sensor 112, minimum and/or maximum values of a waveform of a signal outputted by a sensor 112, another suitable functional characteristic, or two or more such functional characteristics. In particular embodiments, analysis system 180 may identify components in a data stream based on predefined component definitions provided by a user or another suitable source. As an example and not by way of limitation, a component of an ECG wave may be specified by a user. Referring to FIG. 4, a user may define a "PT interval" that consists of the PR segment, the QRS complex, and the ST segment. Although this disclosure describes identifying particular components in particular data streams, this disclosure contemplates identifying any suitable components in any suitable data streams. Moreover, although this disclosure describes particular processes for identifying components in a data stream, this disclosure contemplates any suitable processes for identifying components in a data stream.

In particular embodiments, analysis system 180 may select one or more portions from a plurality of portions in one or more BDDs based on ease-of-analysis. Ease-of-analysis refers to modifying one or more data sets to increase the speed or efficiency of an analytical process that references the data sets. Data sets may be modified for ease-of-analysis by combining, partitioning, compressing, restructuring, consolidating, adjusting, reorganizing, rewriting, annotating, or otherwise suitably modifying the data sets. As an example and not by way of limitation, an ease-of-analysis decomposition may refer to decomposing a BDD representing the ECG wave of FIG. 4 into BDDs representing the major components of the ECG signal, such as the PR interval, the QRS complex, and the QT interval. In particular embodiments, ease-of-analysis may be with respect to a particular analytic process. Analysis system 180 may receive information describing a particular analytical process and then identify one or more components from one or more data streams needed for the particular analytical process. Analysis system 180 may then select the portions of a BDD that represent the identified components. As an example and not by way of limitation, analysis system 180 may receive information describing an analytical process to determine the heart rate of a person. Referring to FIG. 4, the interval between an R wave and the next R wave (the RR interval) is the inverse of the heart rate. Analysis system 180 may identify the QRS complexes as the component of data stream needed to determine the heart rate of the person, and additional components of the data stream are not needed. Analysis system 180 may then select the portions of the BDD that represent the QRS complexes.

In particular embodiments, ease-of-analysis may be with respect to the compression rate achieved by constructing a sub-BDD from the selected component. A higher compression rate may lead to faster manipulation of a dataset and therefore easier analysis, however such a correlation is not always present or necessary. As an example and not by way of limitation, analysis system 180 may be able to achieve a higher compression rate by constructing sub-BDDs from various components of an ECG wave compared to storing the ECG wave as a single BDD. Referring to FIG. 4, the ECG wave illustrated may be stored as $BDD_{E1}$. $BDD_{E1}$ may be partitioned into sub-BDDs, such as $BDD_{QRS1}$ for storing QRS complex data and $BDD_{E2}$ for storing the remainder of the ECG wave. Because $BDD_{QRS1}$ only stores the portion of the data stream containing QRS complexes, it may have a relatively high compression rate. Furthermore, the sum of the sizes of $BDD_{QRS1}$ and $BDD_{E2}$ may be less than the size of $BDD_{E1}$. Although this disclosure describes selecting particular portions of particular BDDs, this disclosure contemplates selecting any suitable portions of any suitable BDDs. Moreover, although this disclosure describes ease-of-analysis with respect to particular factors, this disclosure contemplates ease-of-analysis with respect to any suitable factors.

In particular embodiments, analysis system 180 may construct a plurality of sub-BDDs by partitioning a first BDD. The sub-BDDs may comprise a first sub-BDD representing the portions selected based on ease-of-analysis, and one or more second sub-BDDs representing the non-selected portions. The sub-BDDs may be constructed in any suitable manner. A BDD may be partitioned into a plurality of sub-BDDs according to existing BDD partition rules. As an example and not by way of limitation, a BDD representing Boolean function $f(x_1, \ldots, x_n)$ may be partitioned into two or more sub-BDDs representing Boolean functions $f_1(x_1, \ldots, x_n)$ to $f_m(x_1, \ldots, x_n)$. Each of the Boolean functions may be considered a partition of the original Boolean function $f$. If each of the Boolean functions $f_1$ to $f_m$ is represented by a BDD, then the BDD that represents the original Boolean function $f$ may be obtained by logically ORing all the BDDs that represent the partitions of $f$ (i.e., $f_1$ to $f_m$). As another example and not by way of limitation, a BDD representing the ECG wave illustrated in FIG. 4, $BDD_{E1}$, may be partitioned into two or more sub-BDDs representing various components of the ECG wave, such as $BDD_{QRS1}$ representing the QRS complex and $BDD_{E2}$ representing the remainder of the ECG wave. In particular embodiments, analysis system 180 may then perform a particular analytical process with one or more of the sub-BDDs. In particular embodiments, analysis system 180 may then store the first sub-BDD representing the portions selected based on ease-of-analysis, and delete one or more of the second sub-BDDs representing the non-selected portions. Although this disclosure describes constructing a plurality of sub-BDDs by partitioning a first BDD using particular components and particular processes, this disclosure contemplates constructing a plurality of sub-BDDs by partitioning a first BDD using any suitable components and any suitable processes.

In particular embodiments, analysis system 180 may construct a second BDD by combining a plurality of portions from a plurality of first BDDs. The plurality of portions may comprise the portions selected based on ease-of-analysis. As an example and not by way of limitation, portions may be selected based on whether the combined BDD requires less space. A second BDD may be constructed from a plurality of portions of first BDDs in any suitable manner. As an example and not by way of limitation, a plurality of first BDDs representing Boolean functions $f_1(x_1, \ldots, x_n)$ to $f_m(x_1, \ldots, x_n)$ may be combined into a second BDD representing Boolean function $F(x_1, \ldots, x_n)$. Each of the Boolean functions $f_1(x_1, \ldots, x_n)$ to $f_m(x_1, \ldots, x_n)$ may be considered a partition of the Boolean functions represented by the plurality of first BDDs. If each of the Boolean functions $f_1$ to $f_m$ is represented by a BDD, then the second BDD that represents the Boolean function F may be obtained by logically ORing all the BDDs that represent $f_1$ to $f_m$. As another example and not by way of limitation, a plurality of portions from a plurality of first BDDs representing a plurality of ECG waves, like the wave illustrated in FIG. 4, may be combined into a second BDD. The portion of each first BDD representing the QRS complex may be combined into a second BDD representing the QRS complex from each first BDD. In particular embodiments, analysis system 180 may then perform a particular analytical process with the second BDD. In particular embodiments, analysis system 180 may then store the second BDD representing the portions of the first BDDs selected based on ease-of-analysis, and delete one or more of the first BDDs. Although this disclosure describes constructing a second BDD by combining a plurality of portions from a plurality of first BDDs using particular components and particular processes, this disclosure contemplates constructing a second BDD by combining a plurality of portions from a plurality of first BDDs using any suitable components and any suitable processes.

In particular embodiments, analysis system 180 may optimize the size of a BDD before combining or partitioning the BDD. As an example and not by way of limitation, analysis system 180 may optimize the size of the BDD using variable reordering.

Figure 5:
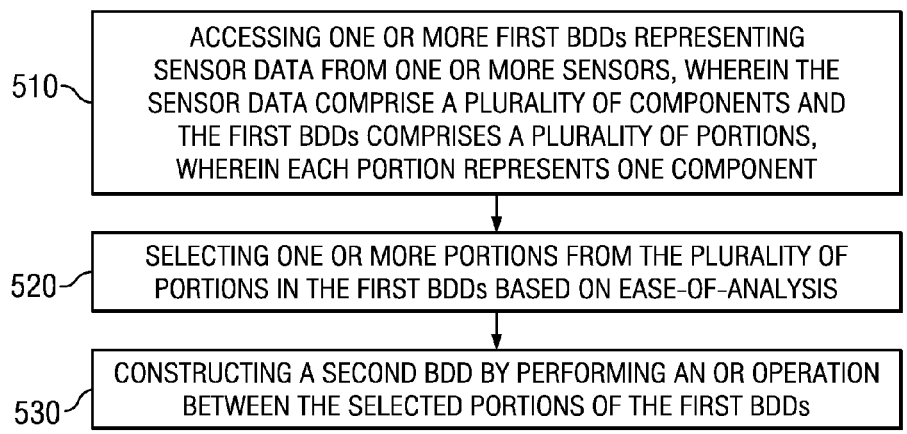
FIG. 5 illustrates an example method for combining medical binary decision diagrams for analysis optimization.

FIG. 5 illustrates an example method for combining medical binary decision diagrams for analysis optimization. The method begins at step 510, where analysis system 180 accesses a plurality of first BDDs representing a plurality of data streams from a plurality of sensors 112. The plurality of data streams comprise a plurality of components and the first BDDs comprise a plurality of portions, wherein each portion represents one component. At step 520, analysis system 180 selects one or more portions from the plurality of portions in the first BDDs based on ease-of-analysis. At step 530, analysis system 180 constructs a second BDD by performing an OR operation between the selected portions of the first BDDs. Although this disclosure describes and illustrates particular steps of the method of FIG. 5 as occurring in a particular order, this disclosure contemplates any suitable steps of the method of FIG. 5 occurring in any suitable order. Moreover, although this disclosure describes and illustrates particular components carrying out particular steps of the method of FIG. 5, this disclosure contemplates any suitable combination of any suitable components carrying out any suitable steps of the method of FIG. 5.

Figure 6:
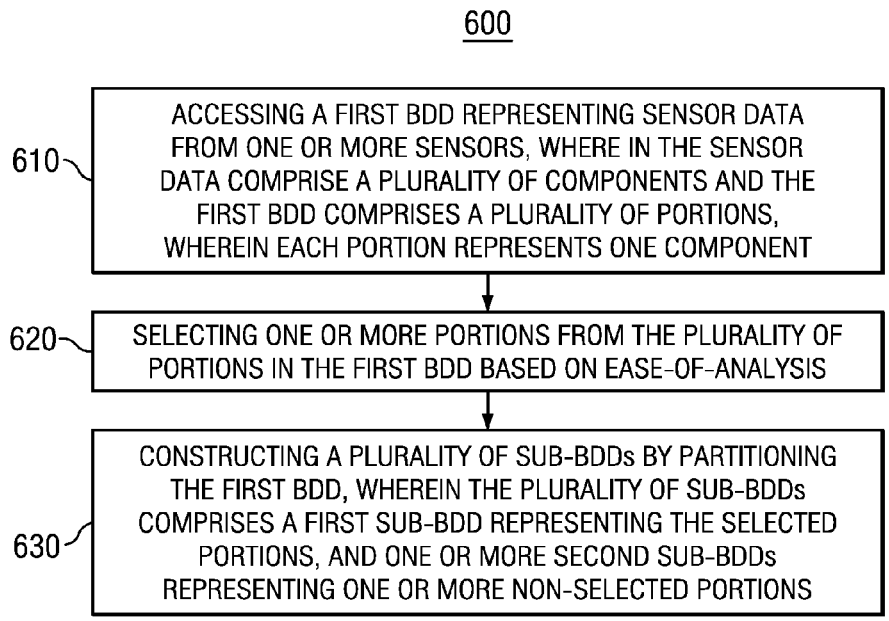
FIG. 6 illustrates an example method for partitioning medical binary decision diagrams for analysis optimization.

FIG. 6 illustrates an example method for partitioning medical binary decision diagrams for analysis optimization. The method begins at step 610, where analysis system 180 accesses a first BDD representing one or more data streams from one or more sensors 112, wherein the one or more data streams comprise a plurality of components and the first BDD comprises a plurality of portions, wherein each portion represents one component. At step 620, analysis system 180 selects one or more portions from the plurality of portions in the first BDD based on ease-of-analysis. At step 630, analysis system 180 constructs a plurality of sub-BDDs by partitioning the first BDD, wherein the plurality of sub-BDDs comprises a first sub-BDD representing the selected portions, and one or more second sub-BDDs representing one or more of the non-selected portions. Although this disclosure describes and illustrates particular steps of the method of FIG. 6 as occurring in a particular order, this disclosure contemplates any suitable steps of the method of FIG. 6 occurring in any suitable order. Moreover, although this disclosure describes and illustrates particular components carrying out particular steps of the method of FIG. 6, this disclosure contemplates any suitable combination of any suitable components carrying out any suitable steps of the method of FIG. 6.

Combining/Partitioning Medical Binary Decision Diagrams for Size Optimization

In particular embodiments, sensor network 100 may construct one or more BDDs for size optimization from one or more other BDDs. Size optimization refers to decreasing the size or increasing the compression ratio of data for storing or processing. As an example and not by way of limitation, sensor network 100 may combine a plurality of first BDDs into one or more second BDDs based on size optimization. As another example and not by way of limitation, sensor network 100 may partition a BDD into a plurality of sub-BDDs based on size optimization. Although this disclosure describes particular components performing particular processes to construct one or more BDDs for size optimization from one or more other BDDs, this disclosure contemplates using any suitable components to construct one or more BDDs for size optimization from one or more other BDDs.

In particular embodiments, analysis system 180 may access one or more BDDs representing one or more data streams from a plurality of sensors 112. Each data stream may comprise a plurality of components. A BDD representing a data stream may comprise a plurality of portions, wherein each portion represents one component of the data stream. A portion of a BDD may include a path or set of paths in the BDD. Each portion of a BDD may be represented by a sub-BDD that represents the component of the data stream represented by the portion. As an example and not by way of limitation, analysis system 180 may access $BDD_{E1}$ representing the data stream illustrated in FIG. 4.

In particular embodiments, analysis system 180 may construct a second BDD by combining a plurality of first BDDs. A second BDD may be constructed from the plurality of first BDDs by any suitable process. As an example and not by way of limitation, a plurality of first BDDs representing Boolean functions $f_1(x_1, \ldots, x_n)$ to $f_m(x_1, \ldots, x_n)$ may be combined into a second BDD representing Boolean function $F(x_1, \ldots, x_n)$. If each of the Boolean functions $f_1$ to $f_m$ is represented by a first BDD, then the second BDD that represents the Boolean function F may be obtained by logically ORing all the first BDDs that represent $f_1$ to $f_m$. As another example and not by way of limitation, a plurality of first BDDs representing a plurality of ECG waves, like the wave illustrated in FIG. 4, may be combined into second BDD representing the plurality of ECG waves. Although this disclosure describes constructing a second BDD by combining a plurality of first BDDs using particular components and particular processes, this disclosure contemplates constructing a second BDD by combining a plurality of first BDDs using any suitable components and any suitable processes.

In particular embodiments, analysis system 180 may select one or more portions from a plurality of portions in one or more first BDDs. As an example and not by way of limitation, analysis system 180 may select one or more portions of a BDD representing Boolean function $f(x_1, \ldots, x_n)$. As another example and not by way of limitation, analysis system 180 may select the portions of $BDD_{E1}$ that represent the QRS complexes illustrated in FIG. 4. In particular embodiments, analysis system 180 may then construct a second BDD representing the selected portions and a third BDD representing the non-selected portions. The second and third BDDs may be constructed in any suitable manner, such as, for example, by partitioning the first BDD into the second and third BDDs according to existing BDD partition rules. As an example and not by way of limitation, a first BDD representing Boolean function $f(x_1, \ldots, x_n)$ may be partitioned into one or more second BDDs representing Boolean functions $f_1^s(x_1, \ldots, x_n)$ to $f_m^s(x_1, \ldots, x_n)$, which represent the selected portions of the first BDD, and one or more third BDDs representing Boolean functions $f_1^{ns}(x_1, \ldots, x_n)$ to $f_p^{ns}(x_1, \ldots, x_n)$, which represent the non-selected portions of the first BDD. Each of the Boolean functions to may be considered a partition of the original Boolean function $f$. If each of the Boolean functions $f_1^s$ to $f_m^s$ and $f_1^{ns}$ to $f_p^{ns}$ is represented by a BDD, then the BDD that represents the original Boolean function $f$ may be obtained by logically ORing all the BDDs that represent the partitions of $f$ (i.e., $f_1^s$ to $f_m^s$ and $f_1^{ns}$ to $f_p^{ns}$). As another example and not by way of limitation, a BDD representing the ECG wave illustrated in FIG. 4, $BDD_{E1}$, may be partitioned into two or more sub-BDDs representing various components of the ECG wave. If the selected portion is the portion representing the QRS complex, then analysis system 180 may partition $BDD_{E1}$ into such as $BDD_{QRS1}$ representing the QRS complex and $BDD_{E2}$ representing the unselected portions of $BDD_{E1}$, wherein $BDD_{E2}$ represents the remainder of the ECG wave. Although this disclosure describes constructing a second BDD representing the selected portions and a third BDD representing the non-selected portions using particular components and particular processes, this disclosure contemplates constructing a second BDD representing the selected portions and a third BDD representing the non-selected portions using any suitable components and any suitable processes.

In particular embodiments, analysis system 180 may determine the size of one or more BDDs. The size of a BDD may be based on the function the BDD represents and the ordering of variables in the BDD. The size of a BDD may be directly obtained from the number of nodes in the BDD. As an example and not by way of limitation, a BDD may have a size expressed as a number of bits that indicate how much storage is associated with the BDD. In particular embodiments, analysis system 180 may optimize the size of one or more BDDs before determining the size of the BDDs. As an example and not by way of limitation, analysis system 180 may optimize the size of the BDD using variable reordering.

Although this disclosure describes particular processes for determining the size of a BDD, this disclosure contemplates any suitable processes for determining the size of a BDD.

In particular embodiments, analysis system 180 may compare the sizes of the one or more original BDDs and the one or more BDDs that were constructed by combining or partitioning the original BDDs. The sizes of the BDDs may be compared in any suitable manner. As an example and not by way of limitation, analysis system 180 may determine the number of bits needed to store a BDD on a particular data store. In particular embodiments, analysis system 180 may store the BDDs with smaller sizes and delete the BDDs with larger sizes after comparing the sizes of the BDDs. A BDD may be stored on any suitable data store. As an example and not by way of limitation, where a second BDD was constructed by combining a plurality of first BDDs, if the size of the second BDD is less than the sum of the sizes of the first BDDs, then analysis system 180 may store the second BDD and delete the first BDDs; else, analysis system 180 may store the first BDDs and delete the second BDD. As another example and not by way of limitation, where a first BDD is partitioned into a second and third BDDs, if the size of the first BDD is less than the sum of the sizes of the second and third BDDs, then analysis system 180 may store the first BDD and delete the second and third BDDs; else, analysis system 180 may store the second and third BDDs and delete the first BDD. Although this disclosure describes comparing the sizes of particular BDDs, this disclosure contemplates comparing the sizes of any suitable BDDs. Moreover, although this disclosure describes storing and deleting BDDs based on particular size comparisons, this disclosure contemplates storing and deleting BDDs based on any suitable size comparisons.

Although this disclosure describes combining a particular number of BDDs for size optimization, this disclosure contemplates combining any suitable number of BDDs for size optimization. As an example and not by way of limitation, analysis system 180 may access a first BDD representing a first data stream from a first sensor 112, a second BDD representing a second data stream from a second sensor 112, and a third BDD representing a third data stream from a third sensor 112. Analysis system 180 may then construct a fourth BDD by performing an OR operation between the first and second BDDs, construct a fifth BDD by performing an OR operation between the first and third BDDs, construct a sixth BDD by performing an OR operation between the second and third BDDs, and construct a seventh BDD by performing an OR operation between the first BDD, the second BDD, and the third BDD. Analysis system 180 may then determine a first size of the first BDD, a second size of the second BDD, and a third size of the third BDD, a fourth size of the fourth BDD, a fifth size of the fifth BDD, a sixth size of the sixth BDD, a seventh size of the seventh BDD, a sum of the sizes of the first and sixth BDDs, a sum of the sizes of the second and fifth BDDs, a sum of the sizes of the third and fourth BDDs, and a sum of the sizes of the first, second, and third BDDs. Analysis system 180 may then select the smallest size from the group consisting of: the seventh size of the seventh BDD; the sum of the sizes of the first and sixth BDDs; the sum of the sizes of the second and fifth BDDs; the sum of the sizes of the third and fourth BDDs; and the sum of the sizes of the first, second, and third BDDs. Analysis system 180 may then store the BDDs corresponding to the selected group and delete the remaining BDDs.

Although this disclosure describes partitioning a BDD into a particular number of BDDs for size optimization, this disclosure contemplates partitioning a BDD into any suitable number of BDDs for size optimization. As an example and not by way of limitation, analysis system 180 may access a first BDD representing one or more data streams from one or more sensors 112. The data streams may comprise a plurality of components. The first BDD may comprise a plurality of portions, wherein each portion represents one or more components of one or more data streams. Analysis system 180 may then select one or more first portions from the plurality of portions in the first BDD and select one or more second portions from the plurality of portions in the first BDD. Analysis system 180 may then construct a second BDD representing the first selected portions, construct a third BDD representing the second selected portions, construct a fourth BDD representing the non-selected portions, construct a fifth BDD representing a combination of the first and second selected portions, construct a sixth BDD representing a combination of the second selected portions and the non-selected portions, and construct a seventh BDD representing a combination of the first selected portions and the non-selected portions. Analysis system 180 may then determine a first size of the first BDD, a second size of the second BDD, and a third size of the third BDD, a fourth size of the fourth BDD, a fifth size of the fifth BDD, a sixth size of the sixth BDD, a seventh size of the seventh BDD, a sum of the sizes of the second and sixth BDDs, a sum of the sizes of the seventh and third BDDs, a sum of the sizes of the fifth and fourth BDDs, and a sum of the sizes of the second, third, and fourth BDDs. Analysis system 180 may then select the smallest size from the group consisting of: the first size of the first BDD; the sum of the sizes of the second and sixth BDDs; the sum of the sizes of the seventh and third BDDs; the sum of the sizes of the fifth and fourth BDDs; and the sum of the sizes of the second, third, and fourth BDDs. Analysis system 180 may then store the BDDs corresponding to the smallest size and delete the remaining BDDs.

As another example and not by way of limitation, analysis system 180 may access a first BDD representing one or more data streams from one or more sensors 112. The data streams may comprise a plurality of components. The first BDD may comprise a plurality of portions, wherein each portion represents one or more components of one or more data streams. Analysis system 180 may then partition the first BDD into p second BDDs, wherein p≥3. Each second BDD represents one or more unique portions of the first BDD and the combination of the p second BDDs is equivalent to the first BDD. Analysis system 180 may then construct $$m = \sum_{2 \le k \le p-1} \binom{p}{k}$$

third BDDs, wherein each of the in third BDDs is a unique combination of k second BDDs. Analysis system 180 may then determine o values based on the second or third BDDs, wherein each o value equals a sum of zero or more second sizes of zero or more second BDDs, respectively, and zero or more third sizes of zero or more third BDDs, respectively. In determining the o values, a combination of the zero or more second BDDs and the zero or more third BDDs is equivalent to the first BDD. Analysis system 180 may then select the smallest value among a first size of the first BDD and the o values. Analysis system 180 may then store one or more of the first BDD, the p second BDDs, or the in third BDDs corresponding to the smallest size.

Figure 7:
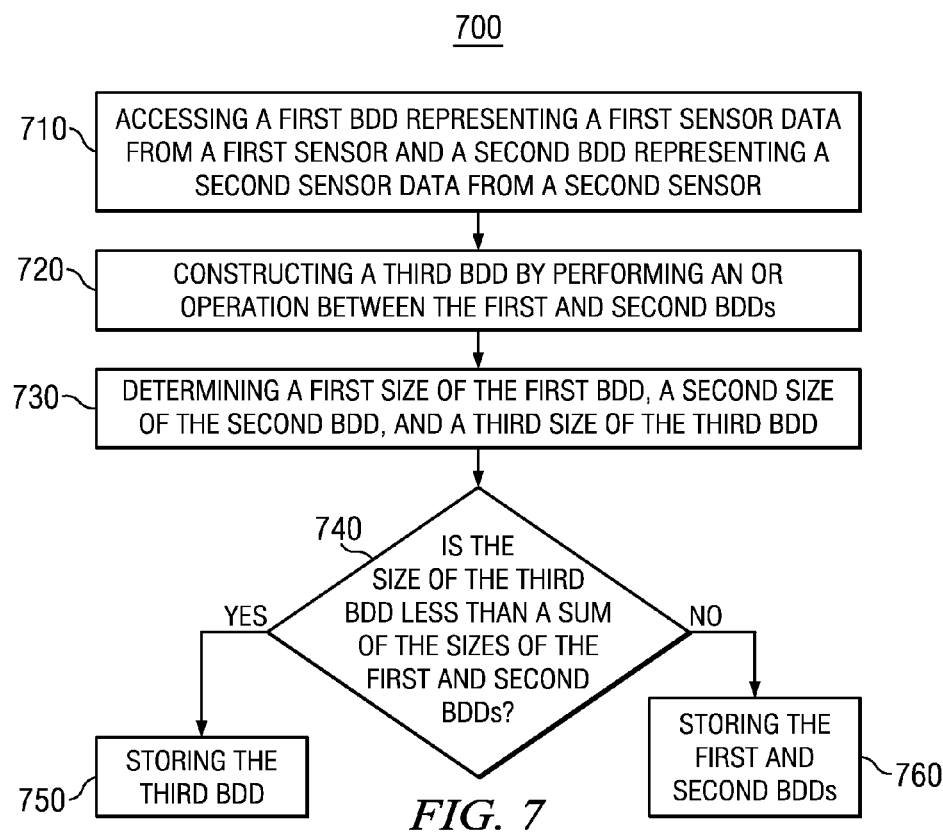
FIG. 7 illustrates an example method for combining medical binary decision diagrams for size optimization.

FIG. 7 illustrates an example method for combining medical binary decision diagrams for size optimization. The method begins at step 710, where analysis system 180 accesses a first BDD representing a first data stream from a first sensor 112 and a second BDD representing a second data stream from a second sensor 112. At step 720, analysis system 180 constructs a third BDD by performing an OR operation between the first and second BDDs. At step 730, analysis system 180 determines a first size of the first BDD, a second size of the second BDD, and a third size of the third BDD. At step 740, analysis system 180 determines if the size of the third BDD is less than a sum of the sizes of the first and second BDDs. If the size of the third BDD is less than the sum of the sizes of the first and second BDDs, then analysis system 180 stores the third BDD at step 750. But if the size of the third BDD is not less than the sum of the sizes of the first and second BDDs, then analysis system 180 stores the first and second BDDs. Although this disclosure describes and illustrates particular steps of the method of FIG. 7 as occurring in a particular order, this disclosure contemplates any suitable steps of the method of FIG. 7 occurring in any suitable order. Moreover, although this disclosure describes and illustrates particular components carrying out particular steps of the method of FIG. 7, this disclosure contemplates any suitable combination of any suitable components carrying out any suitable steps of the method of FIG. 7.

Figure 8:
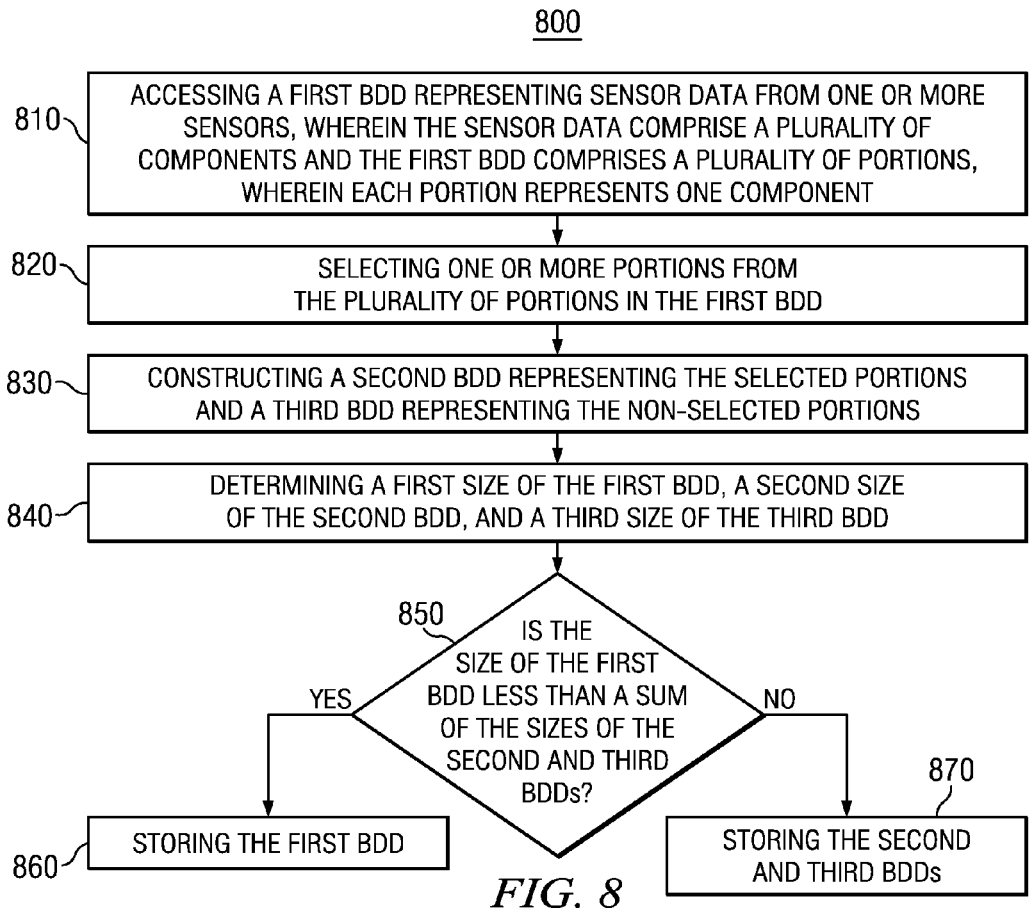
FIG. 8 illustrates an example method for partitioning medical binary decision diagrams for size optimization.

FIG. 8 illustrates an example method for partitioning medical binary decision diagrams for size optimization. The method begins at step 810, where analysis system 180 accesses a first BDD representing one or more data streams from one or more sensors 112. The one or more data streams comprise a plurality of components and the first BDD comprises a plurality of portions, wherein each portion represents one component. At step 820, analysis system 180 selects one or more portions from the plurality of portions in the first BDD. At step 830, analysis system 180 constructs a second BDD representing the selected portions and a third BDD representing the non-selected portions. At step 840, analysis system 180 determines a first size of the first BDD, a second size of the second BDD, and a third size of the third BDD. At step 850, analysis system 180 determines if the size of the first BDD is less than a sum of the sizes of the second and third BDDs. If the size of the first BDD is less than the sum of the sizes of the second and third BDDs, then analysis system 180 stores the first BDD at step 860. But if the size of the first BDD is not less than the sum of the sizes of the second and third BDDs, then analysis system 180 stores the second and third BDDs at step 870. Although this disclosure describes and illustrates particular steps of the method of FIG. 8 as occurring in a particular order, this disclosure contemplates any suitable steps of the method of FIG. 8 occurring in any suitable order. Moreover, although this disclosure describes and illustrates particular components carrying out particular steps of the method of FIG. 8, this disclosure contemplates any suitable combination of any suitable components carrying out any suitable steps of the method of FIG. 8.

Identifying Correlations in Medical BDDs

In particular embodiments, sensor network 100 may construct one or more BDDs representing a plurality of data streams to determine if the data streams are related. A relationship between data streams may include, for example, correlations, causal relationships, dependent relationships, reciprocal relationships, data equivalence, another suitable relationship, or two or more such relationship. Correlating is establishing or demonstrating a causal, complementary, parallel, or reciprocal relation between one data set and another data set. As an example and not by way of limitation, there is a positive correlation activity level in a person and the heart rate of the person. The degree of correlation is the degree to which two or more measurements change simultaneously. These correlations may be of varying degrees of dependence (e.g., as determined by a Pearson's product-moment coefficient). In general, analysis system 180 may make more accurate correlations as more data becomes available from sensor array 110. Analysis system 180 may then use these correlations to generate causality hypotheses of varying degrees of confidence. In general, analysis system 180 may make more accurate correlations as more data becomes available from sensor array 110. As an example and not by way of limitation, sensor network 100 may combine a plurality of BDDs representing a plurality of data streams to determine if the data streams are related by comparing the size of the original BDDs to the combined BDDs. As another example and not by way of limitation, sensor network 100 may partition a BDD representing a plurality of data streams into a plurality of sub-BDDs to determine if the data streams are related by comparing the size of the BDD and the sub-BDDs.

Although this disclosure describes particular components performing particular process to construct one or more BDDs representing a plurality of data streams to determine if the data streams are related, this disclosure contemplates any suitable components performing any suitable processes to construct one or more BDDs representing a plurality of data streams to determine if the data streams are related.

In particular embodiments, analysis system 180 may access one or more BDDs representing one or more data streams from a plurality of sensors 112. A BDD representing a data stream may comprise a plurality of portions, wherein each portion represents one data stream. A portion of a BDD may include a path or set of paths in the BDD. Each portion of a BDD may be represented by a sub-BDD that represents the data stream represented by the portion. As an example and not by way of limitation, analysis system 180 may access $BDD_A$ representing the data stream from sensor A and access $BDD_B$ representing the data stream from sensor B. As another example and not by way of limitation, analysis system 180 may access $BDD_{AB}$ representing the data streams from sensors A and B.

In particular embodiments, analysis system 180 may determine whether one or more data streams represented by one or more BDDs are related by combining or partitioning the BDDs, determining the sizes of the original and resulting BDDs, and indicating the data stream are or are not related based on the sizes of the BDDs. If two data sets are related, two BDDs representing each data set may have a sum of sizes larger than the size of a single BDD representing both data sets. Similarly, if two data sets are not related, two BDDs representing each data set may have a sum of sizes smaller than the size of a single BDD representing both data sets. Two BDDs may be described as being "compatible" if the BDDs can be combined into a new BDD that has a smaller size than the sum of the sizes of the original BDDs. That two BDDs are compatible does not necessarily mean the data represented by those BDDs correlate. However, BDDs that are more compatible (i.e., BDDs that exhibit a greater size reduction when combined) generally have a greater degree of correlation.

In particular embodiments, analysis system 180 may construct a BDD representing a combination of a plurality of BDDs. The third BDD may be constructed in any suitable manner. As an example and not by way of limitation, a first BDD representing Boolean function $f_1(x_1, \ldots, x_n)$ and a second BDD representing Boolean function $f_2(x_1, \ldots, x_n)$ may be combined into a third BDD representing Boolean function $f_3(x_1, \ldots, x_n)$. If the Boolean functions $f_1$ and $f_2$ are represented by the first and second BDDs, respectively, then the third BDD represents the Boolean function $f_3$ may be obtained by logically ORing the first BDD that represents $f_1$ to the second BDD the represents $f_2$. As another example and not by way of limitation, $BDD_A$ representing the data stream from sensor A and $BDD_B$ representing the data stream from sensor B may be combined into $BDD_{AB}$ representing the data streams from sensors A and B by logically ORing $BDD_A$ and $BDD_B$. Although this disclosure describes constructing a BDD using particular components and particular processes, this disclosure contemplates constructing a BDD using any suitable components and any suitable processes.

In particular embodiments, analysis system 180 may partition a BDD representing a plurality of data streams into a plurality of sub-BDDs. Each sub-BDD may represent a data stream. The sub-BDDs may be constructed in any suitable manner. A BDD may be partitioned into a plurality of sub-BDDs according to existing BDD partition rules. As an example and not by way of limitation, a BDD representing Boolean function $f(x_1, \ldots, x_n)$ may represent data streams 1 to m from sensors 1 to m. The BDD representing Boolean function $f(x_1, \ldots, x_n)$ may be partitioned into a plurality of sub-BDDs representing Boolean functions $f_1(x_1, \ldots, x_n)$ to $f_m(x_1, \ldots, x_n)$, which represent data streams 1 to m, respectively. Each of the Boolean functions to may be considered a partition of the original Boolean function $f$. If each of the Boolean functions $f_1$ to $f_m$ is represented by a BDD, then the BDD that represents the original Boolean function $f$ may be obtained by logically ORing all the BDDs that represent the partitions of $f$ (i.e., $f_1$ to $f_m$). As another example and not by way of limitation, $BDD_{AB}$ representing the data streams from sensor A and sensor B may be partitioned into $BDD_A$ representing the data stream from sensor A and $BDD_B$ representing the data stream from sensor B. Although this disclosure describes constructing a BDD using particular components and particular processes, this disclosure contemplates constructing a BDD using any suitable components and any suitable processes.

In particular embodiments, analysis system 180 may determine the size of one or more BDDs. The size of a BDD may be based on the function the BDD represents and the ordering of variables in the BDD. The size of a BDD may be directly obtained from the number of nodes in the BDD. As an example and not by way of limitation, a BDD may have a size expressed as a number of bits that indicate how much storage is associated with the BDD. In particular embodiments, analysis system 180 may optimize the size of one or more BDDs before determining the size of the BDDs. As an example and not by way of limitation, analysis system 180 may optimize the size of the BDD using variable reordering. Although this disclosure describes particular processes for determining the size of a BDD, this disclosure contemplates any suitable processes for determining the size of a BDD.

In particular embodiments, analysis system 180 may compare the sizes of the one or more original BDDs and the one or more BDDs that were constructed by combining or partitioning the original BDDs and indicate that a first and second data streams are related based on the size comparison. The sizes of BDDs may be compared in any suitable manner. As an example and not by way of limitation, where a second BDD was constructed by combining a plurality of first BDDs representing a plurality of data streams, if the size of the second BDD is less than the sum of the sizes of the first BDDs, then analysis system 180 may indicate that the data streams are related; else, analysis system 180 may indicate that the data streams are not related. As another example and not by way of limitation, where a first BDD representing a plurality of data streams is partitioned into a second and third BDDs, if the size of the first BDD is less than the sum of the sizes of the second and third BDDs, then analysis system 180 may indicate that the data streams are related; else, analysis system 180 may indicate that the data streams are not related. Although this disclosure describes comparing the sizes of particular BDDs, this disclosure contemplates comparing the sizes of any suitable BDDs.

In particular embodiments, analysis system 180 may determine that the relationship between data sets is a correlation. Analysis system 180 may compare the sizes of the one or more original BDDs and the one or more BDDs that were constructed by combining or partitioning the original BDDs and indicate that a first and second data streams are correlated based on the size comparison. If the data sets correlate, the size of the combined BDD (i.e., the BDD representing two or more data streams) will be less than the sum of the sizes of the individual BDDs (i.e., the BDDs that represent a single data stream). However, if the data sets do not correlate, the size of the combined BDD will be equal to or greater than the sum of the sizes of the individual BDDs. As an example and not by way of limitation, if sensor array 110 comprises sensor A and sensor B, the data streams from the sensors may be represented by $BDD_A$ and $BDD_B$, respectively. If the data streams from sensors A and B correlate, the size of $BDD_{AB}$ will be less than the sum of the sizes of $BDD_A$ and $BDD_B$. However the data streams from sensors A and B do not correlate if the size of $BDD_{AB}$ is equal to or greater than the sum of the sizes of $BDD_A$ and $BDD_B$. If sensor array 110 comprises a plurality of sensors 112, the optimal BDD representation may not necessarily be obtained by combining all sensor output in a single BDD. As an example and not by way of limitation, a data stream from a rapidly changing EKG, such as the data stream illustrated in FIG. 4, may not co-exist well inside a BDD with the output from a rapidly changing electroencephalograph (EEG). As another example and not by way of limitation, heart rate and respiration rate change relatively slowly and are generally related. Therefore, a BDD representing data streams from a heart rate sensor and a respiration sensor may have a smaller size than two BDDs representing the heart rate data and respiration data separately. In particular embodiments, analysis system may store BDDs representing individual data streams, and may combine the BDDs when the resulting graph is smaller than the individual BDDs. This approach may result in the generation of plurality of BDDs to store data from a plurality of sensors 112, resulting in a classical Partitioned OBDD representation.

In particular embodiments, analysis system 180 may determine the degree that the first and second data streams correlate by comparing the size of the BDD representing the first and second data streams and the sum of the sizes of the BDD representing the first data stream and the BDD representing the second data stream. The degree that the first and second data streams correlate is indicated by the amount that the size of the BDD representing the first and second data streams is less than the sum of the sizes of the BDD representing the first data stream and the BDD representing the second data stream. In other words, the degree of correlation increases as the size of the combined BDD decreases with respect to the sum of the sizes of the individual BDDs. As an example and not by way of limitation, analysis system may combine $BDD_A$ representing a data stream from sensor A with $BDD_B$ representing the data stream from sensor B to create $BDD_{AB}$ representing both data streams. If the size of $BDD_{AB}$ is less than the sum of the sizes of $BDD_A$ and $BDD_B$, then the data streams from sensors A and B correlate. Furthermore, the smaller $BDD_{AB}$ is with respect to the sum of the sizes of $BDD_A$ and $BDD_B$, then the greater the degree of correlation between the data streams from sensors A and B.

Although this disclosure describes combining a particular number of BDDs representing a particular number of data streams to determine if the data streams are related, this disclosure contemplates combining any suitable number of BDDs representing any suitable number of data streams to determine if the data streams are related. Moreover, although this disclosure describes partitioning a BDD representing a particular number of data streams into a particular number of sub-BDDs to determine if the data streams are related, this disclosure contemplates partitioning a BDD representing any suitable number of data streams into any suitable number of sub-BDDs to determine if the data streams are related. As an example and not by way of limitation, analysis system 180 may perform one or more of the methods described herein on BDDs representing three or more data streams by forming multiple combined BDDs that combine the various individual BDDs and analyzing the sizes of the combined and individual BDDs as discussed herein.

Figure 9:
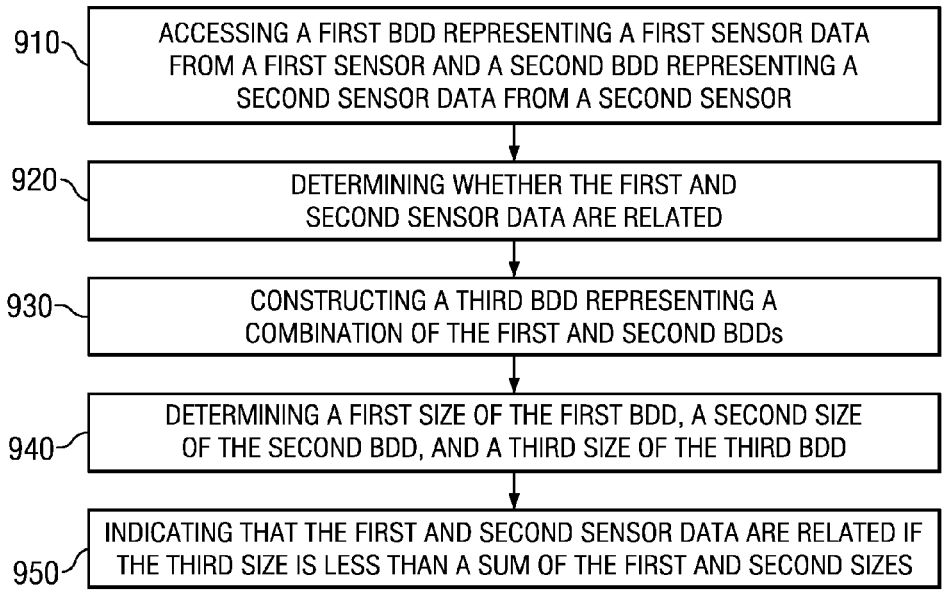
FIG. 9 illustrates an example method for combining medical binary decision diagrams to determine if data is related.

FIG. 9 illustrates an example method for combining medical binary decision diagrams to determine if data are related. The method begins at step 910, where analysis system 180 accesses a first BDD representing a first data stream from a first sensor 112 and a second BDD representing a second data stream from a second sensor 112. At step 920, analysis system 180 determines whether the first and second data streams are related. The relation between the first and second data streams may be a correlation. At step 930, analysis system 180 constructs a third BDD representing a combination of the first and second BDDs. At step 940, analysis system 180 determines a first size of the first BDD, a second size of the second BDD, and a third size of the third BDD. At step 950, analysis system 180 indicates that the first and second data streams are related if the third size is less than a sum of the first and second sizes. Although this disclosure describes and illustrates particular steps of the method of FIG. 9 as occurring in a particular order, this disclosure contemplates any suitable steps of the method of FIG. 9 occurring in any suitable order. Moreover, although this disclosure describes and illustrates particular components carrying out particular steps of the method of FIG. 9, this disclosure contemplates any suitable combination of any suitable components carrying out any suitable steps of the method of FIG. 9.

Figure 10:
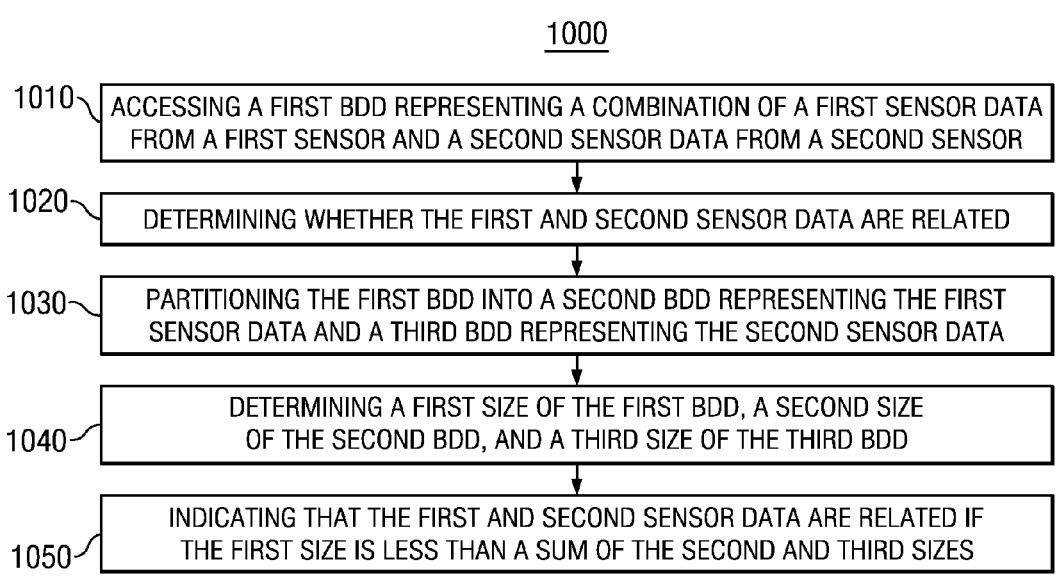
FIG. 10 illustrates an example method for partitioning medical binary decision diagrams to determine if data is related.

FIG. 10 illustrates an example method for partitioning medical binary decision diagrams to determine if data are related. The method begins at step 1010, where analysis system 180 accesses a first BDD representing a combination of a first data stream from a first sensor 112 and a second data stream from a second sensor 112. At step 1020, analysis system 180 determines whether the first and second data streams are related. The relation between the first and second data streams may be a correlation. At step 1030, analysis system 180 partitions the first BDD into a second BDD representing the first data stream and a third BDD representing the second data stream. At step 1040, analysis system 180 determines a first size of the first BDD, a second size of the second BDD, and a third size of the third BDD. At step 1050, analysis system 180 indicates that the first and second data streams are related if the first size is less than a sum of the second and third sizes. Although this disclosure describes and illustrates particular steps of the method of FIG. 10 as occurring in a particular order, this disclosure contemplates any suitable steps of the method of FIG. 10 occurring in any suitable order. Moreover, although this disclosure describes and illustrates particular components carrying out particular steps of the method of FIG. 10, this disclosure contemplates any suitable combination of any suitable components carrying out any suitable steps of the method of FIG. 10.

Compression Threshold Analysis of Binary Decision Diagrams

In particular embodiments, sensor network 100 may analyze and monitor the compression rate of a BDD as data is being added to the BDD to determine if using additional bits to encode nodes of the BDD or generating an additional BDD may be used to improve data storage capacity. Although this disclosure describes particular components performing particular processes to analyze and monitor the compression rate of a BDD as data is being added to the BDD to determine if using additional bits to encode nodes of the BDD or generating an additional BDD may be used to improve data storage capacity, this disclosure contemplates using any suitable components and any suitable processes to analyze and monitor the compression rate of a BDD as data is being added to the BDD to determine if using additional bits to encode nodes of the BDD or generating an additional BDD may be used to improve data storage capacity.

In particular embodiments, analysis system 180 may receive one or more data sets for storage as a BDD. In one embodiment, one or more of the data sets may be from one or more data streams from one or more sensors 112 in sensor array 110. Analysis system 180 may then construct a BDD representing the data sets. The BDD may comprise one or more nodes, and each of the one or more nodes may be encoded using n bits. The BDD may be constructed in any suitable manner. As an example and not by way of limitation, analysis system 180 may generate an empty BDD with k bits representing the 0 edges and k bits representing the 1 edges of the BDD. A data set $S^i$ may be represented as a BDD, such as $BDD_S^i$. Analysis system 180 may then apply a logical OR operation to the empty BDD and $BDD_S^i$ to generate a BDD representing the data set. As analysis system 180 receives additional data sets $S^i$, it may iteratively add the data sets to the BDD in any suitable matter. As an example and not by way of limitation, an additional data set $S^{i+1}$ may be represented as another BDD, such as $BDD_S^{i+1}$, and a logical OR operation may be applied to the BDD and $BDD_S^{i+1}$ to yield an updated BDD. Although this disclosure describes constructing a BDD using particular components and particular processes, this disclosure contemplates constructing BDDs using any suitable components and any suitable processes. Furthermore, although this disclosure describes iteratively adding data from one or more data sets to a BDD using particular components and particular processes, this disclosure contemplates iteratively adding data from one or more data sets to a BDD using any suitable components and any suitable processes.

In particular embodiments, analysis system 180 may analyze a BDD to determine the compression rate of the BDD. The compression rate may be defined as the ratio of the space required to store a data set as tuples in consecutive, binary form over the space required to store a BDD representing the data set. Analysis system 180 may analyze the BDD at any suitable time and with any suitable frequency. As an example and not by way of limitation, analysis system 180 may analyze the BDD after each iterative addition of data, at specified time intervals, or at another suitable time. In particular embodiments, analysis system 180 may optimize the size of the BDD before determining its compression rate. As an example and not by way of limitation, analysis system 180 may optimize the size of the BDD using variable reordering. Although this disclosure describes determining the compression rate of a BDD using particular components and particular processes, this disclosure contemplates determining the compression rate of a BDD using any suitable components and any suitable processes.

In particular embodiments, once the compression rate of a BDD drops below a threshold compression rate, analysis system 180 may use additional bits to encode each of the one or more nodes of the BDD. The threshold compression rate for a BDD is the point where the addition of new data sets to the BDD would cause the compression rate of the BDD to substantially decrease. As an example and not by way of limitation, for a BDD with k bits representing the 0 edges and k bits representing the 1 edges of the BDD, the threshold compression rate is when the number of nodes in the BDD is less than or equal to $2^k-1$. As analysis system 180 adds additional data sets to a BDD, the compression rate of the BDD may continue to increase until a certain number of samples have been added to the BDD. Once a certain amount of data has been added to the BDD, all the address space allowed by the current structure of the BDD will be exhausted. In order to continue adding additional data sets to the BDD, analysis system 180 would need to add additional nodes to the BDD, which may cause the compression rate to substantially decrease. As an example and not by way of limitation, a BDD may comprise one or more nodes, and each of the one or more nodes may be encoded using n bits. If the compression rate of the BDD drops below the threshold compression rate, then analysis system 180 may encode each of the one or more nodes of the BDD using n+d bits. This process may be repeated to encode the nodes of the BDD using an additional d bits each time the threshold compression rate of the BDD drops below the threshold compression rate. Although this disclosure describes particular threshold compression rates for particular BDDs, this disclosure contemplates any suitable threshold compression rate for any suitable BDD. Moreover, although this disclosure describes encoding the nodes of a BDD in a particular manner, this disclosure contemplates encoding the nodes of a BDD in any suitable manner.

In particular embodiments, once a (first) BDD reaches a threshold compression rate, analysis system 180 may generate a new (second) BDD to store additional data sets. As an example and not by way of limitation, analysis system 180 may iteratively add data from one or more data sets to the first BDD until the compression rate of the first BDD reaches the threshold compression rate. Analysis system 180 may then stop iteratively adding data to the first BDD and construct a second BDD to store additional data sets. The second BDD may be constructed in any suitable manner. As an example and not by way of limitation, analysis system 180 may generate an empty BDD with k bits representing the 0 edges and k bits representing the 1 edges of the BDD. A data set $S_i$ may be represented as a BDD, such as $BDD_S^i$. Analysis system 180 may then apply a logical OR operation to the empty BDD and $BDD_S^i$ to generate the second BDD. As analysis system 180 receives additional data sets $S^i$, it may iteratively add the data sets to the second BDD in any suitable matter. As an example and not by way of limitation, an additional data set $S^{i+1}$ may be represented as another BDD, such as $BDD_S^{i+1}$, and a logical OR operation may be applied to the second BDD and $BDD_S^{i+1}$ to yield an updated second BDD. In some embodiments, the first BDD and the second BDD may both have k bits representing the 0 edges and k bits representing the 1 edges of the BDD. Although this disclosure describes generating a second BDD once a first BDD reaches a threshold compression rate using particular components and particular processes, this disclosure contemplates generating a second BDD once a first BDD reaches a threshold compression rate using any suitable components and any suitable processes. Furthermore, although this disclosure describes iteratively adding data from one or more data sets to a second BDD using particular components and particular processes, this disclosure contemplates iteratively adding data from one or more data sets to a second BDD using any suitable components and any suitable processes.

Figure 11:
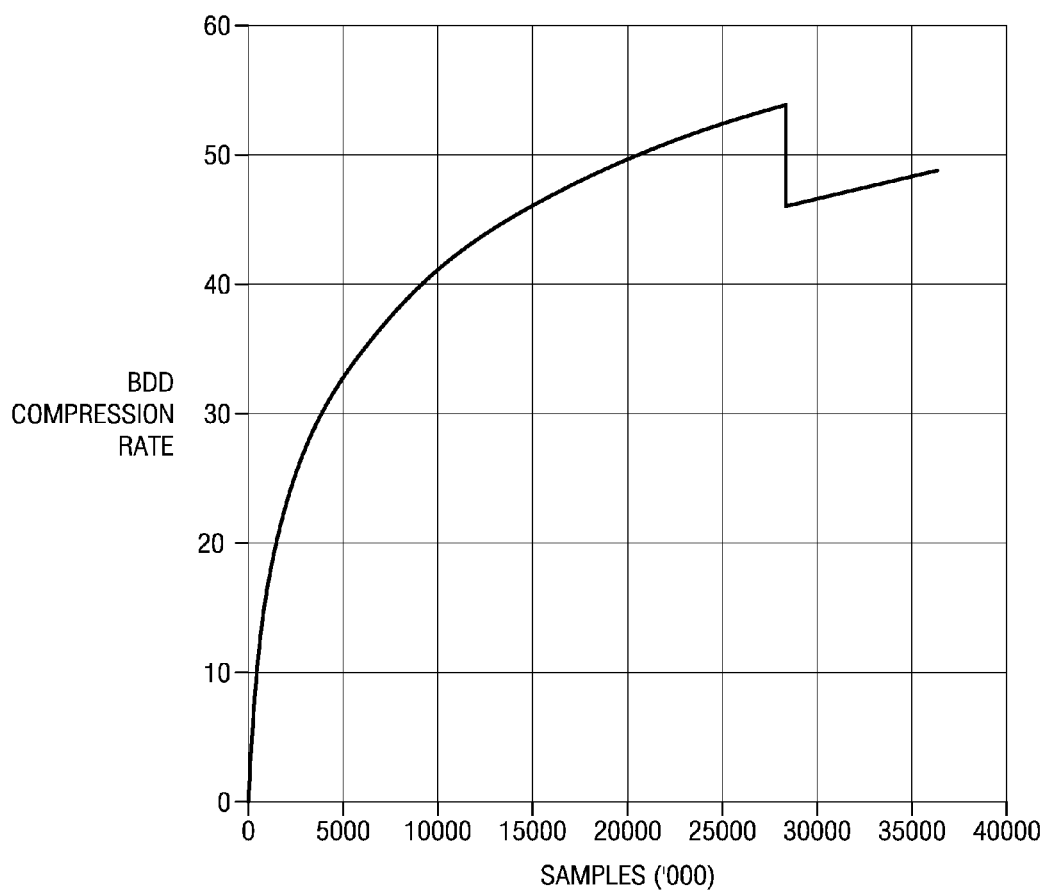
FIG. 11 illustrates an example graph measuring BDD compression rate versus the number of samples represented by the BDD.

FIG. 11 illustrates an example graph measuring BDD compression rate versus the number of samples represented by the BDD. The BDD in this example has nodes that are 6 bits long. As samples are added to the BDD, the compression rate of the BDD increases until it reaches a threshold compression rate. As an example and not by way of limitation, the threshold compression rate illustrated in FIG. 11 occurs at approximately 28 million samples. At this point, the nodes in the BDD are restructured to increases from being 6 bits long to being 7 bits long, which causes the cause the compression rate of the BDD to drop from approximately 54 to 46. Although this disclosure describes and FIG. 11 illustrates a particular relationship between BDD compression rate and the number of samples represented by the BDD, this disclosure contemplates any suitable relationship between BDD compression rate and the number of samples represented by the BDD.

Figure 12:
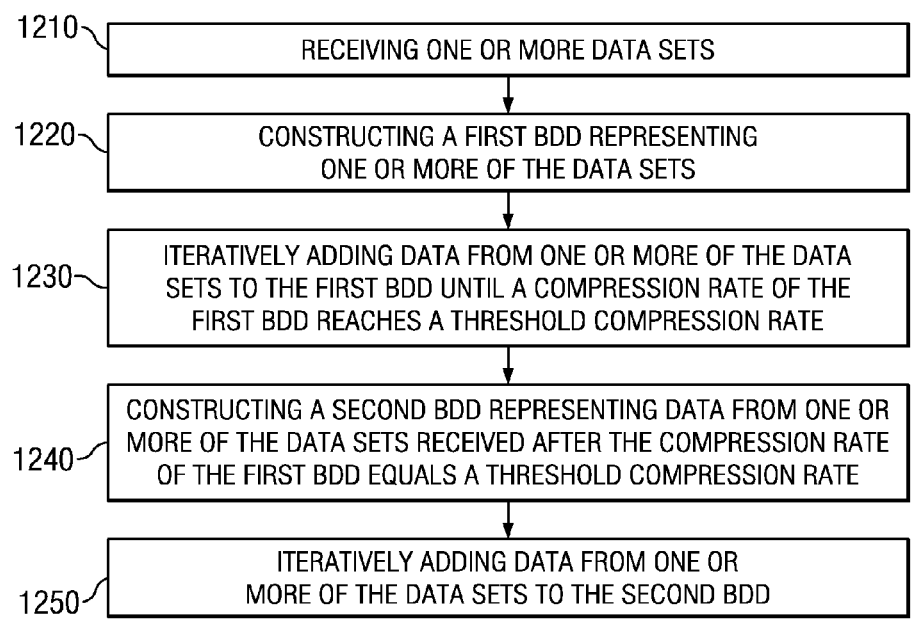
FIG. 12 illustrates an example method for performing a compression threshold analysis on binary decision diagrams.

FIG. 12 illustrates an example method for performing a compression threshold analysis on binary decision diagrams. The method begins at step 1210, where analysis system 180 receives one or more data sets. At step 1220, analysis system 180 constructs a first BDD representing one or more of the data sets. At step 1230, analysis system 180 iteratively adds data from one or more of the data sets to the first BDD until a compression rate of the first BDD reaches a threshold compression rate. At step 1240, analysis system 180 constructs a second BDD representing data from one or more of the data sets received after the compression rate of the first BDD equals a threshold compression rate. At step 1250, analysis system 180 iteratively adds data from one or more of the data sets to the second BDD. Although this disclosure describes and illustrates particular steps of the method of FIG. 12 as occurring in a particular order, this disclosure contemplates any suitable steps of the method of FIG. 12 occurring in any suitable order. Moreover, although this disclosure describes and illustrates particular components carrying out particular steps of the method of FIG. 12, this disclosure contemplates any suitable combination of any suitable components carrying out any suitable steps of the method of FIG. 12.

Detecting Sensor Malfunctions Using Compression Analysis of Binary Decision Diagrams In particular embodiments, sensor network 100 may analyze and monitor the compression rate of a BDD representing a data stream from a sensor 112 to determine if the sensor 112 is malfunctioning. Although this disclosure describes particular components performing particular processes to analyze and monitor the compression rate of a BDD representing a data stream from a sensor to determine if the sensor is malfunctioning, this disclosure contemplates using any suitable components and any suitable processes to analyze and monitor the compression rate of a BDD representing a data stream from a sensor to determine if the sensor is malfunctioning.

In particular embodiments, analysis system 180 may receive one or more data sets for storage as a BDD, construct a BDD representing the data sets, and iteratively add data sets to the BDD as they are received. The BDD may be constructed and data may be iteratively added to the BDD in any suitable manner, including using the components and processes described previously. In one embodiment, one or more of the data sets may be from one or more data streams from one or more sensors 112 in sensor array 110.

In particular embodiments, analysis system 180 may analyze a BDD to determine the compression rate of the BDD. The compression rate may be determined in any suitable manner, including using the components and processes described previously. Analysis system 180 may analyze the BDD at any suitable time and with any suitable frequency. As an example and not by way of limitation, analysis system 180 may analyze the BDD after each iterative addition of data, at specified time intervals, or at another suitable time. Analysis system 180 may also optimize the size of the BDD before determining its compression rate. Optimizing the size of a BDD may be performed using any suitable process, including using the processes described previously.

In particular embodiments, a BDD representing a data stream from a sensor 112 may have a specified compression-rate range, wherein the specified compression-rate range represents the range of BDD compression rates that indicate a sensor 112 is operating as specified (such as, for example, operating normally, as expected, within specifications, etc.). The specified compression-rate range may be based on a variety of factors, such as, for example, the sensor type, the sensor subject, the sensor sample rate, the BDD structure or type, the number of samples stored by the BDD, other suitable factors, or two or more such factors. A compression-rate range has a lower and upper bound. The lower bound is the minimum compression rate in the range, while the upper bound is the maximum compression rate in the range. As an example and not by way of limitation, as BDD may have a specified compression-rate range with a lower bound of 2× and an upper bound of 100×. This range may represent the lower and upper bound of the normal compression rate for a BDD representing a particular data stream from a particular sensor 112.

In particularly embodiments, the specified compression-rate range has a lower bound equal to approximately the compression rate achieved when constructing a BDD representing random noise. The compression rate for random noise (such as, for example, a series of random numbers or white noise) is approximately 2×. As an example and not by way of limitation, the specified compression rate may have a lower bound equal to 2×, 3×, 4×, 5×, 6×, 7×, 8×, 9×, 10×, 15×, 20×, 25×, 30×, 35×, 40×, 45×, 50×, or another suitable compression rate. If a sensor 112 is malfunctioning, it may begin transmitting incorrect or random values, which may cause the compression rate of the BDD to decline.

In particular embodiments, the specified compression-rate range has an upper bound equal to approximately the compression rate achieved when constructing a BDD representing a single continuously repeating number. The compression rate for a single repeating number depends on the number of samples received, will continuously increase with no upper bound. As an example and not by way of limitation, the specified compression rate may have an upper bound equal to 5×, 6×, 7×, 8×, 9×, 10×, 15×, 20×, 25×, 30×, 35×, 40×, 45×, 50×, 60×, 70×, 80×, 90×, 100×, 200×, 300×, 400×, 500×, or another suitable compression rate. If a sensor 112 is malfunctioning, it may begin transmitting the same value regularly, repetitively, or continuously for unusually long periods of time. A BDD storing this data may have an abnormally large compression rate that is significantly higher than the compression rate found for a typical data stream from the sensor 112, which may indicate that the data is invalid or faulty. As an example and not by way of limitation, if heart-rate monitor outputs a heart-rate of 60 bpm for 16 hours, analysis system 180 may generate a single node BDD with a high compression rate that exceeds the upper bound of the specified compression-rate range for the heart-rate monitor.

In particular embodiments, analysis system 180 may indicate a sensor malfunction in a sensor 112 if the compression rate of a BDD representing a data stream from the sensor 112 deviates from a specified compression-rate range. A sensor malfunction may be indicated if the compression rate of the BDD either drops below the lower bound or rises above the upper bound of the specified compression-rate range. A sensor malfunction may be caused by a variety of factors. As an example and not by way of limitation, sensor malfunctions may include: transmission of invalid data sets from the sensor 112 (for example, if the data is corrupted during transmission); receipt of invalid stimulus by the sensor 112 (for example, if the sensor 112 become detached from the subject); a software error in a component of sensor network 100; a hardware malfunction in the sensor 112; another suitable malfunction; or two or more such malfunctions. Analysis system 180 may determine the type of the sensor malfunction using any suitable process.

In particular embodiments, analysis system 180 may differentiate between BDD compression rate changes caused by a sensor malfunctions and changes caused by a subject's activity. As an example and not by way of limitation, if a subject starts exercising, an EKG sensor worn by the subject may begin outputting a heart wave with a shortened periodicity. However, the shape of the heart wave will generally be the same and should stabilize at some point. The specified compression-rate range for a BDD may be set to account for these normal or expected deviations in BDD compression rate cause by a subject's activity.

In particular embodiments, after indicating a sensor malfunction in a first sensor 112 in sensor array 110, analysis system 180 may analyze a BDD representing a data stream from a second sensor 112 in sensor array 110 to verify that the first sensor 112 is truly malfunctioning. If the compression rate of the BDD representing the data stream from the first sensor 112 deviates from the specified compression-rate range, it may indicate that the data stream is abnormal and the first sensor 112 is malfunctioning, but it may be desirable to corroborate or verify that first sensor 112 is malfunctioning before sounding an alarm or transmitting the indication to display system 190. As an example and not by way of limitation, analysis system 180 may access a (second) BDD representing a data stream from a second sensor 112 in sensor array 112 and analyze the second BDD to determine the compression rate of the BDD. The second BDD may have a specified compression-rate range representing the range of BDD compression rates that indicate the second sensor 112 is operating as specified. If the compression rate of the second BDD is within the specified compression-rate range, analysis system 180 may verify the indication of a sensor malfunction with respect to the first sensor 112. However, if the compression rate of the second BDD is not within the specified compression-rate range, analysis system 180 may negate the indication of a sensor malfunction with respect to the first sensor 112. In the latter case, where both the first and second BDDs deviate from their specified compression-rate ranges, analysis system 180 may not be able to determine if there is an actual sensor malfunction. For example, both the first and second sensors 112 may be malfunctioning. Alternatively, analysis system 180 could be malfunctioning. Analysis of other BDDs representing other data streams from other sensors 112 in sensor array 110 may be performed to verify the sensor malfunctions.

In particular embodiments, analysis system 180 may analyze a BDD to determine the rate of change of the compression rate of the BDD. The rate of change of the compression rate may be determined in any suitable manner, including using components and processes described previously. Analysis system 180 may then indicate a sensor malfunction in a sensor 112 if the compression rate of a BDD representing a data stream from the sensor 112 deviates from a specified rate of change of compression-rate range. A sensor malfunction may be indicated if the rate of change of the compression rate of the BDD either drops below the lower bound or rises above the upper bound of the specified rate of change of compression-rate range. As an example and not by way of limitation, a BDD with a compression rate that is changing rapidly may be indicative of a sensor malfunction.

Indications of a sensor malfunction may be reported in any suitable manner. As an example and not by way of limitation, the indication of a sensor malfunction may be displayed on display system 190.

Figure 13:
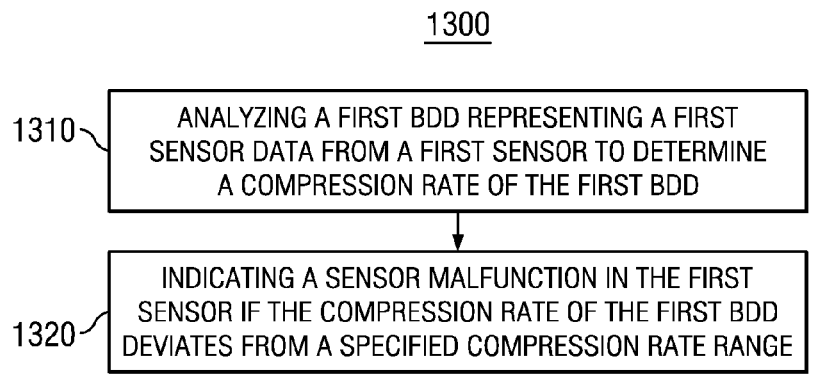
FIG. 13 illustrates an example method for detecting sensor malfunctions using compression analysis of binary decision diagrams.

FIG. 13 illustrates an example method for detecting sensor malfunctions using compression analysis of binary decision diagrams. The method begins at step 1310, where analysis system 180 analyzes a first BDD representing a first data stream from a first sensor 112 to determine a compression rate of the first BDD. At step 1320, analysis system 180 indicates a sensor malfunction in the first sensor 112 if the compression rate of the first BDD deviates from a specified compression-rate range. Although this disclosure describes and illustrates particular steps of the method of FIG. 13 as occurring in a particular order, this disclosure contemplates any suitable steps of the method of FIG. 13 occurring in any suitable order. Moreover, although this disclosure describes and illustrates particular components carrying out particular steps of the method of FIG. 13, this disclosure contemplates any suitable combination of any suitable components carrying out any suitable steps of the method of FIG. 13.

Detecting Data Corruption in Medical Binary Decision Diagrams Using Hashing Techniques In particular embodiments, data corruption may be detected in BDDs representing one or more data streams from one or more sensors by using various hashing techniques. Although this disclosure describes detecting data corruption in BDDs using particular components, this disclosure contemplates detecting data corruption in BDDs using any suitable components. Furthermore, although this disclosure describes particular hashing techniques, this disclosure contemplates using any suitable hashing techniques.

In particular embodiments, a first component of sensor network 100 may access a first instance of a BDD and transform the first instance of the BDD to a first arithmetic function by performing an arithmetic transformation on the first instance of the BDD. In one embodiment, the first instance of the BDD may represent one or more data sets from one or more data streams from one or more sensors 112 in sensor array 110. A BDD may be transformed in any suitable manner. As an example and not by way of limitation, the arithmetic transformation may be performed according to one or more of the following rules:

X AND Y→X×Y
X OR Y→X+Y−X×Y
NOT(X)→1−X
X AND X (idempotence)→X×X=X; $X^k$=X

A "→" represents "is transformed to", AND represents a logical AND, OR represents a logical OR, NOT represents a logical negation, X AND X represents idempotence, × represents multiplication, + represents addition, and a superscript represents an exponent. As an example and not by way of limitation, if Boolean function $f$=X OR Y, then the arithmetic function A[$f$]=X+Y−X×Y. In particular embodiments, if the finite integer field has a size p, the arithmetic is performed modulo p. Although this disclosure describes transforming a BDD to an arithmetic function using particular processes, this disclosure contemplates transforming a BDD to an arithmetic function using any suitable processes.

In particular embodiments, a first hash code may be generated by a first component of sensor network 100 by calculating the first hash code from the first arithmetic function and an input. Any suitable input may be used. In particular embodiments, the input may be randomly generated integers. As an example and not by way of limitation, if input X=5 and Y=7 is provided to arithmetic function A[$f$]=X+Y−X×Y, then the hash code is A[$f$]=5+7−5×7=−23. In particular embodiments, a hash code H may be determined for a logical combination of Boolean functions $f^1$ and $f^2$. Hash code H may be determined from an arithmetic combination of hash codes $H^1$ and $H^2$, where $H^1$ is the hash code of Boolean function $f^1$ and $H^2$ is the hash code of Boolean function $f^2$. In particular embodiments, the theorem of orthogonality may be applied. If Boolean functions $f^1$ and $f^2$ do not overlap in time, then hash code H for $f^1 \vee f^2 = H^1 + H^2 = H$. Although this disclosure describes generating hash codes using particular processes, this disclosure contemplates generating hash codes using any suitable processes.

In particular embodiments, the first component of sensor network 100 may then transmit the first instance of the BDD, the first hash code, and the input to a second component of sensor network 100. Because the first instance of the BDD may be corrupted during transmission, the second component of sensor network 100 cannot assume that the data is received is identical to the first instance of the BDD transmitted by the first component of sensor network 100. Therefore, for purposes of illustration and not by way of limitation, the data representing the first instance of the BDD received by the second component of sensor network 100 will be referred to as the second instance of the BDD. The second component of sensor network 100 may then access the second instance of the BDD and transform the second instance of the BDD to a second arithmetic function by performing an arithmetic transformation on the second instance of the BDD. The second instance of the BDD may be transformed in any suitable manner. The input may then be provided to the second arithmetic function to generate a second hash code. The second hash code may be generated in any suitable manner.

In particular embodiments, the second component of sensor network 100 may then compare the first hash code and the second hash code. Hash codes of equivalent functions are the same, and hash codes of different functions are probably different. Thus, the equivalence of two functions may be verified with a very low probability of error. If arithmetic expressions are evaluated in a finite integer field under randomization, then any distinct pair of $2^{2^n}$ Boolean functions almost always maps to distinct hash codes, where n is the number of inputs. The probability of error q is n/(size-of-integer-field), where integer field $Z_p=\{0,1, \ldots, p-1\}$ and where p is a prime. As prime p increases, the probability of error q decreases and may approach 0. Accordingly, a larger prime p may be selected to yield more accurate hash codes, and a smaller prime p may be selected to yield less accurate hash codes. In particular embodiments, hash codes may be repeatedly generated to improve accuracy. If hash codes are generated for k runs, then the probability of error is $q \leq (n/p)^k$. Therefore, the probability of error decreases exponentially after each run.

In particular embodiments, if the first hash code equals the second hash code, then the second component of sensor network 100 may indicate that second instance of the BDD contains uncorrupted data (i.e., the first instance of the BDD and the second instance of the BDD are equivalent). However, if the first hash code does not equal the second hash code, then the second component of sensor network 100 may indicate that the second instance of the BDD contains corrupted data (i.e., the first instance of the BDD and the second instance of the BDD are not equivalent). In particular embodiments, if the second component of sensor network 100 indicates that the second instance of the BDD contains corrupted data, it may indicate that the BDD was corrupted during transmission from the first component of sensor network 100. The comparison results of the hash codes may be reported in any suitable manner. As an example and not by way of limitation, the comparison results may be displayed on display system 190. In particular embodiments, analysis system 180 may store the second instance of the BDD if it determines it contains uncorrupted data, and may deleted the second instance of the BDD if it determines it contains corrupted data.

In particular embodiments, if the first hash code does not equal the second hash code, then the second component of sensor network 100 may transmit a request to the first component of sensor network 100 to resend the first instance of the BDD and the first hash code. The first component of sensor network 100 may then retransmit the first instance of the BDD, the first hash code, and the input. For purposes of illustration and not by way of limitation, the data representing the first instance of the BDD re-received by the second component of sensor network 100 will be referred to as the third instance of the BDD. The second component of sensor network 100 may then transform the third instance of the BDD to a third arithmetic function by performing an arithmetic transformation on the third instance of the BDD. The second component of sensor network 100 may then calculate a third hash code from the third arithmetic function and the input. The second component of sensor network 100 may then compare the first and third hash codes. If the first hash code equals the third hash code, then the second component of sensor network 100 may indicate that third instance of the BDD contains uncorrupted data. However, if the first hash code does not equal the third hash code, then the second component of sensor network 100 may indicate that the third instance of the BDD contains corrupted data. If the second component of sensor network 100 has twice indicated that the BDD is corrupted data, it may indicate that BDD was corrupted prior to transmission rather than during transmission. For example, the BDD stored on the first component of sensor network 100 may be corrupt. In particular embodiments, if the first hash code does not equal the third hash code, then the second component of sensor network 100 may indicate that the BDD was corrupted prior to transmission.

In particular embodiments, hash codes may be used to verify communication of Boolean functions or BDDs over one or more communication links (such as, for example, one or more connections 116). As an example and not by way of limitation, sensor array 110 may transmit a BDD and one or more hash codes generated from the BDD over a connection 116 to analysis system 180. In one embodiment, the hash codes are encrypted. Multiple hash codes may be sent or the same hash code may be sent multiple times. Analysis system 180 may calculate a hash code for the received BDD and compare the calculated hash code with the hash code received with the BDD. If the hash codes are the same, analysis system 180 may determine that the received BDD is valid (i.e., has been properly received). Otherwise, analysis system 180 may determine that the received BDD is not valid (i.e., has not been properly received and may have been corrupted). Although this disclosure describes verifying communication of Boolean functions or BDDs with hash codes using particular components and particular processes, this disclosure contemplates verifying communication of Boolean functions or BDDs with hash codes using any suitable components and any suitable processes.

In particular embodiments, hash codes may be used to mark and later validate data stored as Boolean functions or BDDs in a component of sensor network 100. As an example and not by way of limitation, analysis system 180 may calculate a first hash code from a first instance of the BDD and an input, and then may store the first instance of the BDD and the first hash code separately. At a later time, analysis system 180 may validate the stored BDD using the stored hash function. Because the first instance of the BDD may be corrupted during storage, the analysis system 180 cannot assume that the stored data accessed at a later time is identical to the first instance of the BDD when it was originally stored by analysis system 180. Therefore, for purposes of illustration and not by way of limitation, the data representing the first instance of the BDD stored by analysis system 180 will be referred to as the second instance of the BDD. Analysis system 180 may access the second instance of the BDD and calculate a second hash code from the second instance of the BDD and the input. The second hash code may then be compared with the stored first hash code. If the first and second hash codes are the same, the second instance of the BDD may be regarded as valid or uncorrupted data. Otherwise, the second instance of the BDD may be regarded as invalid or corrupted data. More accurate hash codes may be used to mark more important data, and less accurate hash codes may be used to mark less important data. As an example and not by way of limitation, less accurate hash codes may be used if processing power is limited, such as for storage in mobile phones. Although this disclosure describes validating data stored as Boolean functions or BDDs with hash codes using particular components and particular processes, this disclosure contemplates validating data stored as Boolean functions or BDDs with hash codes using any suitable components and any suitable processes.

Figure 14:
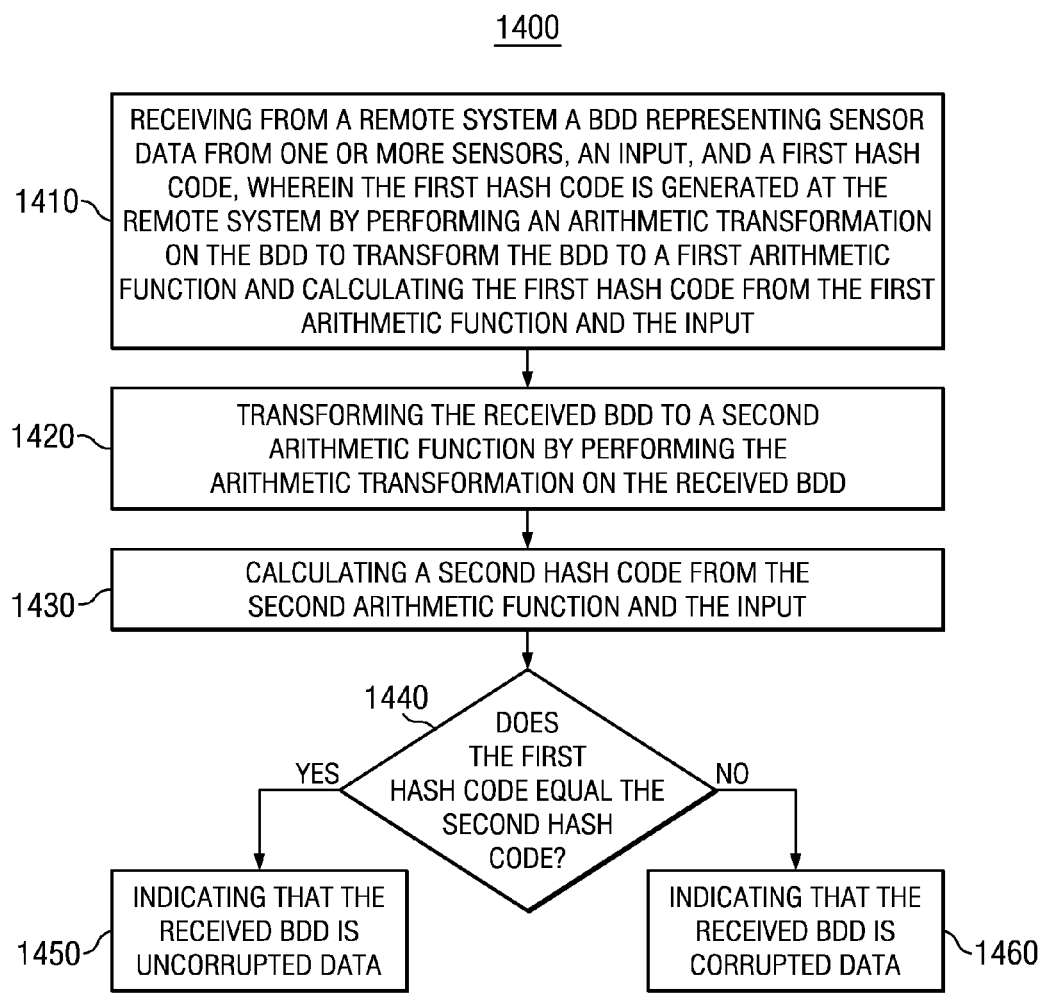
FIG. 14 illustrates an example method for detecting data corruption in medical binary decision diagrams using hashing techniques.

FIG. 14 illustrates an example method for detecting data corruption in medical binary decision diagrams using hashing techniques. The method begins at step 1410, where analysis system 180 receives from a remote system (such as, for example, sensor array 110) a BDD representing one or more data streams from one or more sensors 112, an input, and a first hash code, wherein the first hash code is generated at the remote system by performing an arithmetic transformation on the BDD to transform the BDD to a first arithmetic function and calculating the first hash code from the first arithmetic function and the input. At step 1420, analysis system 180 transforms the received BDD to a second arithmetic function by performing the arithmetic transformation on the received BDD. At step 1430, analysis system 180 calculates a second hash code from the second arithmetic function and the input. At step 1440, analysis system 180 determine if the first hash code equal the second hash code. If the first hash code equal the second hash code, analysis system 180 indicates that the received BDD is uncorrupted data at step 1450. But if the first hash code does not equal the second hash code, analysis system 180 indicates that the received BDD is corrupted data at step 1460. Although this disclosure describes and illustrates particular steps of the method of FIG. 14 as occurring in a particular order, this disclosure contemplates any suitable steps of the method of FIG. 14 occurring in any suitable order. Moreover, although this disclosure describes and illustrates particular components carrying out particular steps of the method of FIG. 14, this disclosure contemplates any suitable combination of any suitable components carrying out any suitable steps of the method of FIG. 14.

Range Queries in Binary Decision Diagrams

In particular embodiments, sensor network 100 may query data within a specified range, wherein the data is represented by one or more BDDs. Although this disclosure describes querying BDDs using particular components, this disclosure contemplates querying BDDs using any suitable components. Furthermore, although this disclosure describes querying BDDs using particular processes, this disclosure contemplates querying BDDs using any suitable processes.

In particular embodiments, analysis system 180 may receive one or more queries for data in one or more data sets that are within a specified range. A query may have any suitable format. In particular embodiments, the query may indicate one or more requested values or ranges of values of one or more data parameters, and may request retrieval of samples that satisfy the request. Any suitable data parameters may be used. As an example and not by way of limitation, suitable data parameters include sensor subject, sensor type, sample value, sample times, and other suitable parameters. A data set S may be represented as a Boolean function, such as $f^S$, or represented as a BDD, such as $BDD_S$. In one embodiment, one or more of the queried data sets may be from one or more data streams from one or more sensors 112 in sensor array 110.

In particular embodiments, analysis system 180 may construct a query BDD representing the specified range (such as, for example, a time range or a sensor output range). As an example and not by way of limitation, the query may be represented by a query function $f_R$. Analysis system 180 may receive the query function $f_R$ directly, or it may generate is from any suitable query. The query function $f_R$ may be formulated in any suitable manner. The query function $f_R$ may be used to identify samples (represented by a BDD) that have the requested values. In particular embodiments, each requested value may be expressed as a requested minterm, and the query function $f_R$ may be formulated from the requested minterms. As an example and not by way of limitation, if a query requests values of $\vec{t}=128$ through 255, then the query function is $f_R(\vec{t}; \vec{s}^1; \ldots ; \vec{s}^N) = \bar{t}_{31}\bar{t}_{30}\ldots \bar{t}_8 t_7$. Analysis system 180 may then construct a BDD representing the query function $f_R$, such as, for example, $BDD_R$. The query BDD may be constructed in any suitable manner. In particular embodiments, $BDD_R$ evaluates to 1 for all values in the specified range and evaluates to 0 for all values not in the specified range. As an example and not by way of limitation, if $BDD_R$ represents a range [a,b], then $BDD_R$ may be constructed by first constructing $BDD_L$ representing range [a,max] and BDD representing [b+1,max]. Analysis system 180 may then apply a logical AND operation to $BDD_L$ and NOT($BDD_U$) to generate $BDD_R$. As another example and not by way of limitation, the query function $f_R$ may represent range [α,max] and be equal to the Boolean function $f_a(\vec{v})$, which evaluates to 1 when the number represented by vector $\vec{v}$ is equal to or larger than value a. A BDD representing $f_a(\vec{v})$ may be computed by an algorithm described by the following pseudocode:

```
BDD threshold(value, bits)
{
        result = 1
        while(bits>0)
        {
                bits = bits − 1
                if(value mod 2 = 1)
                        result = result AND var_bits
                else
                        if(result <> 1)
                                result = result OR var_bits
                value = value / 2
        }
        return result
}
```

In the pseudocode above, bits is the size of vector $\vec{v}$, value is equal to α, and $var_j$ is a BDD representing the $j^{th}$ variable. More specifically, $var_j$ is a BDD representing Boolean function $F_j(\vec{v})$, which always evaluates to 1 except when $v_j=0$.

In some embodiments, the top n layers of $BDD_S$ correspond to n variables representing the specified range. The query BDD may be specified in terms of the top n variables of $BDD_S$. As an example and not by way of limitation, $BDD_S$ may have in total layers, wherein the top n layers correspond to n variables representing the specified range, wherein n and the top n of the in layers in $BDD_S$ correspond, respectively, to the n of the in variables in the query BDD. Analysis system 180 may generate a $BDD_R$ that also has n layers corresponding to n variables representing the specified range. In one embodiment, analysis system 180 may reorder one or more variables of $BDD_S$ such that the top n of the in layers of BDDs correspond, respectively, to the n of the m variables representing the specified range in the query. As an example and not by way of limitation, analysis system 180 may reorder BDD variables using plain changes algorithm, sifting algorithm, window algorithm, parallel permutation algorithm, optimum layer-swapping schedules for BDDs with four variables, pair-wise grouping of BDD variables, recursive separation of BDD variables, parallel window algorithm, window algorithm using maximal parallelization, parallel sifting algorithm, another suitable reordering process, or two or more such processes. In alternative embodiments, $BDD_S$ representing one or more data sets S may have m layers corresponding, respectively, to m variables and k nodes corresponding to m variables, each of the m layers having one or more of the k nodes. Analysis system 180 may generate a $BDD_R$ that represents a specified range in a query received by analysis system 180. The specified range represented by $BDD_R$ corresponds to n of the m variables, wherein m≥n. In $BDD_S$, j of the k nodes corresponding to the n of the m variables in the specified range are at the top n of the m layers of $BDD_S$. In particular embodiments, a $BDD_S$ may represent one or more sensor data sets S from one or more sensors, where the sensor data are time specific. The query BDD may be specified in terms of a time range. $BDD_S$ may have m variables, and i of the m variables may correspond to time data associated with the sensor data, where m>i, and j of the m variables may correspond to sensor data, where m>j. Although this disclosure describes constructing a query BDD using particular components and particular processes, this disclosure contemplates constructing a query BDD using any suitable components and any suitable processes.

In particular embodiments, analysis system 180 may construct a (third) BDD representing the data in the specified range using the query BDD and the BDD representing the data set. The third BDD may identify one or more samples that have the one or more requested values. As an example and not by way of limitation, $BDD_R$ and $BDD_S$ may be used to yield search results. $BDD_R$ and $BDD_S$ may be used in any suitable manner. In particular embodiments, $BDD_R$ and $BDD_S$ may be logically combined by applying a logical operation (such as a logical AND operation) to the BDDs. Applying a logical AND operation to a number of operands may yield the logical AND of the operands. As an example and not by way of limitation, analysis system 180 may apply a logical AND operation to $BDD_R$ and $BDD_S$ to generate a third BDD representing the queried data. The third BDD represents the results of the query, and may represent one or more samples that have the requested values or may represent the number of samples that have the requested values. If no samples fall with the specified range, analysis system 180 may generate a third BDD that is empty. The search results may be reported in any suitable manner. As an example and not by way of limitation, the search results may be displayed on display system 190.

Figure 15:
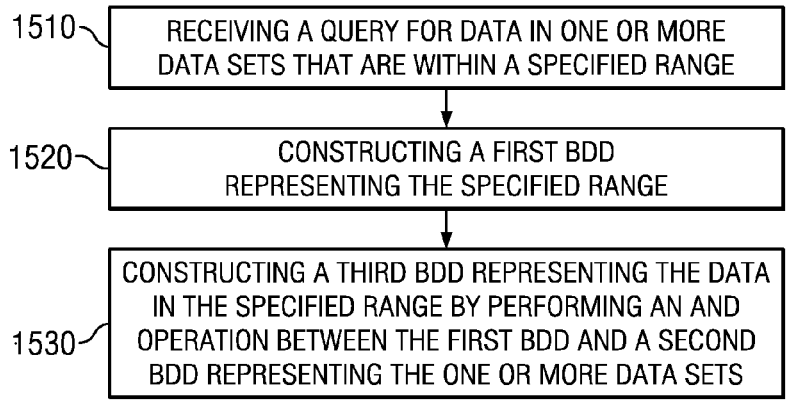
FIG. 15 illustrates an example method for querying data within a specified range in binary decision diagrams.

FIG. 15 illustrates an example method for querying data within a specified range in binary decision diagrams. The method begins at step 1510, where analysis system 180 receives a query for data in one or more data sets that are within a specified range. At step 1520, analysis system 180 constructs a first BDD representing the specified range. At step 1530, analysis system 180 constructs a third BDD representing the data in the specified range by performing an AND operation between the first BDD and a second BDD representing the one or more data sets. Although this disclosure describes and illustrates particular steps of the method of FIG. 15 as occurring in a particular order, this disclosure contemplates any suitable steps of the method of FIG. 15 occurring in any suitable order. Moreover, although this disclosure describes and illustrates particular components carrying out particular steps of the method of FIG. 15, this disclosure contemplates any suitable combination of any suitable components carrying out any suitable steps of the method of FIG. 15.

Annotating Medical Binary Decision Diagrams with Health State Information

In particular embodiments, sensor network 100 may annotate sensor data represented by a BDD with health state information. Although this disclosure describes annotating BDDs using particular components, this disclosure contemplates annotating BDDs using any suitable components. Furthermore, although this disclosure describes annotating BDDs using particular processes, this disclosure contemplates annotating BDDs using any suitable processes.

In particular embodiments, analysis system 180 may construct a model BDD representing a plurality of health states. Analysis system 180 may generate the model BDD from model sensor data. Model sensor data is sensor data that includes one or more specified data ranges of sensor values, wherein each specified data range of sensor values is associated with one or more health states, and one or more annotations for each specified data range of sensor values of the associated health states. Model sensor data may be used to annotate sensor data obtained from one or more sensors 112 in order to categorize the data. As an example and not by way of limitation, certain model sensor data may be categorized and annotated with a "normal" (or similar) annotation, while other sensor data may be categorized and annotated with an "abnormal" (or similar) annotation. Sensor data obtained from measurements that match the normal model sensor data may be categorized as normal, while measured sensor data that match abnormal model sensor data may be categorized as abnormal. Any suitable annotation may be used.

In particular embodiments, medical annotations may be used to categorize medical sensor data. As an example and not by way of limitation, medical annotations may include a "normal" annotation for normal medical sensor data and an "abnormal" annotation for abnormal medical sensor data. Any suitable medical annotation may be used. Medical annotations may include annotations for particular diseases, conditions, symptoms, severity, other suitable medical annotations, or two or more such medical annotations.

As an example and not by way of limitation, analysis system 180 may use medical annotations related to a plurality of insulin resistance grades. Analysis system 180 may use a variety of scales, both qualitative and quantitative, for assessing the severity of insulin resistance in a person. For example, a scale could grade insulin resistance severity on a scale of 0 to 100, wherein 0 is no insulin resistance and 100 is complete insulin resistance.

As another example and not by way of limitation, analysis system 180 may use medical annotations related to a plurality of musculoskeletal pathology grades. The degree of musculoskeletal pathology may be assessed both by the number of symptoms present and their intensity. Analysis system 180 may use a variety of scales, both qualitative and quantitative, for assessing the severity of musculoskeletal pathology in a person. As an example and not by way of limitation, a user may report both muscle pain and weakness. A simple five point scale may be devised to quantitate the intensity of the various symptoms. Another user may report muscle cramping and weakness and yet another user may report all three symptoms. Each symptom may be scored for intensity and then algorithmically combined into a composite scale that could describe the degree of musculoskeletal pathology. As an example and not by way of limitation, a scale could grade musculoskeletal pathology severity on a scale of 0 to 100, wherein 0 is no activity level or range of motion degradation and 100 is severe muscle pain with any movement. Analysis system 180 may also use different scales for different types of musculoskeletal pathology. As an example and not by way of limitation, a first scale could be used to grade myopathy severity, and a second scale could be used to grade arthritis severity.

As yet another example and not by way of limitation, analysis system 180 may use medical annotations related to a plurality of dyspnea grades. Analysis system 180 may reference the MRC Breathlessness Scale to annotate specified data ranges of sensor data with a dyspnea grade. The scale provides five different grades of dyspnea based on the circumstances in which it arises:

| Grade | Degree of Dyspnea |
|---|---|
| 0 | no dyspnea except with strenuous exercise |
| 1 | dyspnea when walking up an incline or hurrying on a level surface |
| 2 | dyspnea after 15 minutes of walking on a level surface |
| 3 | dyspnea after a few minutes of walking on a level surface |
| 4 | dyspnea with minimal activity such as getting dressed |

Analysis system 180 may also use variations of the MRC Breathlessness Scale, or other scales, both qualitative and quantitative, for assessing the severity of dyspnea in a person. For example, an alternative scale could grade dyspnea severity on a scale of 0 to 100, allowing for more refined a more precise diagnosis of a person's dyspnea.

As yet another example and not by way of limitation, analysis system 180 may use medical annotations related to a plurality of stress grades. Analysis system 180 may use a variety of scales, both qualitative and quantitative, for assessing the stress level in a person. As an example and not by way of limitation, analysis system 180 could grade the stress level of a person on a 0-to-4 Liker scale, where the five-level Likert item may be:

0. Very unstressed
1. Moderately unstressed
2. Neither stressed nor unstressed
3. Moderately stressed
4. Very stressed Other suitable Likert items may be used. The Likert items may be analyzed as interval-level data or as ordered-categorical data. As another example and not by way of limitation, analysis system 180 could grade the stress level on a scale of 0 to 100, wherein 0 is the user's baseline stress when relaxed and resting and 100 is the user's maximum stress.

Although this disclosure describes annotating BDDs with particular annotations, this disclosure contemplates annotating BDDs with any suitable annotations. Moreover, although this disclosure describes annotating BDDs with annotations for particular health states, this disclosure contemplates annotating BDDs with annotations for any suitable health states.

In particular embodiments, analysis system 180 may access one or more sets A of model sensor data. Each set comprises model samples for a corresponding annotation of one or more annotations $a_i$. A model sensor data set $A_i$ may be represented as a Boolean function, such as $f^{a_i}$, or as a BDD, such as $BDD_{Ai}$. In particular embodiments, analysis system 180 may generate an annotation function $f^{a_i}$ for each annotation $a_i$. The annotation function $f^{a_i}$ represents model samples annotated with one or more health state annotations. The annotation function $f^{a_i}$ may be used to annotate measured samples in specified ranges with health state information. The annotation function $f^{a_i}$ may be generated in any suitable manner. In particular embodiments, each model sensor data set $A_i$ may be represented as a set of model minterms, and the annotation function $f^{a_i}$ may be generated from the model minterms, for example, by applying a logical operation (such as a logical OR operation) to the minterms. The annotation function $f^{a_i}$ indicates whether a given minterm is a member of the model minterms. As an example and not by way of limitation, samples from a particular sensor may be represented by minterms with 32 variables allocated for time and 8 variables allocated for the sensor measurements. Analysis system 180 may annotate the $k^{th}$ sensor values [64,127] at times [0,31] with the "normal" attribute using the following annotation function: $f^{a_{normal}}(\vec{t};\vec{s}^1;\ldots;\vec{s}^k) = \bar{t}_{31}\bar{t}_{30}\ldots\bar{t}_6\bar{t}_5 s_7^k s_6^k$. In particular embodiments, a model function $f^m$ representing model sensor data may be annotated to yield an annotation function $f^{a_i}$. The annotation function $f^{a_i}$ may be annotated in any suitable manner. In particular embodiments, a Boolean variable is used to represent an annotation $a_i$. A mathematical operation (such as the product operation) may be applied to the Boolean variable a, and the model function $f^m$ to yield the annotation function $f^{a_i}$. Analysis system 180 may then construct a BDD representing the annotation function, such as, for example, $BDD_{Ai}$. The annotation BDD may be constructed in any suitable manner. In particular embodiments, $BDD_{Ai}$ may be generated directly from the model minterms and suitable annotation information associating specified data ranges with particular annotations. Although this disclosure describes constructing an annotation BDD using particular components and particular processes, this disclosure contemplates constructing an annotation BDD using any suitable components and any suitable processes.

In particular embodiments, analysis system 180 may generate a general annotation function g representing one or more annotation functions $f^{a_i}$. The general annotation function g may be generated in any suitable manner. In particular embodiments, a logical operation (such as a logical OR operation) may be applied to one or more annotation functions $f^{a_i}$ to yield a general annotation function: $g(\vec{a};\vec{t};\vec{s}_1;\ldots;\vec{s}^k) = \bigvee_i f^{a_i}$. In particular embodiments, a logical operation (such as a logical OR operation) may be applied to one or more annotation BDDs, such as $BDD_{Ai}$ to yield a general annotation BDD, such as $BDD_G$.

In particular embodiments, analysis system 180 may annotate a function $f^S$ representing samples of sensor data using the general annotation function g. The samples may be annotated in any suitable manner. In particular embodiments, $f^S$ and g may be logically combined by applying a logical operation (such as a logical AND operation) to the functions. Applying a logical AND operation to a number of operands may yield the logical AND of the operands. As an example and not by way of limitation, analysis system 180 may generate an annotated function $f^Q$ representing samples of function $f^S$ annotated with annotations by performing the following operation: $f^Q = f^S \cdot g$. The annotated function $f^Q$ may be represented by a BDD, such as $BDD_Q$.

In particular embodiments, analysis system 180 may annotate a BDD representing samples of sensor data, such as $BDD_S$, using a general annotation BDD, such as $BDD_G$. The samples may be annotated in any suitable manner. In particular embodiments, $BDD_S$ and $BDD_G$ may be logically combined by applying a logical operation (such as a logical AND operation) to the functions. Applying a logical AND operation to a number of operands may yield the logical AND of the operands. As an example and not by way of limitation, analysis system 180 may generate an annotated binary decision diagram $BDD_Q$ by performing an AND operation between $BDDs$ and $BDD_G$, wherein $BDD_Q$ represents the sensor data represented by $BDD_S$ and wherein sensor data in specified ranges that are associated with a health state are annotated with a health state annotation. The annotated sensor data may be reported in any suitable manner. As an example and not by way of limitation, the annotated sensor data may be displayed on display system 190.

In particular embodiments, analysis system 180 may perform one or more subsequent operations on annotated function $f^Q$ or annotated binary decision diagram $BDD_Q$. As an example and not by way of limitation, $BDD_Q$ may be queried to identify samples that have a particular annotation. The query may be performed in any suitable manner, such as, for example, by logically combining $BDD_Q$ with a query binary decision diagram $BDD_R$ by applying a logical operation (such as a logical AND operation) to the BDDs. The search results may be reported in any suitable manner.

In particular embodiments, analysis system 180 may annotate a data set S from a data stream that exhibits some type of deviation, variability, or change from other data sets in the data stream. The data set S may be represented as a Boolean function, such as $f^S$, or represented as a BDD, such as $BDD_S$. As an example and not by way of limitation, a subject may be wearing a heart-rate monitor and an accelerometer, which transmit a heart-rate data stream and an accelerometer data stream, respectively. This system may be used to monitor physiological data steams and to annotate the data streams to indicate data sets indicating the subject has an abnormal heart-rate. For example, a data set in the heart-rate data stream may show the subject had an elevated heart-rate during a certain time period. A data set in the accelerometer data stream may show the subject had an elevated activity during the same time period. By mapping and comparing these data sets, analysis system 180 may annotate the data streams. For example, an elevated heart-rate that coincides with increased activity is typically a normal response. However, a spike in heart-rate that coincides with a marginal elevated physical activity may not be a normal response. Analysis system 180 could then determine, based on the comparison, whether certain levels of activity produce abnormal heart-rate spikes in the subject and annotate that sensor data as "abnormal."

Figure 16:
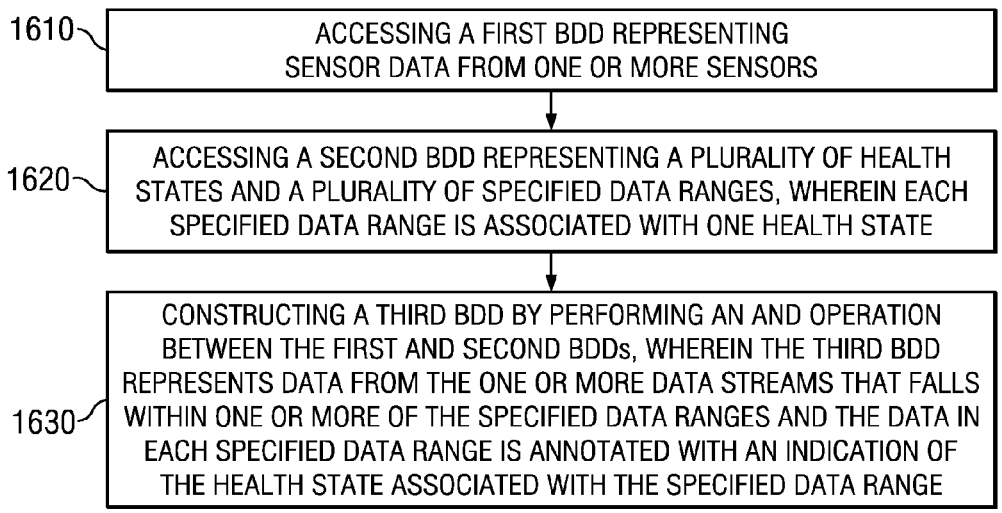
FIG. 16 illustrates an example method for annotating medical binary decision diagrams with health state information.

FIG. 16 illustrates an example method for annotating medical binary decision diagrams with health state information. The method begins at step 1610, where analysis system 180 accesses a first BDD representing one or more data streams from one or more sensors 112. At step 1620, analysis system 180 accesses a second BDD representing a plurality of health states and a plurality of specified data ranges. Each specified data range is associated with one health state. At step 1630, analysis system 180 constructs a third BDD by performing an AND operation between the first and second BDDs. The third BDD represents data from the one or more data streams that falls within one or more of the specified data ranges and the data in each specified data range is annotated with an indication of the health state associated with the specified data range. Although this disclosure describes and illustrates particular steps of the method of FIG. 16 as occurring in a particular order, this disclosure contemplates any suitable steps of the method of FIG. 16 occurring in any suitable order. Moreover, although this disclosure describes and illustrates particular components carrying out particular steps of the method of FIG. 16, this disclosure contemplates any suitable combination of any suitable components carrying out any suitable steps of the method of FIG. 16.

Display

Display system 190 may render, visualize, display, message, and publish to one or more users based on the one or more analysis outputs from analysis system 180. In particular embodiments, one or more subjects of one or more sensors 112 may be a user of display system 190. An analysis output from analysis system 180 may be transmitted to display system 190 over any suitable medium. Display system 190 may include any suitable I/O device that can enable communication between a person and display system 190. As an example and not by way of limitation, display system 190 may include a video monitor, speaker, touch screen, printer, another suitable I/O device or a combination of two or more of these. Display system 190 may be any computing device with a suitable I/O device, such as computer system 1700.

In particular embodiments, display system 190 may comprise one or more local display systems 130 or one or more remote display systems 140. Where display system 190 comprises multiple subsystems (e.g., local display systems 130 and remote display systems 140), display of analysis outputs may occur on one or more subsystems. As an example and not by way of limitation, local display systems 130 and remote display systems 140 may present identical displays based on the analysis output. As another example and not by way of limitation, local display systems 130 and remote display systems 140 may present different displays based on the analysis output. In particular embodiments, a user-input sensor in sensor array 110 may also function as display system 190. Any client system with a suitable I/O device may serve as a user-input sensor and display system 190. As an example and not by way of limitation, a smart phone with a touch screen may function both as a user-input sensor and as display system 190.

In particular embodiments, display system 190 may display an analysis output in real-time as it is received from analysis system 180. In various embodiments, real-time analysis of data streams from sensor array 110 by analysis system 180 allows a user to receive real-time information about the health status of a subject. It is also possible for the user to receive real-time feedback from display system 190 (e.g., warnings about health risks, recommending therapies, etc.).

Although this disclosure describes a display system 190 performing particular display-related processes using particular techniques, this disclosure contemplates a display system 190 performing any suitable display-related processes using any suitable techniques.

In particular embodiments, display system 190 may render and visualize data based on analysis output from analysis system 180. Display system 190 may render and visualize using any suitable means, including computer system 1400 with a suitable I/O device, such as a video monitor, speaker, touch screen, printer, another suitable I/O device or a combination of two or more of these.

Rendering is the process of generating an image from a model. The model is a description of an object in a defined language or data structure. The description may contain color, size, orientation, geometry, viewpoint, texture, lighting, shading, and other object information. The rendering may be any suitable image, such as a digital image or raster graphics image. Rendering may be performed on any suitable computing device.

Visualization is the process of creating images, diagrams, or animations to communicate information to a user. Visualizations may include diagrams, images, objects, graphs, charts, lists, maps, text, etc. Visualization may be performed on any suitable device that may present information to a user, including a video monitor, speaker, touch screen, printer, another suitable I/O device or a combination of two or more of these.

In some embodiments, rendering may be performed partially on analysis system 180 and partially on display system 190. In other embodiments, rendering is completely performed on analysis system 180, while visualization is performed on display system 190.

In particular embodiments, display system 190 may message and publish data based on analysis output from analysis system 180. Display system 190 may message and publish using any suitable means, including email, instant message, text message, audio message, page, MMS text, social network message, another suitable messaging or publishing means, or a combination of two or more of these.

In particular embodiments, display system 190 may publish some or all of the analysis output such that the publication may be viewed by one or more third-parties. In one embodiment, display system 190 may automatically publish the analysis output to one or more websites. As an example and not by way of limitation, a subject of a GPS sensor (such as, for example, a smart phone) may automatically have his location published to a social networking site (such as, for example, Facebook, Twitter, or Foursquare).

In particular embodiments, display system 190 may send or message some or all of the analysis output to one or more third-parties. In one embodiment, display system 190 may automatically send the analysis output to one or more healthcare providers. As an example and not by way of limitation, a subject wearing a portable blood glucose monitor may have all of the data from that sensor transmitted to his doctor. In another embodiment, display system 190 will only send the analysis output to a healthcare provider when one or more threshold criteria are met. As an example and not by way of limitation, a subject wearing a portable blood glucose monitor may not have any data from that sensor transmitted to his doctor unless his blood glucose data shows that he is severely hypoglycemic (e.g., below 2.8 mmol/l). In particular embodiments, display system 190 may message one or more alerts to a user or third-party based on the analysis output. An alert may contain a notice, warning, or recommendation for the user or third-party. As an example and not by way of limitation, a subject wearing a blood glucose monitor may receive an alert if his blood glucose level shows that he is moderately hypoglycemic (e.g., below 3.5 mmol/l) warning of the hypoglycemia and recommending that he eat something.

In particular embodiments, display system 190 may display one or more therapies to a user based on analysis output from analysis system 180. A therapy may be a recommended therapy for the user or a therapeutic feedback that provide a direct therapeutic benefit to the user. Display system 190 may deliver a variety of therapies, such as interventions, biofeedback, breathing exercises, progressive muscle relaxation exercises, presentation of personal media (e.g., music, personal pictures, etc.), offering an exit strategy (e.g., calling the user so he has an excuse to leave a stressful situation), references to a range of psychotherapeutic techniques, and graphical representations of trends (e.g., illustrations of health metrics over time), cognitive reframing therapy, and other therapeutic feedbacks. Although this disclosure describes display system 190 delivering particular therapies, this disclosure contemplates display system 190 delivering any suitable therapies.

Systems and Methods

Figure 17:
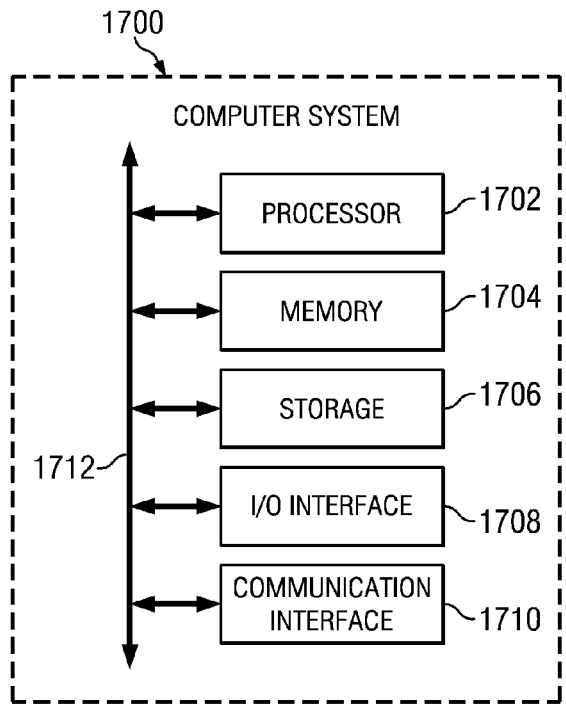
FIG. 17 illustrates an example computer system.

FIG. 17 illustrates an example computer system 1700. In particular embodiments, one or more computer systems 1700 perform one or more steps of one or more methods described or illustrated herein. In particular embodiments, one or more computer systems 1700 provide functionality described or illustrated herein. In particular embodiments, software running on one or more computer systems 1700 performs one or more steps of one or more methods described or illustrated herein or provides functionality described or illustrated herein. Particular embodiments include one or more portions of one or more computer systems 1700.

This disclosure contemplates any suitable number of computer systems 1700. This disclosure contemplates computer system 1700 taking any suitable physical form. As example and not by way of limitation, computer system 1700 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 1700 may include one or more computer systems 1700; be unitary or distributed; span multiple locations; span multiple machines; span multiple data centers; or reside in a cloud, which may include one or more cloud components in one or more networks. Where appropriate, one or more computer systems 1700 may perform without substantial spatial or temporal limitation one or more steps of one or more methods described or illustrated herein. As an example and not by way of limitation, one or more computer systems 1700 may perform in real time or in batch mode one or more steps of one or more methods described or illustrated herein. One or more computer systems 1700 may perform at different times or at different locations one or more steps of one or more methods described or illustrated herein, where appropriate.

In particular embodiments, computer system 1700 includes a processor 1702, memory 1704, storage 1706, an input/output (I/O) interface 1708, a communication interface 1710, and a bus 1712. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1702 includes hardware for executing instructions, such as those making up a computer program. As an example and not by way of limitation, to execute instructions, processor 1702 may retrieve (or fetch) the instructions from an internal register, an internal cache, memory 1704, or storage 1706; decode and execute them; and then write one or more results to an internal register, an internal cache, memory 1704, or storage 1706. In particular embodiments, processor 1702 may include one or more internal caches for data, instructions, or addresses. This disclosure contemplates processor 1702 including any suitable number of any suitable internal caches, where appropriate. As an example and not by way of limitation, processor 1702 may include one or more instruction caches, one or more data caches, and one or more translation lookaside buffers (TLBs). Instructions in the instruction caches may be copies of instructions in memory 1704 or storage 1706, and the instruction caches may speed up retrieval of those instructions by processor 1702. Data in the data caches may be copies of data in memory 1704 or storage 1706 for instructions executing at processor 1702 to operate on; the results of previous instructions executed at processor 1702 for access by subsequent instructions executing at processor 1702 or for writing to memory 1704 or storage 1706; or other suitable data. The data caches may speed up read or write operations by processor 1702. The TLBs may speed up virtual-address translation for processor 1702. In particular embodiments, processor 1702 may include one or more internal registers for data, instructions, or addresses. This disclosure contemplates processor 1702 including any suitable number of any suitable internal registers, where appropriate. Where appropriate, processor 1702 may include one or more arithmetic logic units (ALUs); be a multi-core processor; or include one or more processors 1702. Although this disclosure describes and illustrates a particular processor, this disclosure contemplates any suitable processor.

In particular embodiments, memory 1704 includes main memory for storing instructions for processor 1702 to execute or data for processor 1702 to operate on. As an example and not by way of limitation, computer system 1700 may load instructions from storage 1706 or another source (such as, for example, another computer system 1700) to memory 1704. Processor 1702 may then load the instructions from memory 1704 to an internal register or internal cache. To execute the instructions, processor 1702 may retrieve the instructions from the internal register or internal cache and decode them. During or after execution of the instructions, processor 1702 may write one or more results (which may be intermediate or final results) to the internal register or internal cache. Processor 1702 may then write one or more of those results to memory 1704. In particular embodiments, processor 1702 executes only instructions in one or more internal registers or internal caches or in memory 1704 (as opposed to storage 1706 or elsewhere) and operates only on data in one or more internal registers or internal caches or in memory 1704 (as opposed to storage 1706 or elsewhere). One or more memory buses (which may each include an address bus and a data bus) may couple processor 1702 to memory 1704. Bus 1712 may include one or more memory buses, as described below. In particular embodiments, one or more memory management units (MMUs) reside between processor 1702 and memory 1704 and facilitate accesses to memory 1704 requested by processor 1702. In particular embodiments, memory 1704 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1704 may include one or more memories 1704, where appropriate. Although this disclosure describes and illustrates particular memory, this disclosure contemplates any suitable memory.

In particular embodiments, storage 1706 includes mass storage for data or instructions. As an example and not by way of limitation, storage 1706 may include an HDD, a floppy disk drive, flash memory, an optical disc, a magneto-optical disc, magnetic tape, or a Universal Serial Bus (USB) drive or a combination of two or more of these. Storage 1706 may include removable or non-removable (or fixed) media, where appropriate. Storage 1706 may be internal or external to computer system 1700, where appropriate. In particular embodiments, storage 1706 is non-volatile, solid-state memory. In particular embodiments, storage 1706 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1706 taking any suitable physical form. Storage 1706 may include one or more storage control units facilitating communication between processor 1702 and storage 1706, where appropriate. Where appropriate, storage 1706 may include one or more storages 1706. Although this disclosure describes and illustrates particular storage, this disclosure contemplates any suitable storage.

In particular embodiments, I/O interface 1708 includes hardware, software, or both providing one or more interfaces for communication between computer system 1700 and one or more I/O devices. Computer system 1700 may include one or more of these I/O devices, where appropriate. One or more of these I/O devices may enable communication between a person and computer system 1700. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1708 for them. Where appropriate, I/O interface 1708 may include one or more device or software drivers enabling processor 1702 to drive one or more of these I/O devices. I/O interface 1708 may include one or more I/O interfaces 1708, where appropriate. Although this disclosure describes and illustrates a particular I/O interface, this disclosure contemplates any suitable I/O interface.

In particular embodiments, communication interface 1710 includes hardware, software, or both providing one or more interfaces for communication (such as, for example, packet-based communication) between computer system 1700 and one or more other computer systems 1700 or one or more networks. As an example and not by way of limitation, communication interface 1710 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1710 for it. As an example and not by way of limitation, computer system 1700 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1700 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1700 may include any suitable communication interface 1710 for any of these networks, where appropriate. Communication interface 1710 may include one or more communication interfaces 1710, where appropriate. Although this disclosure describes and illustrates a particular communication interface, this disclosure contemplates any suitable communication interface.

In particular embodiments, bus 1712 includes hardware, software, or both coupling components of computer system 1700 to each other. As an example and not by way of limitation, bus 1712 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 1712 may include one or more buses 1712, where appropriate. Although this disclosure describes and illustrates a particular bus, this disclosure contemplates any suitable bus or interconnect.

Herein, reference to a computer-readable storage medium encompasses one or more non-transitory, tangible computer-readable storage media possessing structure. As an example and not by way of limitation, a computer-readable storage medium may include a semiconductor-based or other integrated circuit (IC) (such, as for example, a field-programmable gate array (FPGA) or an application-specific IC (ASIC)), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, or another suitable computer-readable storage medium or a combination of two or more of these, where appropriate. Herein, reference to a computer-readable storage medium excludes any medium that is not eligible for patent protection under 35 U.S.C. §101. Herein, reference to a computer-readable storage medium excludes transitory forms of signal transmission (such as a propagating electrical or electromagnetic signal per se) to the extent that they are not eligible for patent protection under 35 U.S.C. §101. A computer-readable non-transitory storage medium may be volatile, non-volatile, or a combination of volatile and non-volatile, where appropriate.

This disclosure contemplates one or more computer-readable storage media implementing any suitable storage. In particular embodiments, a computer-readable storage medium implements one or more portions of processor 1702 (such as, for example, one or more internal registers or caches), one or more portions of memory 1704, one or more portions of storage 1706, or a combination of these, where appropriate. In particular embodiments, a computer-readable storage medium implements RAM or ROM. In particular embodiments, a computer-readable storage medium implements volatile or persistent memory. In particular embodiments, one or more computer-readable storage media embody software. Herein, reference to software may encompass one or more applications, bytecode, one or more computer programs, one or more executables, one or more instructions, logic, machine code, one or more scripts, or source code, and vice versa, where appropriate. In particular embodiments, software includes one or more application programming interfaces (APIs). This disclosure contemplates any suitable software written or otherwise expressed in any suitable programming language or combination of programming languages. In particular embodiments, software is expressed as source code or object code. In particular embodiments, software is expressed in a higher-level programming language, such as, for example, C, Perl, or a suitable extension thereof. In particular embodiments, software is expressed in a lower-level programming language, such as assembly language (or machine code). In particular embodiments, software is expressed in JAVA. In particular embodiments, software is expressed in Hyper Text Markup Language (HTML), Extensible Markup Language (XML), or other suitable markup language.

Figure 18:
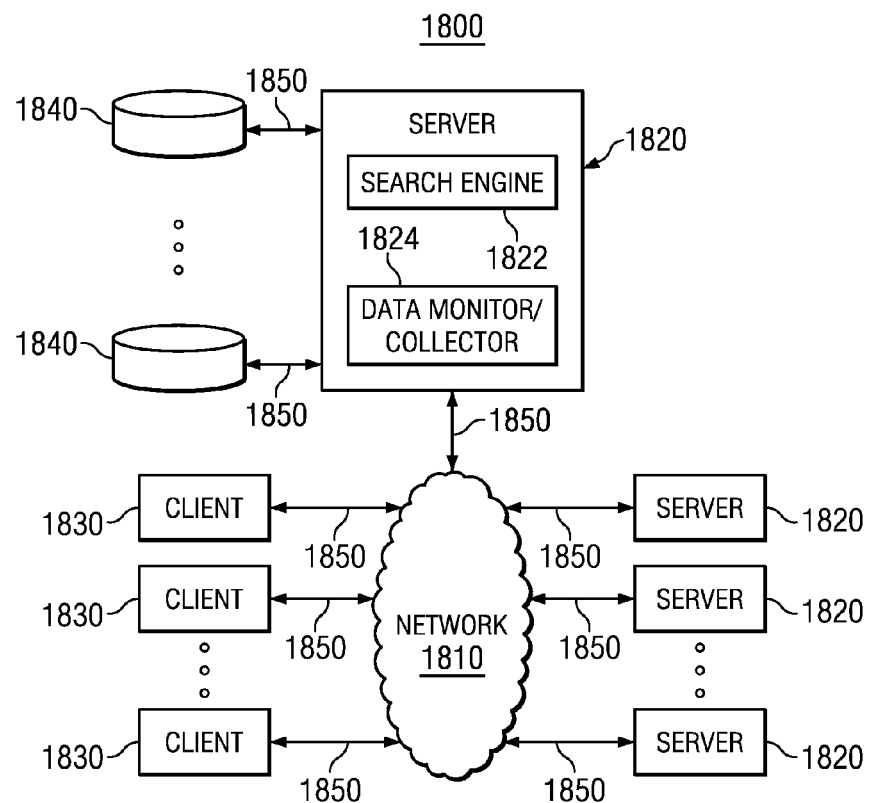
FIG. 18 illustrates an example network environment.

FIG. 18 illustrates an example network environment 1800. This disclosure contemplates any suitable network environment 1800. As an example and not by way of limitation, although this disclosure describes and illustrates a network environment 1800 that implements a client-server model, this disclosure contemplates one or more portions of a network environment 1800 being peer-to-peer, where appropriate. Particular embodiments may operate in whole or in part in one or more network environments 1800. In particular embodiments, one or more elements of network environment 1800 provide functionality described or illustrated herein. Particular embodiments include one or more portions of network environment 1800. Network environment 1800 includes a network 1810 coupling one or more servers 1820 and one or more clients 1830 to each other. This disclosure contemplates any suitable network 1810. As an example and not by way of limitation, one or more portions of network 1810 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 1810 may include one or more networks 1810.

Links 1850 couple servers 1820 and clients 1830 to network 1810 or to each other. This disclosure contemplates any suitable links 1850. As an example and not by way of limitation, one or more links 1850 each include one or more wireline (such as, for example, Digital Subscriber Line (DSL) or Data Over Cable Service Interface Specification (DOCSIS)), wireless (such as, for example, Wi-Fi or Worldwide Interoperability for Microwave Access (WiMAX)) or optical (such as, for example, Synchronous Optical Network (SONET) or Synchronous Digital Hierarchy (SDH)) links 1850. In particular embodiments, one or more links 1850 each includes an intranet, an extranet, a VPN, a LAN, a WLAN, a WAN, a MAN, a communications network, a satellite network, a portion of the Internet, or another link 1850 or a combination of two or more such links 1850. Links 1850 need not necessarily be the same throughout network environment 1800. One or more first links 1850 may differ in one or more respects from one or more second links 1850.

This disclosure contemplates any suitable servers 1820. As an example and not by way of limitation, one or more servers 1820 may each include one or more advertising servers, applications servers, catalog servers, communications servers, database servers, exchange servers, fax servers, file servers, game servers, home servers, mail servers, message servers, news servers, name or DNS servers, print servers, proxy servers, sound servers, standalone servers, web servers, or web-feed servers. In particular embodiments, a server 1820 includes hardware, software, or both for providing the functionality of server 1820. As an example and not by way of limitation, a server 1820 that operates as a web server may be capable of hosting websites containing web pages or elements of web pages and include appropriate hardware, software, or both for doing so. In particular embodiments, a web server may host HTML or other suitable files or dynamically create or constitute files for web pages on request. In response to a Hyper Text Transfer Protocol (HTTP) or other request from a client 1830, the web server may communicate one or more such files to client 1830. As another example, a server 1820 that operates as a mail server may be capable of providing e-mail services to one or more clients 1830. As another example, a server 1820 that operates as a database server may be capable of providing an interface for interacting with one or more data stores (such as, for example, data stores 1840 described below). Where appropriate, a server 1820 may include one or more servers 1820; be unitary or distributed; span multiple locations; span multiple machines; span multiple datacenters; or reside in a cloud, which may include one or more cloud components in one or more networks.

In particular embodiments, one or more links 1850 may couple a server 1820 to one or more data stores 1840. A data store 1840 may store any suitable information, and the contents of a data store 1840 may be organized in any suitable manner. As an example and not by way or limitation, the contents of a data store 1840 may be stored as a dimensional, flat, hierarchical, network, object-oriented, relational, XML, or other suitable database or a combination or two or more of these. A data store 1840 (or a server 1820 coupled to it) may include a database-management system or other hardware or software for managing the contents of data store 1840. The database-management system may perform read and write operations, delete or erase data, perform data deduplication, query or search the contents of data store 1840, or provide other access to data store 1840.

In particular embodiments, one or more servers 1820 may each include one or more search engines 1822. A search engine 1822 may include hardware, software, or both for providing the functionality of search engine 1822. As an example and not by way of limitation, a search engine 1822 may implement one or more search algorithms to identify network resources in response to search queries received at search engine 1822, one or more ranking algorithms to rank identified network resources, or one or more summarization algorithms to summarize identified network resources. In particular embodiments, a ranking algorithm implemented by a search engine 1822 may use a machine-learned ranking formula, which the ranking algorithm may obtain automatically from a set of training data constructed from pairs of search queries and selected Uniform Resource Locators (URLs), where appropriate.

In particular embodiments, one or more servers 1820 may each include one or more data monitors/collectors 1824. A data monitor/collection 1824 may include hardware, software, or both for providing the functionality of data collector/collector 1824. As an example and not by way of limitation, a data monitor/collector 1824 at a server 1820 may monitor and collect network-traffic data at server 1820 and store the network-traffic data in one or more data stores 1840. In particular embodiments, server 1820 or another device may extract pairs of search queries and selected URLs from the network-traffic data, where appropriate.

This disclosure contemplates any suitable clients 1830. A client 1830 may enable a user at client 1830 to access or otherwise communicate with network 1810, servers 1820, or other clients 1830. As an example and not by way of limitation, a client 1830 may have a web browser, such as MICROSOFT INTERNET EXPLORER or MOZILLA FIREFOX, and may have one or more add-ons, plug-ins, or other extensions, such as GOOGLE TOOLBAR or YAHOO TOOLBAR. A client 1830 may be an electronic device including hardware, software, or both for providing the functionality of client 1830. As an example and not by way of limitation, a client 1830 may, where appropriate, be an embedded computer system, an SOC, an SBC (such as, for example, a COM or SOM), a desktop computer system, a laptop or notebook computer system, an interactive kiosk, a mainframe, a mesh of computer systems, a mobile telephone, a PDA, a netbook computer system, a server, a tablet computer system, or a combination of two or more of these. Where appropriate, a client 1830 may include one or more clients 1830; be unitary or distributed; span multiple locations; span multiple machines; span multiple datacenters; or reside in a cloud, which may include one or more cloud components in one or more networks.

Miscellaneous

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context. Furthermore, "a", "an," or "the" is intended to mean "one or more," unless expressly indicated otherwise or indicated otherwise by context. Therefore, herein, "an A" or "the A" means "one or more A," unless expressly indicated otherwise or indicated otherwise by context.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, this disclosure encompasses any suitable combination of one or more features from any example embodiment with one or more features of any other example embodiment herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. A method comprising: by one or more computing devices,
    constructing a binary decision diagram (BDD) for representing one or more sets of data, wherein the BDD comprises one or more nodes, and each of the one or more nodes is encoded using n bits;
    while each of the one or more nodes is encoded using n bits, iteratively:
        adding data from the one or more sets of data to the BDD;
        compressing the BDD; and
        determining a compression rate of the BDD; and
    if the compression rate of the BDD drops below a first threshold, then encoding each of the one or more nodes of the BDD using n+d bits, wherein $d \geq 1$.

2. The method of claim 1, wherein:
    the BDD comprises one or more 0 edges and one or more 1 edges;
    each of the one or more 0 edges and one or more 1 edges is encoded using k bits; and
    the first threshold is when a number of nodes in the BDD is less than or equal to $2^k-1$.

3. The method of claim 1, wherein n=6 and d=1.

4. The method of claim 1, further comprising:
    while each of the one or more nodes is encoded using n+d bits, iteratively:
        adding data from the one or more sets of data to the BDD;
        compressing the BDD; and
        determining the compression rate of the BDD; and
    if the compression rate of the BDD drops below a second threshold, then encoding each of the one or more nodes of the BDD using n+2d bits.

5. The method of claim 1, further comprising optimizing and storing the BDD.

6. The method of claim 1, wherein the one or more sets of data are sensor data from one or more sensors.

7. The method of claim 6, wherein at least one of the one or more sensors is affixed to a person's body.

8. An apparatus comprising: one or more processors; and a memory coupled to the processors comprising instructions executable by the processors, the processors operable when executing the instructions to:
    construct a binary decision diagram (BDD) for representing one or more sets of data, wherein the BDD comprises one or more nodes, and each of the one or more nodes is encoded using n bits;
    while each of the one or more nodes is encoded using n bits, iteratively:
        add data from the one or more sets of data to the BDD;
        compress the BDD; and
        determine a compression rate of the BDD; and
    if the compression rate of the BDD drops below a first threshold, then encode each of the one or more nodes of the BDD using n+d bits, wherein $d \geq 1$.

9. The apparatus of claim 8, wherein:
    the BDD comprises one or more 0 edges and one or more 1 edges;
    each of the one or more 0 edges and one or more 1 edges is encoded using k bits; and
    the first threshold is when a number of nodes in the BDD is less than or equal to $2^k-1$.

10. The apparatus of claim 8, wherein n=6 and d=1.

11. The apparatus of claim 8, wherein the processors are further operable when executing the instructions to:
    while each of the one or more nodes is encoded using n+d bits, iteratively:
        add data from the one or more sets of data to the BDD;
        compress the BDD; and
        determine the compression rate of the BDD; and
    if the compression rate of the BDD drops below a second threshold, then encode each of the one or more nodes of the BDD using n+2d bits.

12. The apparatus of claim 8, wherein the processors are further operable when executing the instructions to optimize and storing the BDD.

13. The apparatus of claim 8, wherein the one or more sets of data are sensor data from one or more sensors.

14. The apparatus of claim 13, wherein at least one of the one or more sensors is affixed to a person's body.

15. One or more computer-readable non-transitory storage media embodying software that is operable when executed to:
   construct a binary decision diagram (BDD) for representing one or more sets of data, wherein the BDD comprises one or more nodes, and each of the one or more nodes is encoded using n bits;
   while each of the one or more nodes is encoded using n bits, iteratively:
      add data from the one or more sets of data to the BDD;
      compress the BDD; and
      determine a compression rate of the BDD; and
   if the compression rate of the BDD drops below a first threshold, then encode each of the one or more nodes of the BDD using n+d bits, wherein d≥1.

16. The media of claim 15, wherein:
   the BDD comprises one or more 0 edges and one or more 1 edges;
   each of the one or more 0 edges and one or more 1 edges is encoded using k bits; and
   the first threshold is when a number of nodes in the BDD is less than or equal to $2^k-1$.

17. The media of claim 15, wherein n=6 and d=1.

18. The media of claim 15, wherein the software is further operable when executed to:
   while each of the one or more nodes is encoded using n+d bits, iteratively:
      add data from the one or more sets of data to the BDD;
      compress the BDD; and
      determine the compression rate of the BDD; and
   if the compression rate of the BDD drops below a second threshold, then encode each of the one or more nodes of the BDD using n+2d bits.

19. The media of claim 15, wherein the software is further operable when executed to optimize and storing the BDD.

20. The media of claim 15, wherein the one or more sets of data are sensor data from one or more sensors.

21. The media of claim 20, wherein at least one of the one or more sensors is affixed to a person's body.

22. A system comprising:
   means for constructing a binary decision diagram (BDD) for representing one or more sets of data, wherein the BDD comprises one or more nodes, and each of the one or more nodes is encoded using n bits;
   while each of the one or more nodes is encoded using n bits, means for iteratively:
      adding data from the one or more sets of data to the BDD;
      compressing the BDD; and
      determining a compression rate of the BDD; and
   if the compression rate of the BDD drops below a first threshold, then means for encoding each of the one or more nodes of the BDD using n+d bits, wherein d≥1.

* * * * *